United States Patent
Akashi

(10) Patent No.: US 11,018,306 B2
(45) Date of Patent: May 25, 2021

(54) COMPOUND FOR THERMALLY ACTIVATED DELAYED FLUORESCENCE AND ORGANIC ELECTROLUMINESCENCE DEVICE INCLUDING THE SAME

(71) Applicant: Samsung Display Co., Ltd., Yongin-si (KR)

(72) Inventor: Nobutaka Akashi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 420 days.

(21) Appl. No.: 15/952,630

(22) Filed: Apr. 13, 2018

(65) Prior Publication Data

US 2019/0036034 A1 Jan. 31, 2019

(30) Foreign Application Priority Data

Jul. 26, 2017 (KR) .................. 10-2017-0094884

(51) Int. Cl.
*C07D 471/10* (2006.01)
*C07D 519/00* (2006.01)
(Continued)

(52) U.S. Cl.
CPC ........ *H01L 51/0072* (2013.01); *C07D 471/10* (2013.01); *C07D 519/00* (2013.01);
(Continued)

(58) Field of Classification Search
CPC ............ H01L 51/0071; H01L 51/0072; H01L 51/0067; H01L 51/5012; H01L 51/5206;
(Continued)

(56) References Cited

U.S. PATENT DOCUMENTS

2014/0252318 A1* 9/2014 Boudreault ......... H01L 51/0059
257/40

FOREIGN PATENT DOCUMENTS

CN 1157461 C 7/2004
JP 5408474 B2 2/2014
(Continued)

OTHER PUBLICATIONS

KR-20110107681-A—translated (Year: 2011).*
(Continued)

*Primary Examiner* — Lucas A Stelling
*Assistant Examiner* — Rachel Simbana
(74) *Attorney, Agent, or Firm* — Lewis Roca Rothgerber Christie LLP

(57) ABSTRACT

Provided are a compound for thermally activated delayed fluorescence having a molecular aspect ratio of 1.5 or more, represented by the following Formula 1 and an organic electroluminescence device including the same in an emission layer. The organic electroluminescence device includes a first electrode, a hole transport region disposed on the first electrode, an emission layer disposed on the hole transport
(Continued)

region, an electron transport region disposed on the emission layer, and a second electrode disposed on the electron transport region.

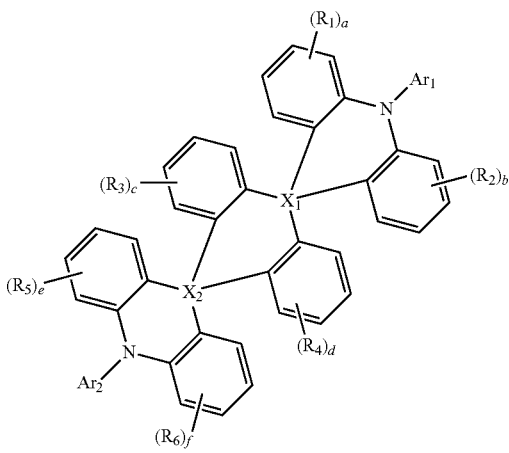

Formula 1

18 Claims, 2 Drawing Sheets

(51) Int. Cl.
| C07F 5/02 | (2006.01) |
| C07F 7/08 | (2006.01) |
| C07F 7/30 | (2006.01) |
| C09K 11/06 | (2006.01) |
| H01L 51/00 | (2006.01) |
| H01L 51/50 | (2006.01) |
| H01L 51/52 | (2006.01) |

(52) U.S. Cl.
CPC ............ *C07F 5/027* (2013.01); *C07F 7/0816* (2013.01); *C07F 7/30* (2013.01); *C09K 11/06* (2013.01); *H01L 51/008* (2013.01); *H01L 51/0067* (2013.01); *H01L 51/0071* (2013.01); *H01L 51/0077* (2013.01); *H01L 51/0094* (2013.01); *C09K 2211/1018* (2013.01); *C09K 2211/1059* (2013.01); *C09K 2211/188* (2013.01); *H01L 51/508* (2013.01); *H01L 51/5012* (2013.01); *H01L 51/5016* (2013.01); *H01L 51/5064* (2013.01); *H01L 51/5088* (2013.01); *H01L 51/5092* (2013.01); *H01L 51/5206* (2013.01); *H01L 51/5221* (2013.01)

(58) Field of Classification Search
CPC ............ H01L 51/5221; H01L 51/5016; H01L 51/5064; H01L 51/508; H01L 51/5088; H01L 51/5092; H01L 51/008; H01L 51/0094; H01L 51/0077; C07D 219/00; C07D 471/14; C07D 471/04; C07D 519/00; C07D 471/10; C09K 19/3447; C09K 11/06; C09K 2211/1059; C09K 2211/1018; C09K 2211/188; C07F 9/6584; C07F 5/027; C07F 7/0816; C07F 7/30

See application file for complete search history.

(56) References Cited

FOREIGN PATENT DOCUMENTS

| KR | 20110107681 A | * | 10/2011 |
| KR | 20170044821 A | * | 4/2017 |
| KR | 10-1771531 B1 | | 8/2017 |

OTHER PUBLICATIONS

KR-20170044821-A—translated (Year: 2017).*
Yokoyama, Daisuke; "Molecular orientation in small-molecule organic light-emitting diodes"; Journal of Materials Chemistry; vol. 21; 2011; pp. 19187-19202.

* cited by examiner

COMPOUND FOR THERMALLY ACTIVATED DELAYED FLUORESCENCE AND ORGANIC ELECTROLUMINESCENCE DEVICE INCLUDING THE SAME

CROSS-REFERENCE TO RELATED APPLICATION

This patent application claims priority to and the benefit of Korean Patent Application No. 10-2017-0094884, filed on Jul. 26, 2017, the entire contents of which are incorporated herein by reference.

BACKGROUND

Development on an organic electroluminescence display as an image display is being actively conducted. An organic electroluminescence display is different from a liquid crystal display and is so called a self-luminescent display that displays an image by recombining holes and electrons injected from a first electrode and a second electrode in an emission layer and emitting light from a luminescent material which is an organic compound included in the emission layer.

As an organic electroluminescence device, for example, an organic device composed of a first electrode, a hole transport layer disposed on the first electrode, an emission layer disposed on the hole transport layer, an electron transport layer disposed on the emission layer, and a second electrode disposed on the electron transport layer has been prepared. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light using light emitted during the transition of the excitons back to a ground state. In addition, the configuration of an organic electroluminescence device is not limited to those described above, and various modifications may be made.

SUMMARY

The present disclosure provides a compound for thermally activated delayed fluorescence and an organic electroluminescence device including the same. For example, the present disclosure provides a compound for thermally activated delayed fluorescence considering a molecular aspect ratio and an organic electroluminescence device including the same in an emission layer.

An embodiment of the present disclosure provides a compound for thermally activated delayed fluorescence having a molecular aspect ratio of 1.5 or more, represented by the following Formula 1:

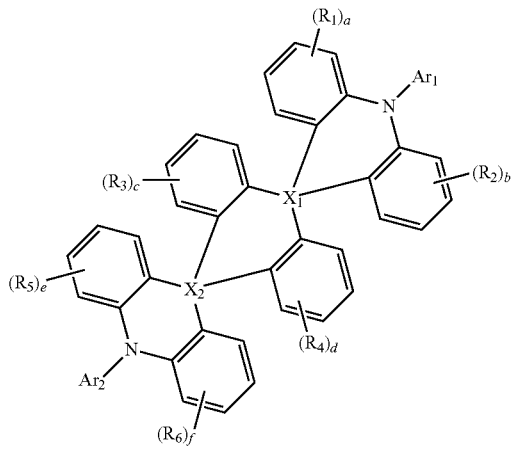

Formula 1

In Formula 1, $X_1$ and $X_2$ are each independently C, Si or Ge, $R_1$ to $R_6$ are each independently a hydrogen atom, a deuterium atom, a halogen atom, or a substituted or unsubstituted alkyl group having 1 to 3 carbon atoms, "a" to "f" are each independently an integer of 0 to 4, $Ar_1$ and $Ar_2$ are each independently a substituted or unsubstituted aryl group having 6 to 60 carbon atoms for forming a ring, or a substituted or unsubstituted heteroaryl group having 2 to 60 carbon atoms for forming a ring, and at least one of $Ar_1$ or $Ar_2$ is an electron accepting group.

In an embodiment, at least one of $Ar_1$ or $Ar_2$ may be a substituted or unsubstituted heteroaryl group, or an aryl group substituted with a substituted or unsubstituted heteroaryl group.

In an embodiment, $Ar_1$ and $Ar_2$ may be different from each other.

In an embodiment, at least one of $Ar_1$ or $Ar_2$ may be represented by any one of the following Formula 2 or 3:

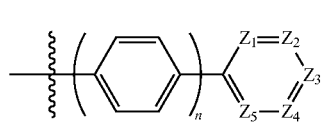

Formula 2

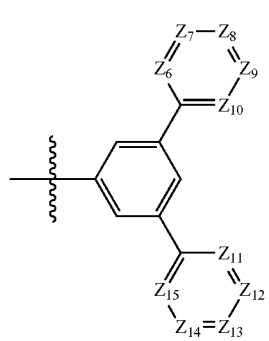

Formula 3

In Formula 2, n is 0 or 1, and $Z_1$ to $Z_5$ are each independently N or $CR_7$. When n is 0, $Z_1$ and $Z_5$ are each independently N or CH. One or two of $Z_1$ to $Z_5$ are N, and $R_7$ is a hydrogen atom, a deuterium atom, a cyano group, a methyl group, a substituted or unsubstituted phenyl group, a substituted or unsubstituted pyridine group, or a substituted or unsubstituted pyrimidine group.

In Formula 3, $Z_6$ to $Z_{15}$ are each independently N or $CR_8$, at least one chosen from $Z_6$ to $Z_{15}$ is N, and $R_8$ is a hydrogen atom, a deuterium atom, a cyano group, or a methyl group.

In an embodiment, at least one of $Ar_1$ or $Ar_2$ may be represented by any one of the following Formulae 4 to 6:

Formula 4

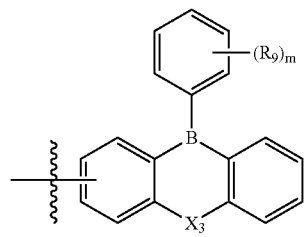

Formula 5

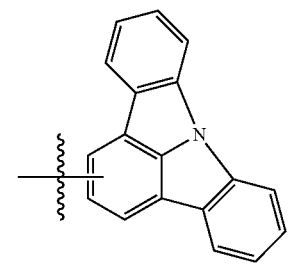

Formula 6

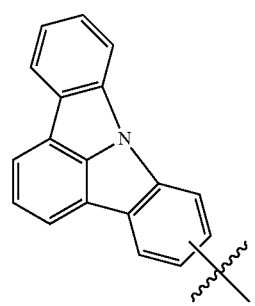

In Formula 4, $X_3$ is O or S, $R_9$ is a hydrogen atom, a deuterium atom, or a substituted or unsubstituted alkyl group having 1 to 5 carbon atoms, and m is an integer of 0 to 5.

In an embodiment, at least one of $X_1$ or $X_2$ may be C.

In an embodiment, Formula 1 may be represented by the following Formula 1-1:

Formula 1-1

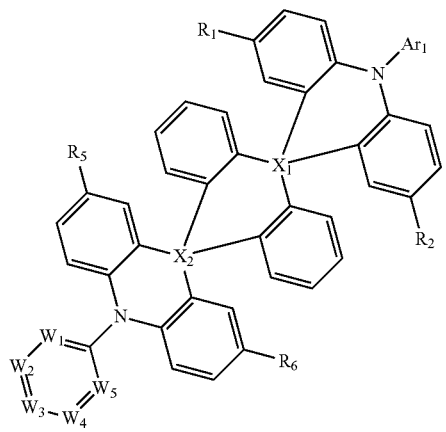

In Formula 1-1, $Ar_1$ is a substituted or unsubstituted heteroaryl group, or an aryl group substituted with a substituted or unsubstituted heteroaryl group, $R_1$, $R_2$, $R_5$ and $R_6$ are each independently a hydrogen atom, a deuterium atom, or a methyl group, $W_1$ to $W_5$ are each independently CH or N, the number of N in $W_1$ to $W_5$ is 0, 1, or 2, and $X_1$ and $X_2$ are the same as defined above.

In an embodiment, the compound for thermally activated delayed fluorescence may have an absolute value of the difference between the singlet energy level and the triplet energy level of about 0.2 eV or less.

An embodiment of the present disclosure provides an organic electroluminescence device including a first electrode, a hole transport region disposed on the first electrode, an emission layer disposed on the hole transport region, an electron transport region disposed on the emission layer, and a second electrode disposed on the electron transport region, in which the emission layer includes the compound for thermally activated delayed fluorescence according to an embodiment of the present disclosure. The first electrode and the second electrode may each independently comprise at least one selected from AQ, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof.

In an embodiment, the emission layer may include a host and a dopant, and the dopant may include the compound for thermally activated delayed fluorescence according to an embodiment of the present disclosure.

In an embodiment, the compound for thermally activated delayed fluorescence according to an embodiment of the present disclosure may emit blue light with a wavelength range of about 470 nm or shorter.

BRIEF DESCRIPTION OF THE FIGURES

The accompanying drawings are included to provide a further understanding of the subject matter of the present disclosure, and are incorporated in and constitute a part of this specification. The drawings illustrate exemplary embodiments of the present disclosure and, together with the description, serve to explain features of the present disclosure. In the drawings.

DETAILED DESCRIPTION

Figure 1:
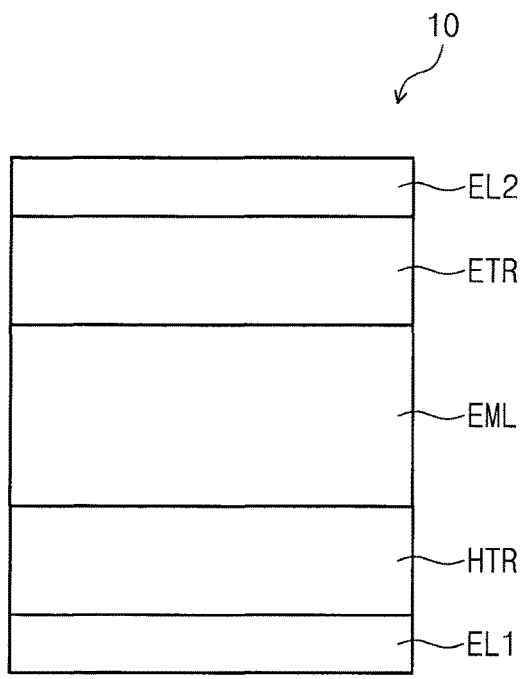
FIG. 1 is a schematic cross-sectional view of an organic electroluminescence device according to an embodiment of the present disclosure.

The above objects, other objects, features and/or advantages of the subject matter of the present disclosure will be readily understood from exemplary embodiments with reference to the accompanying drawings. The subject matter of the present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art.

Like reference numerals refer to like elements for explaining each drawing. In the drawings, the sizes of elements may be enlarged for clarity of the subject matter of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be directly on the other part, or intervening layers may also be present. On the contrary, when a layer, a film, a region, a plate, etc. is referred to as being "under" another part, it can be directly under the other part, or intervening layers may also be present.

In the present disclosure,

means a part to be coupled or connected.

In the present disclosure, "substituted or unsubstituted" may mean unsubstituted or substituted with at least one substituent selected from the group consisting of deuterium atom, halogen atom, cyano group, nitro group, amino group, silyl group, boron group, phosphine oxide group, phosphine sulfide group, alkyl group, alkenyl group, aryl group and heterocyclic group. In addition, each of the substituent illustrated above may be substituted or unsubstituted. For example, biphenyl may be interpreted as aryl group, or phenyl group substituted with phenyl.

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 10, 1 to 5, 1 to 4, or 1 to 3. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 60, 6 to 30, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, the fluorenyl group may be substituted, and two substituents may be combined with each other to form a spiro structure. Examples of the substituted fluorenyl group may include the following groups, without limitation:

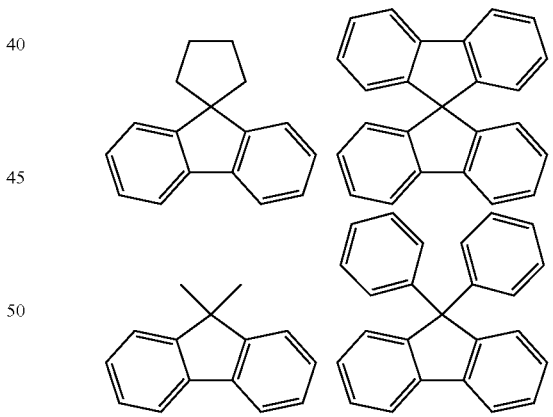

In the present disclosure, the heteroaryl group may be heteroaryl including at least one chosen from B, O, N, P, Si, or S as a heteroatom. When the heteroaryl group includes two heteroatoms, the two heteroatoms may be the same or different from each other. The carbon number of the heteroaryl group for forming a ring may be 2 to 30, or 2 to 20. The heteroaryl group may be monocyclic heteroaryl or polycyclic heteroaryl. Polycyclic heteroaryl may have bicyclic or tricyclic structure, for example. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilole, dibenzofuranyl, etc., without limitation.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boron and aryl boron. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number is not specifically limited, and may be 2 to 10, 2 to 8, or 2 to 6. Examples of the alkenyl group may include vinyl, 1-butenyl, 1-pentenyl, 1,3-butadienyl, styrenyl, styrylvinyl, etc., without limitation.

In the present disclosure, the carbon number of the amino group is not specifically limited, and may be 1 to 30. The amino group may include alkyl amino and aryl amino. Examples of the amino group may include methylamino, dimethylamino, phenylamine, diphenylamino, naphthylamine, 9-methyl-anthracenylamino, triphenylamino, etc., without limitation.

Hereinafter, the compound for thermally activated delayed fluorescence according to an embodiment of the present disclosure will be explained.

The compound for thermally activated delayed fluorescence according to an embodiment of the present disclosure has a molecular aspect ratio of 1.5 or more and is represented by the following Formula 1:

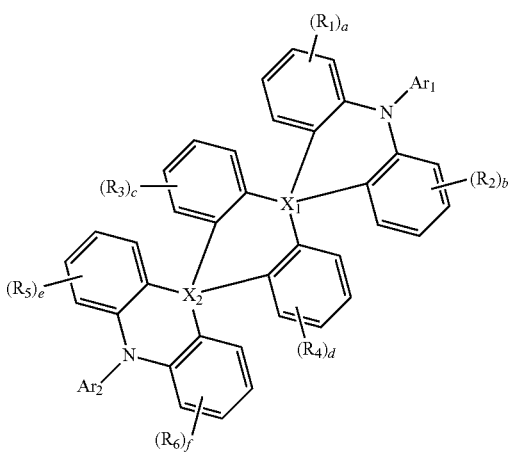

Formula 1

In Formula 1, $X_1$ and $X_2$ are each independently C, Si or Ge. At least one chosen from $X_1$ and $X_2$ may be represented by C (carbon atom). However, an embodiment of the present disclosure is not limited thereto. For example, both of $X_1$ and $X_2$ may be C, and one of $X_1$ or $X_2$ may be C and the other may be Si. For example, one of $X_1$ or $X_2$ may be C and the other may be Ge.

In Formula 1, $R_1$ to $R_6$ are each independently a hydrogen atom, a deuterium atom, a halogen atom, or a substituted or unsubstituted alkyl group having 1 to 3 carbon atoms, and "a" to "f" are each independently an integer of 0 to 4.

In case "a" is an integer of 2 or more, a plurality of $R_1$ may be the same or different from each other. In case "b" is an integer of 2 or more, a plurality of $R_2$ may be the same or different from each other. In case "c" is an integer of 2 or more, a plurality of $R_3$ may be the same or different from each other. In case "d" is an integer of 2 or more, a plurality of $R_4$ may be the same or different from each other. In case "e" is an integer of 2 or more, a plurality of $R_5$ may be the same or different from each other. In case "f" is an integer of 2 or more, a plurality of $R_6$ may be the same or different from each other.

For example, $R_1$ to $R_6$ may be each independently a hydrogen atom, a deuterium atom, or a substituted or unsubstituted methyl group.

In Formula 1, $Ar_1$ and $Ar_2$ are each independently a substituted or unsubstituted aryl group having 6 to 60 carbon atoms for forming a ring, or a substituted or unsubstituted heteroaryl group having 2 to 60 carbon atoms for forming a ring. $Ar_1$ and $Ar_2$ may be each independently a substituted or unsubstituted aryl group having 6 to 20 carbon atoms for forming a ring, or a substituted or unsubstituted heteroaryl group having 2 to 20 carbon atoms for forming a ring. $Ar_1$ and $Ar_2$ may not include a triazine group.

In order to design a compound with a molecular aspect ratio of 1.5 or more, when $Ar_1$ and $Ar_2$ are substituted, the carbon atom at the ortho position of the nitrogen atom may be unsubstituted. For example, in case $Ar_1$ and $Ar_2$ are substituted, a substituent may be substituted at the meta or para position of the nitrogen atom.

The compound having a molecular aspect ratio of 1.5 or more, represented by Formula 1, may be readily applied as emission materials for thermally activated delayed fluorescence with superior efficiency. As disclosed in D. Yokoyama, J. Mater. Chem. 21, 19187-19202 (2011), in case an organic thin film may be used in which the molecular orientation is horizontally controlled, a charge transport property as well as light extraction efficiency may be enhanced. In the present disclosure, in order to control readily the molecular orientation horizontally, a molecule of a long and thin shape is suitable or preferred. For example, a molecule having an aspect ratio of 1.5 or more would have an enhanced effect.

At least one of $Ar_1$ or $Ar_2$ is an electron accepting group. At least one of $Ar_1$ or $Ar_2$ may be a substituted or unsubstituted heteroaryl group, or an aryl group substituted with a substituted or unsubstituted heteroaryl group. At least one of $Ar_1$ or $Ar_2$ may be represented by any one of the following Formula 2 or 3:

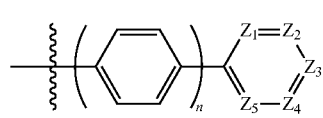

Formula 2

Formula 3

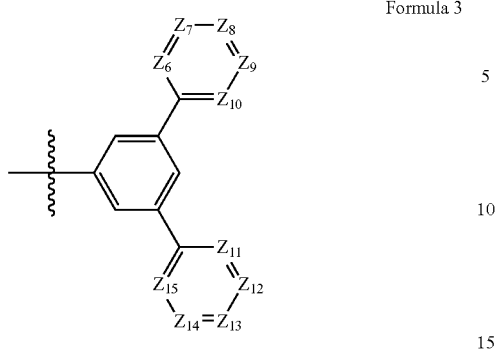

In Formula 2, n is 0 or 1.

In Formula 2, $Z_1$ to $Z_5$ are each independently N or $CR_7$. When n is 0, $Z_1$ and $Z_5$ are each independently N or CH. One or two of $Z_1$ to $Z_5$ are N, and $R_7$ is a hydrogen atom, a deuterium atom, a cyano group, a methyl group, a substituted or unsubstituted phenyl group, a substituted or unsubstituted pyridine group, or a substituted or unsubstituted pyrimidine group.

In Formula 2, n may be 0, $Z_2$ and $Z_4$ may be each independently $CR_7$, and $R_7$ may be each independently a hydrogen atom, a deuterium atom, a substituted or unsubstituted phenyl group, or a substituted or unsubstituted pyridine group. An embodiment of the present disclosure is not limited thereto, however, n may be 1.

Formula 2 may be represented by any one of the following Formulae 2-1 to 2-12:

Formula 2-1

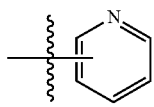

Formula 2-2

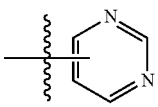

[Formula 2-3

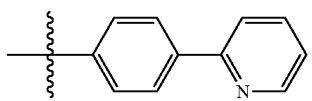

Formula 2-4

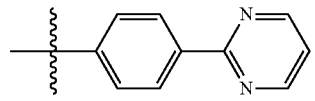

Formula 2-5

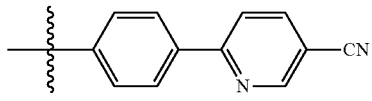

Formula 2-6

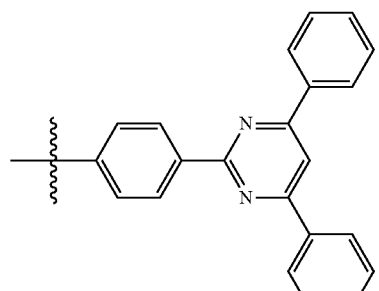

Formula 2-7

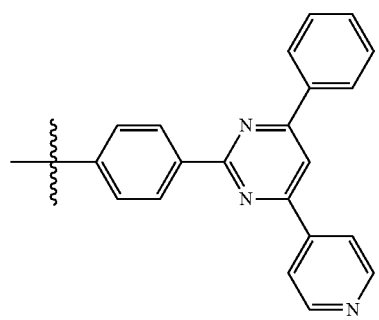

Formula 2-8

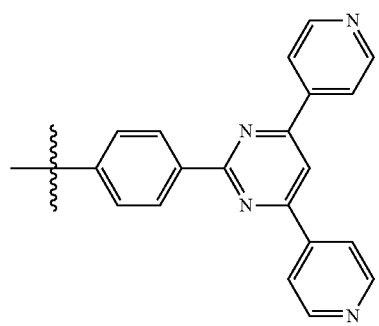

Formula 2-9

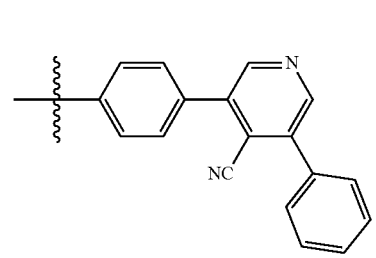

Formula 2-10

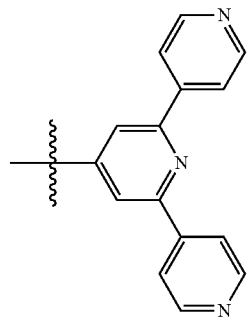

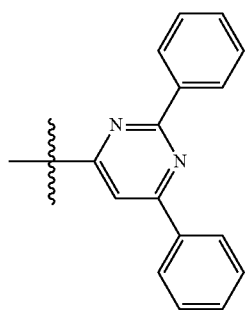

Formula 2-11

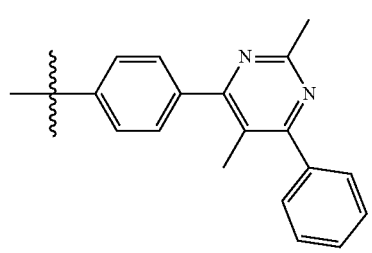

Formula 2-12

In Formula 3, $Z_6$ to $Z_{15}$ are each independently N or $CR_8$, at least one chosen from $Z_6$ to $Z_{15}$ is N, and $R_8$ is a hydrogen atom, a deuterium atom, a cyano group, or a methyl group.

The number of N in $Z_6$ to $Z_{15}$ may be 0, 1, 2, 3 or 4. The number of N in $Z_6$ to $Z_{10}$ may be 0, 1, or 2, and the number of N in $Z_{11}$ to $Z_{15}$ may be 0, 1, or 2.

Formula 3 may be represented by the following Formula 3-1 or 3-2:

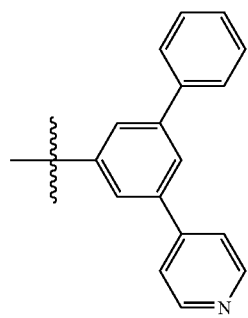

Formula 3-1

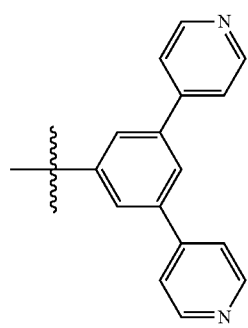

Formula 3-2

At least one of $Ar_1$ or $Ar_2$ may be represented by any one of the following Formulae 4 to 6:

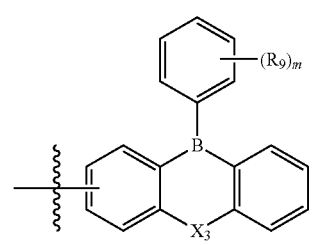

Formula 4

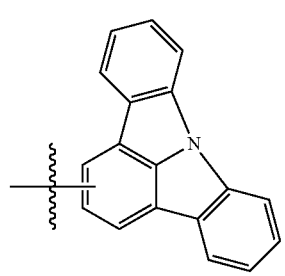

Formula 5

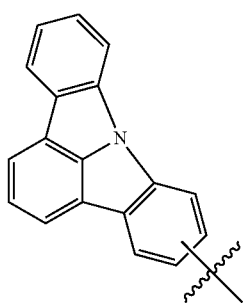

Formula 6

In Formula 4, $X_3$ is O or S, $R_9$ is a hydrogen atom, a deuterium atom, or a substituted or unsubstituted alkyl group having 1 to 5 carbon atoms, and m is an integer of 0 to 5.

In case m is an integer of 2 or more, a plurality of $R_9$ may be the same or different from each other. m may be 1 or more.

Formula 4 may be represented by the following Formula 4-1 or 4-2:

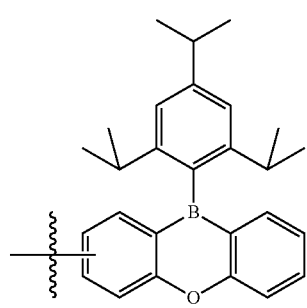

Formula 4-1

Formula 4-2

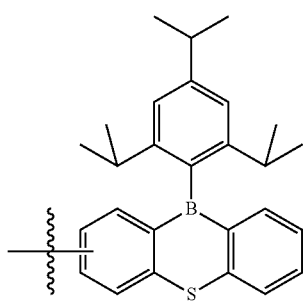

Formula 5 may be represented by the following Formula 5-1:

Formula 5-1

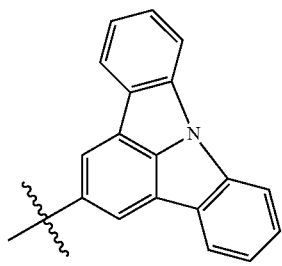

Formula 6 may be represented by the following Formula 6-1:

Formula 6-1

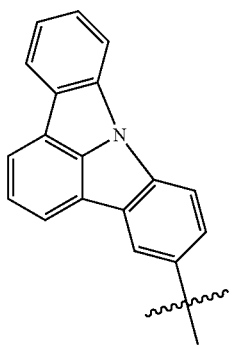

In Formula 1, $Ar_1$ and $Ar_2$ may be different from each other. An embodiment of the present disclosure is not limited thereto, however, $Ar_1$ and $Ar_2$ may be each independently a pyrimidine group, for example. In this case, the position of substituent at pyrimidine group may be different.

The compound for thermally activated delayed fluorescence according to an embodiment of the present disclosure may have an asymmetric molecular structure.

Formula 1 may be represented by the following Formula 1-1. However, an embodiment of the present disclosure is not limited thereto:

Formula 1-1

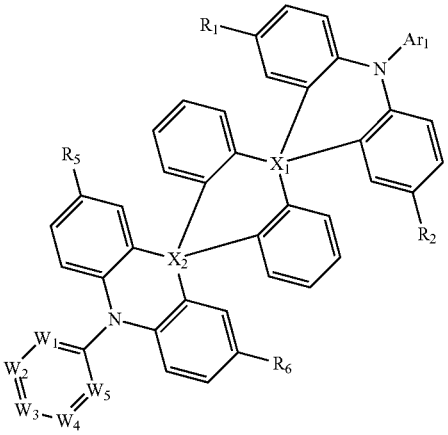

In Formula 1-1, $Ar_1$ is a substituted or unsubstituted heteroaryl group, or an aryl group substituted with a substituted or unsubstituted heteroaryl group, $R_1$, $R_2$, $R_5$ and $R_6$ are each independently a hydrogen atom, a deuterium atom, or a methyl group, $W_1$ to $W_5$ are each independently CH or N, the number of N in $W_1$ to $W_5$ is 0, 1, or 2, and $X_1$ and $X_2$ are the same as defined above.

In Formula 1-1, the ring including $W_1$ to $W_5$ may be a phenyl group or a pyrimidine group.

In Formula 1-1, $R_1$, $R_2$, $R_5$ and $R_6$ may be each independently a hydrogen atom. An embodiment of the present disclosure is not limited thereto, however, $R_1$ and $R_2$ may be a methyl group, and $R_5$ and $R_6$ may be a hydrogen atom. $R_1$ and $R_2$ may be a hydrogen atom, and $R_5$ and $R_6$ may be a methyl group. As another example, $R_1$, $R_2$, $R_5$ and $R_6$ may be each independently a methyl group.

The compound for thermally activated delayed fluorescence according to an embodiment of the present disclosure may have an absolute value of the difference between the singlet energy level and the triplet energy level of about 0.2 eV or less. For example, the absolute value of the difference between the singlet energy level and the triplet energy level may be 0.15 eV or less, or 0.1 eV or less.

The compound for thermally activated delayed fluorescence according to an embodiment of the present disclosure may be any one selected from the group consisting of compounds represented in the following Compound Group 1. However, an embodiment of the present disclosure is not limited thereto:

Compound Group 1

1

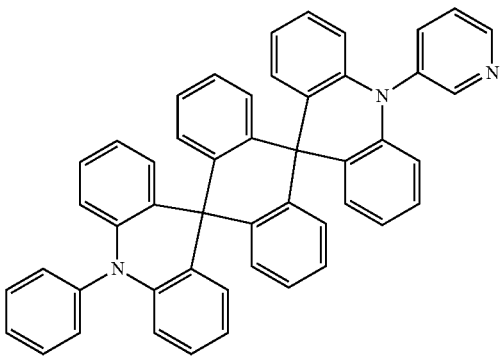

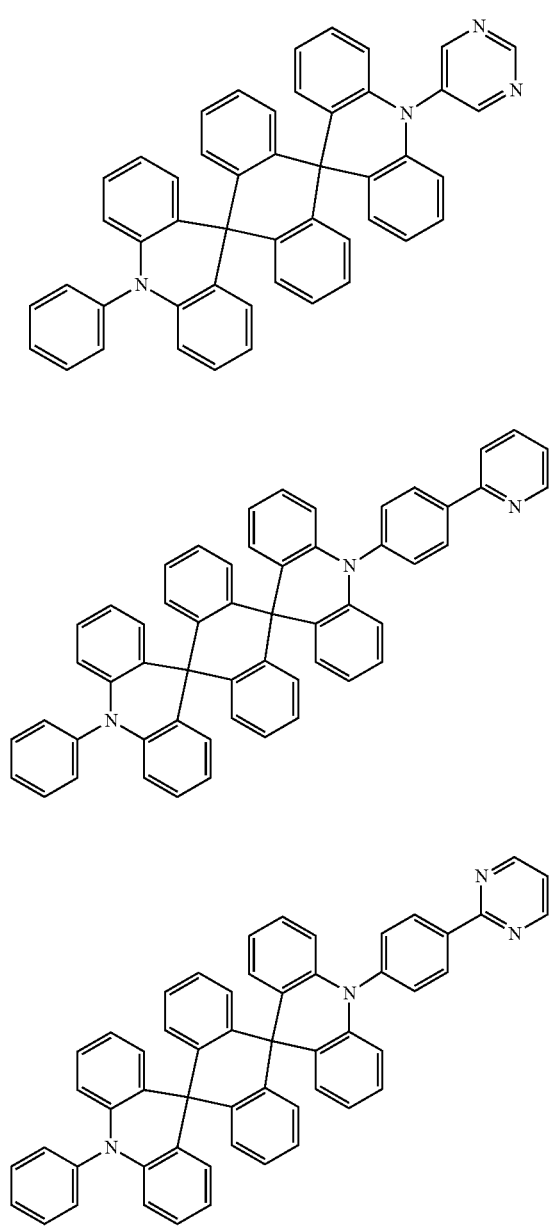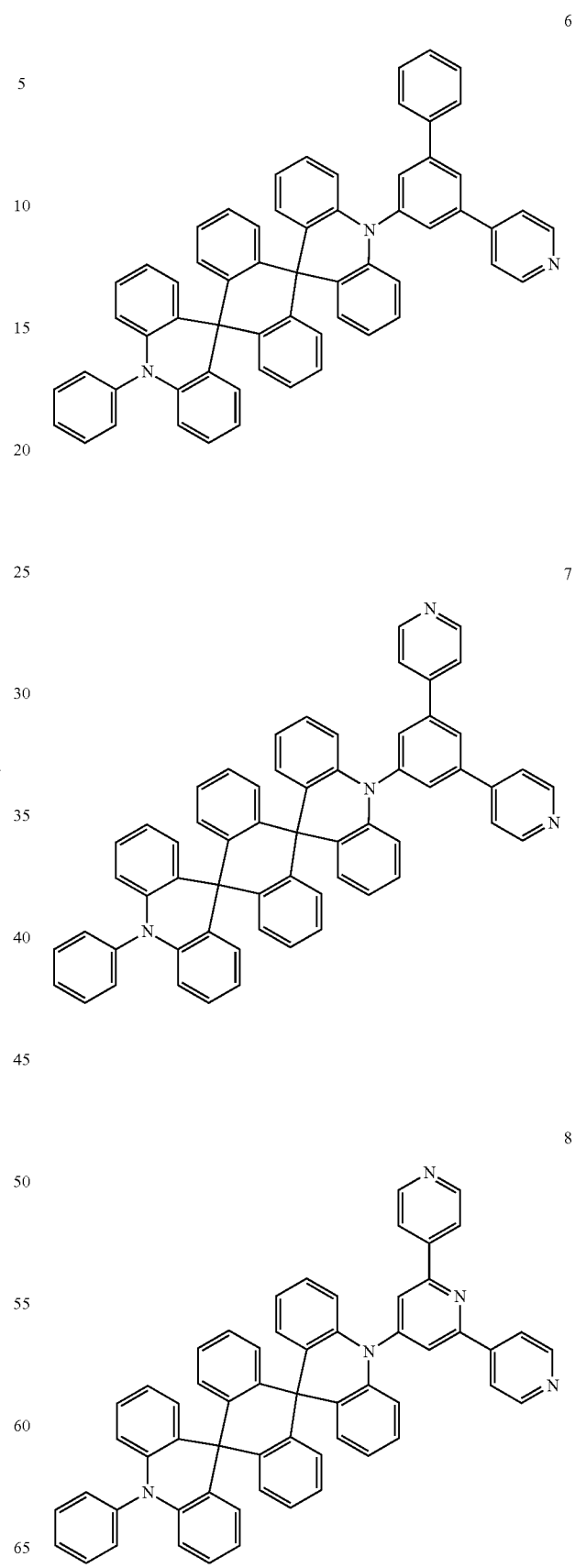

9
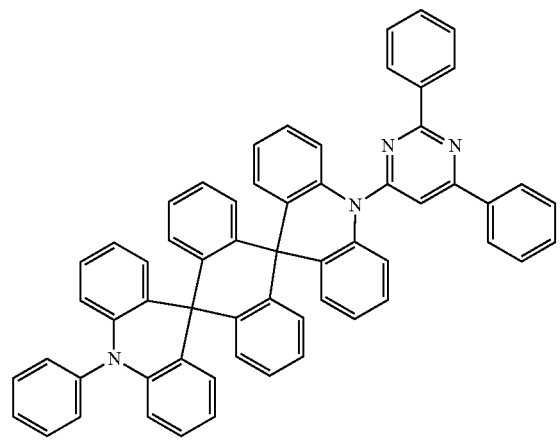
10
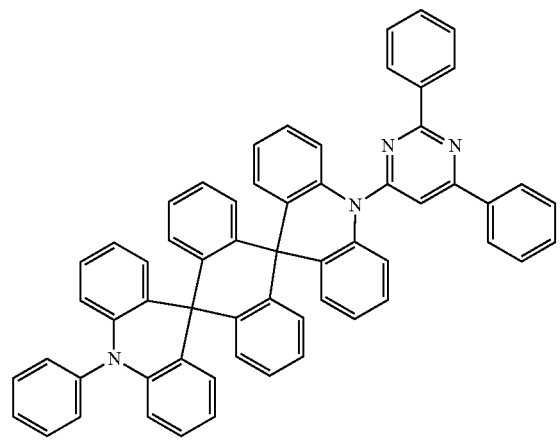
11
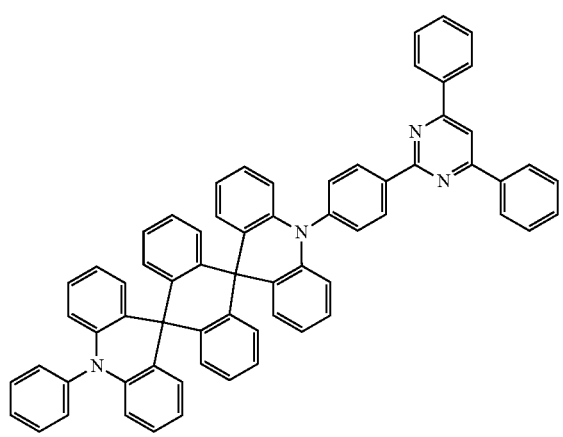
12
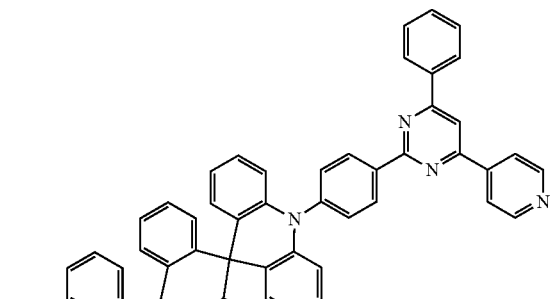
13
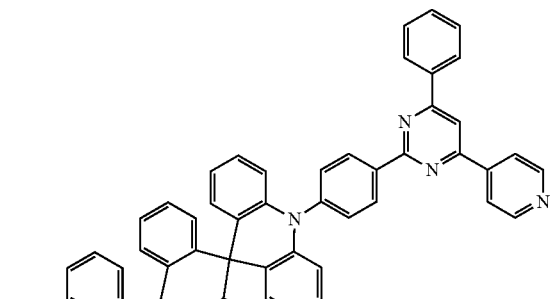
14
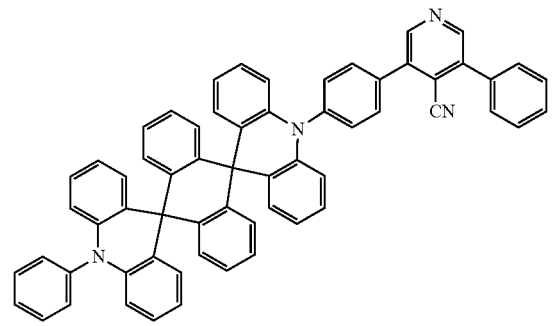

15
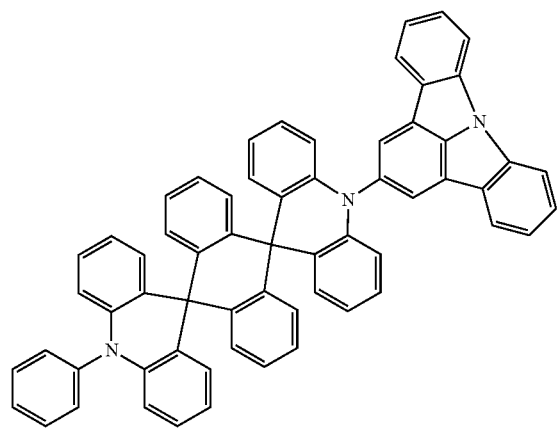
16
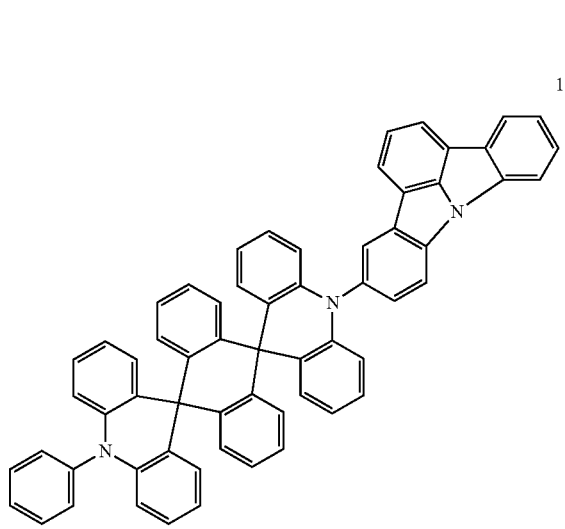
17
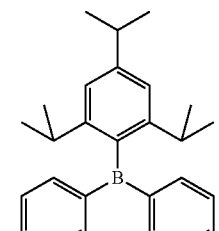
18
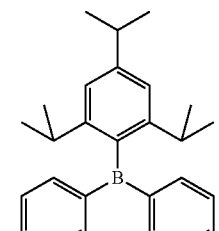
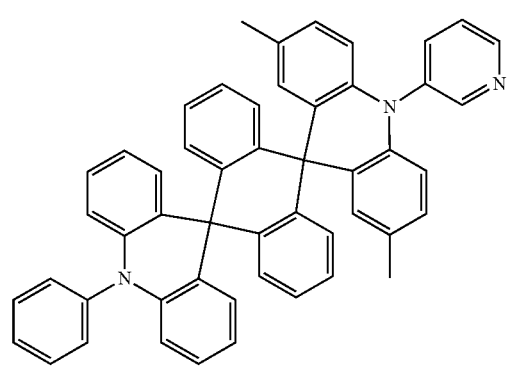
19
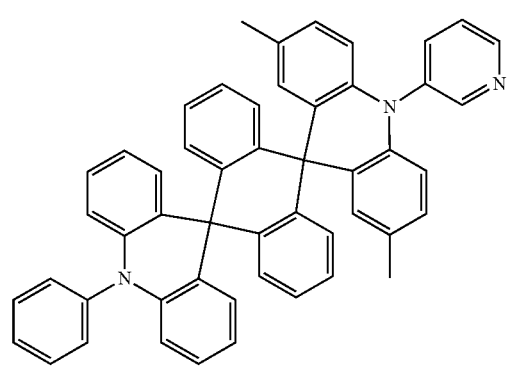
20
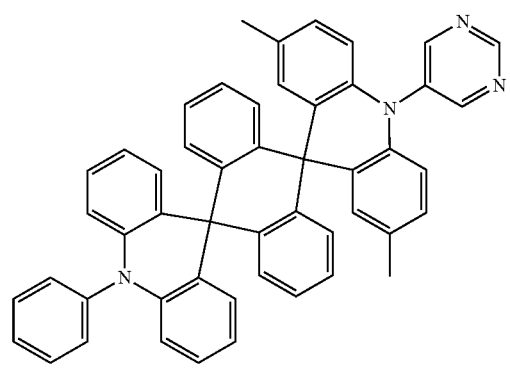
21
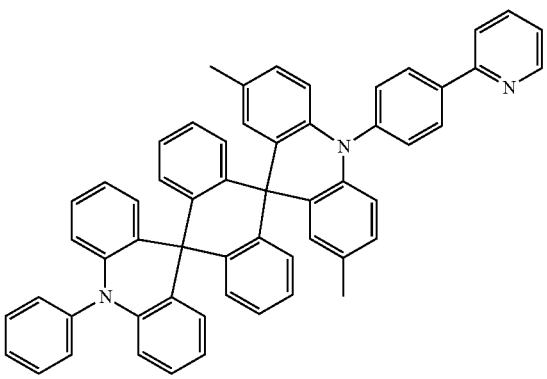

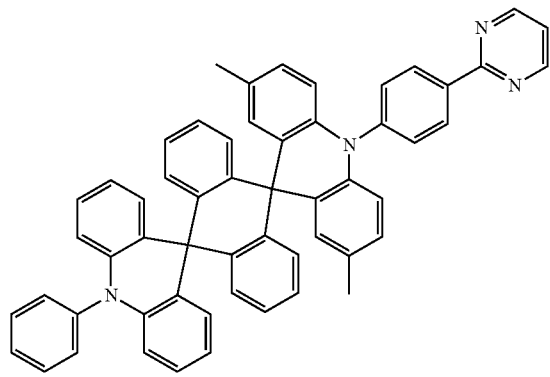
22
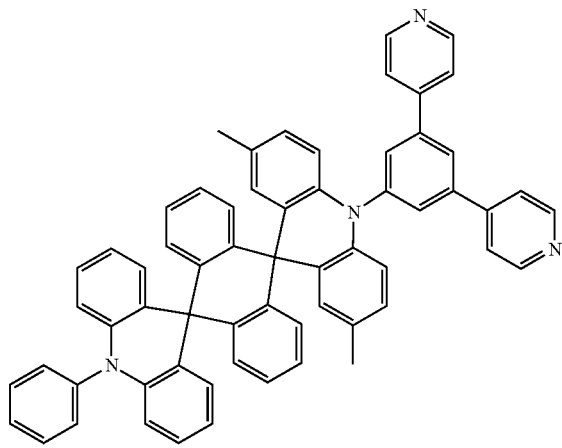
25
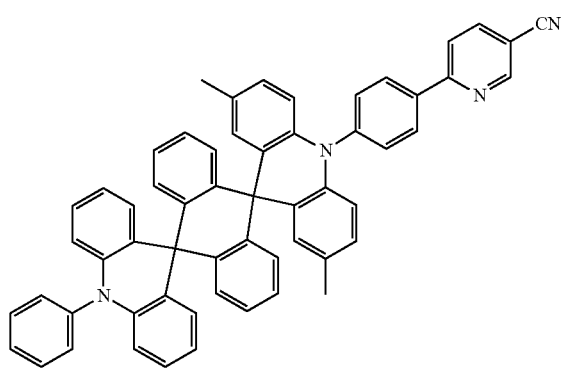
23
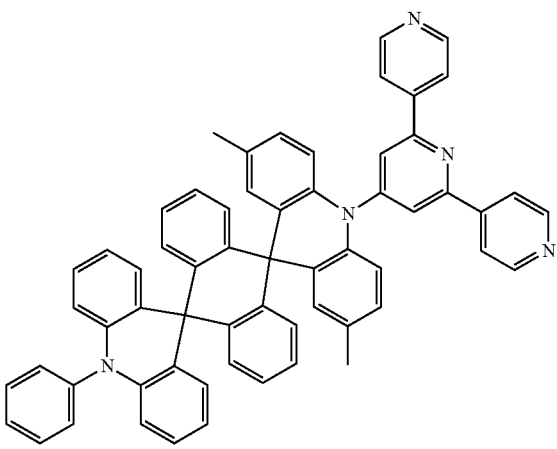
26
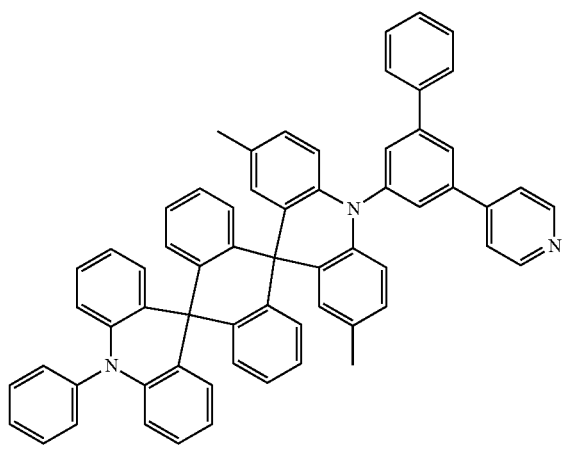
24
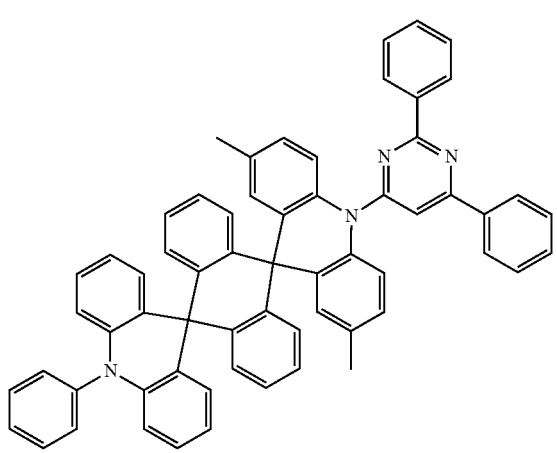
27

28
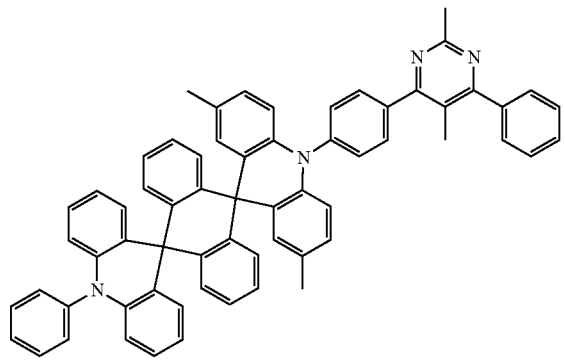
29
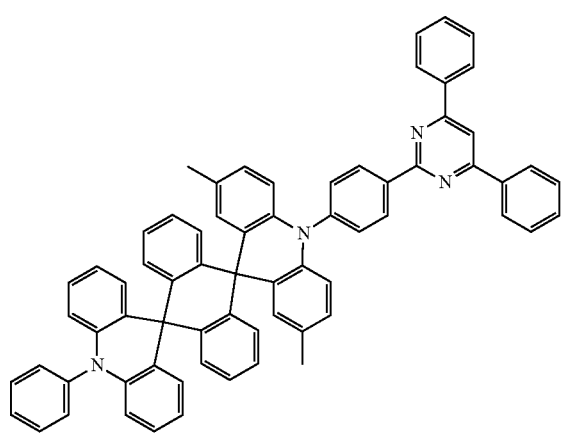
30
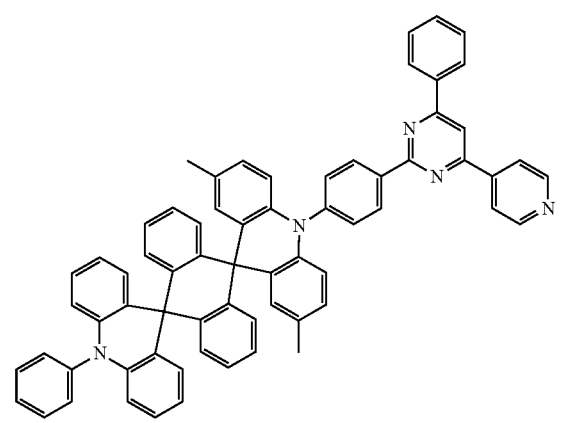
31
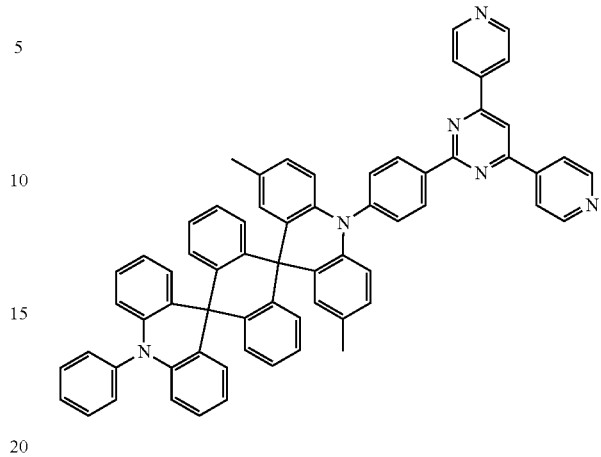
32
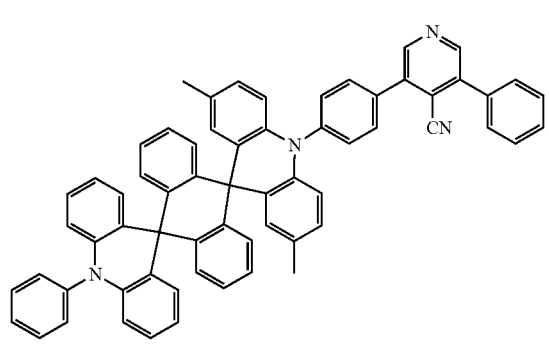
33
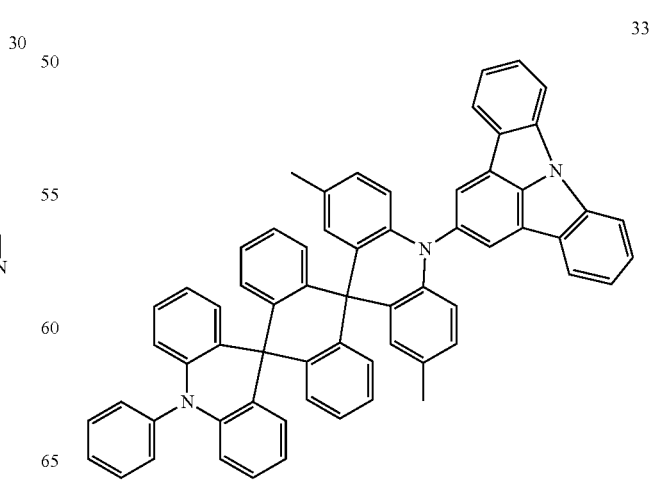

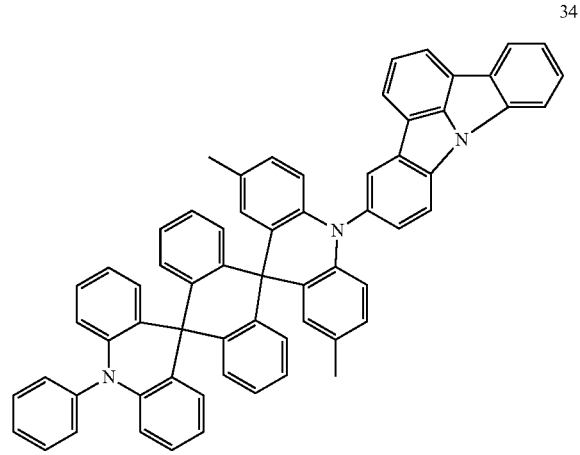
34
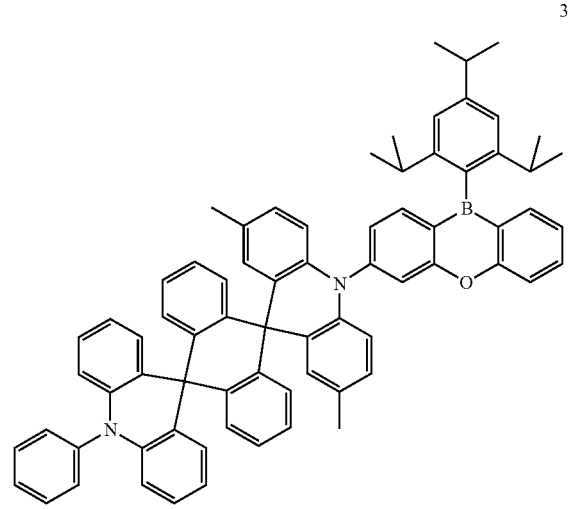
35
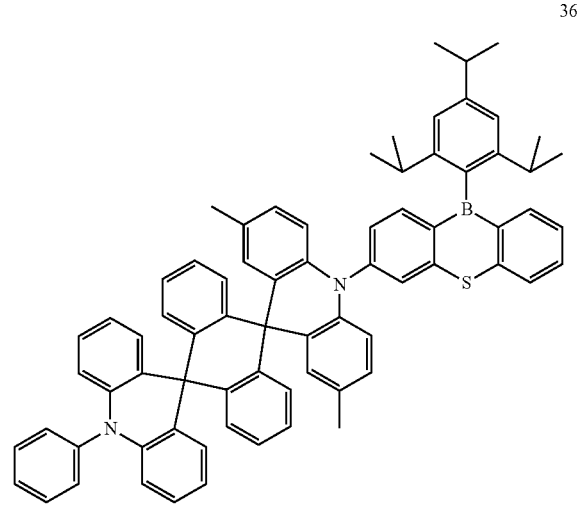
36
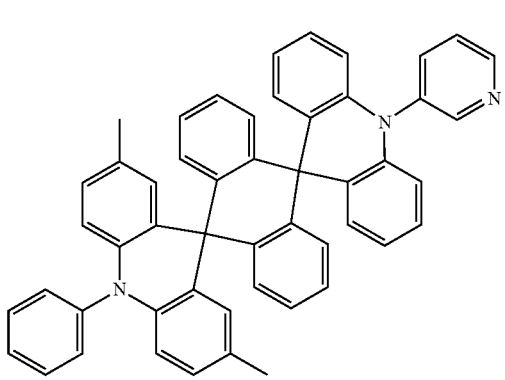
37
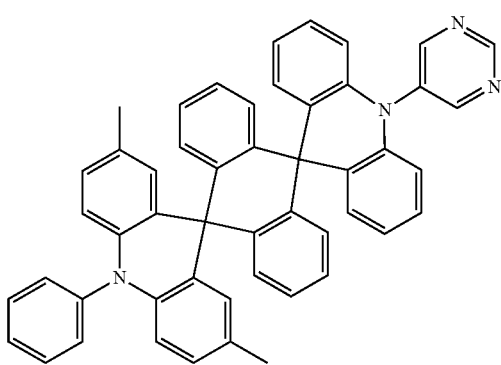
38
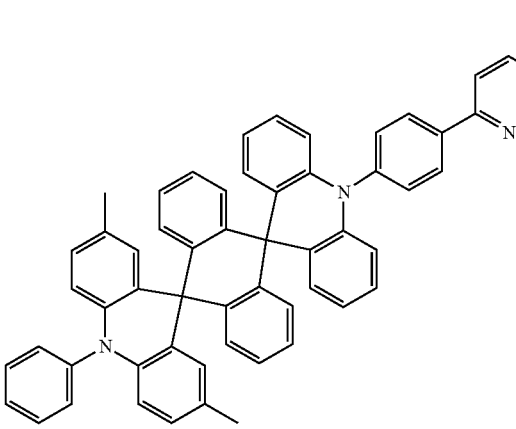
39
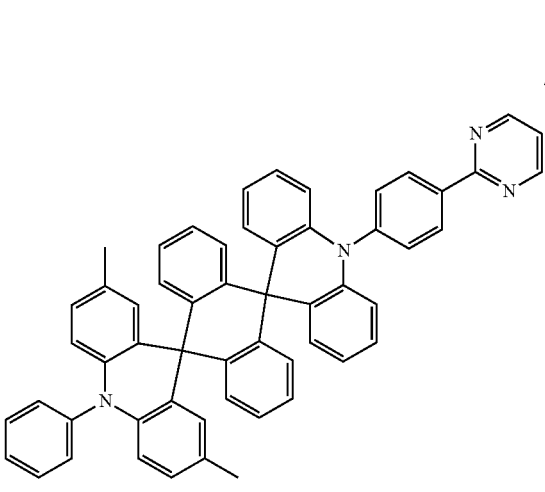
40

41
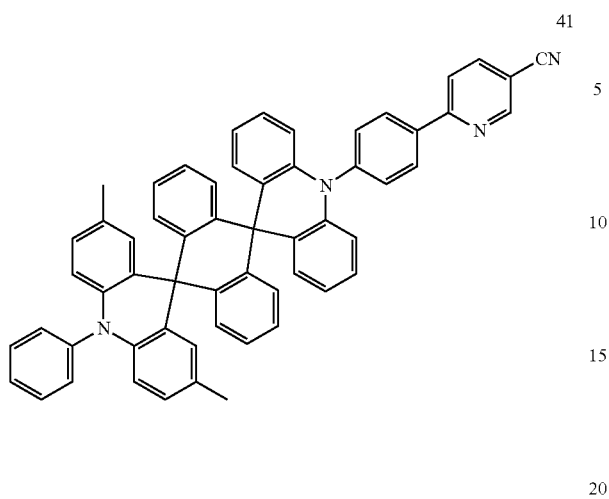
42
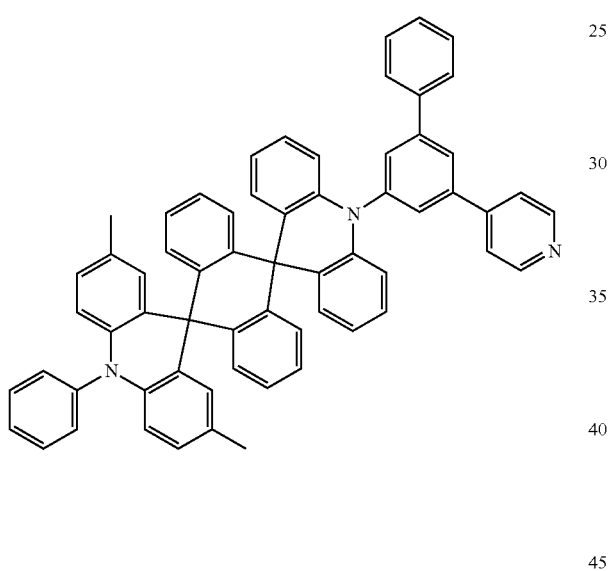
43
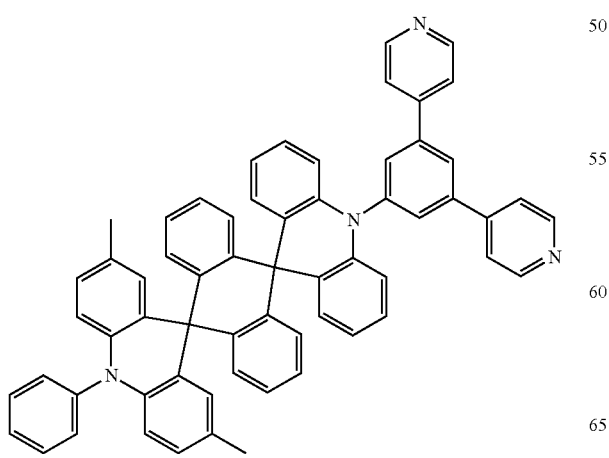
44
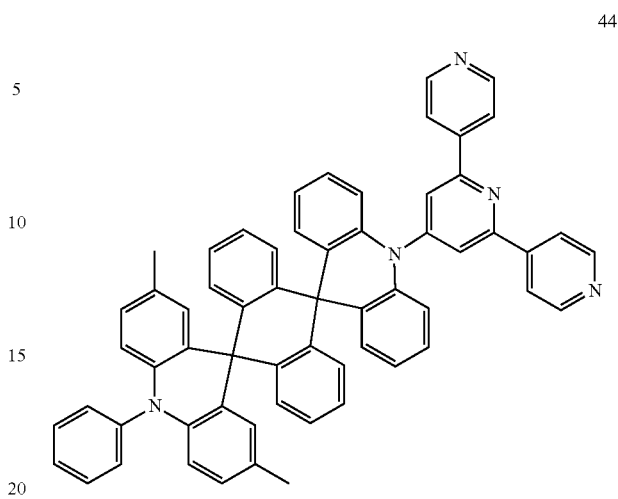
45
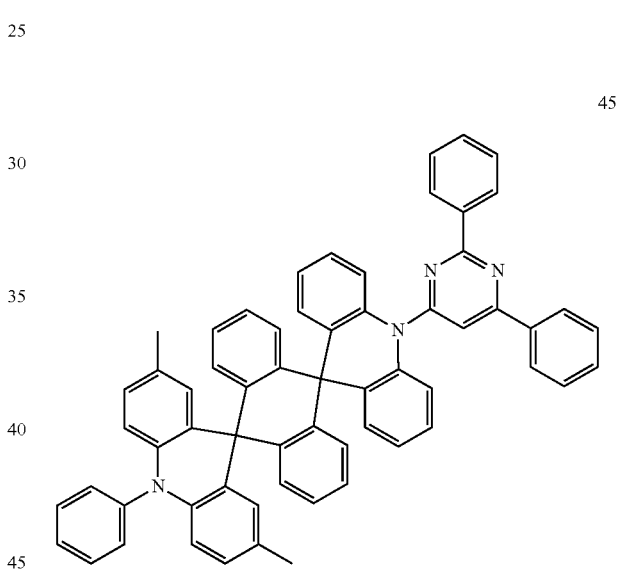
46
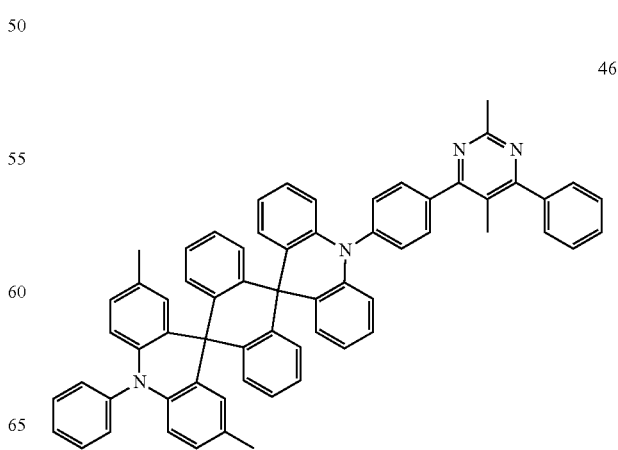

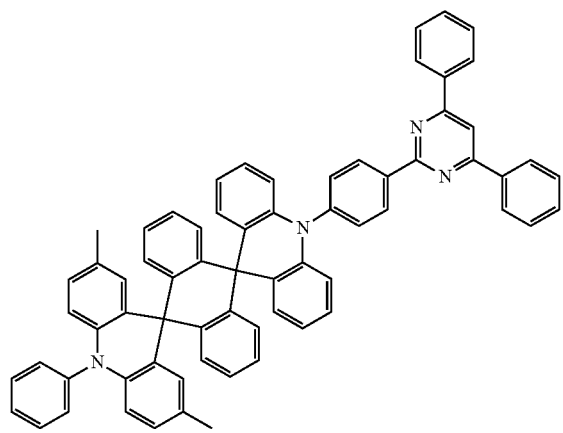
47
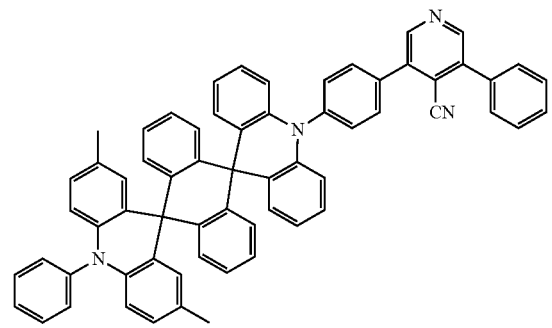
50
48
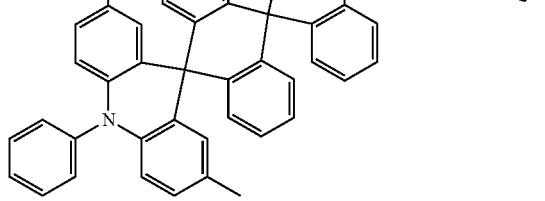
51
49
52
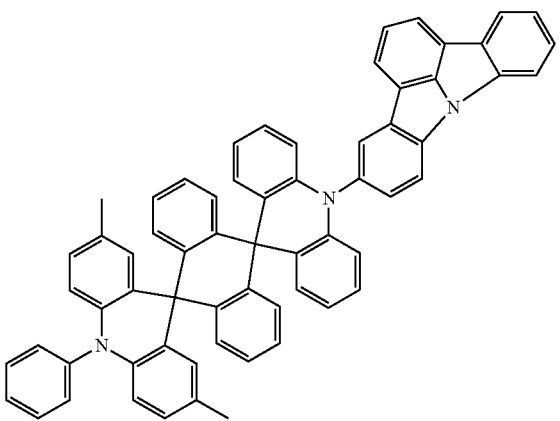

31
-continued
53
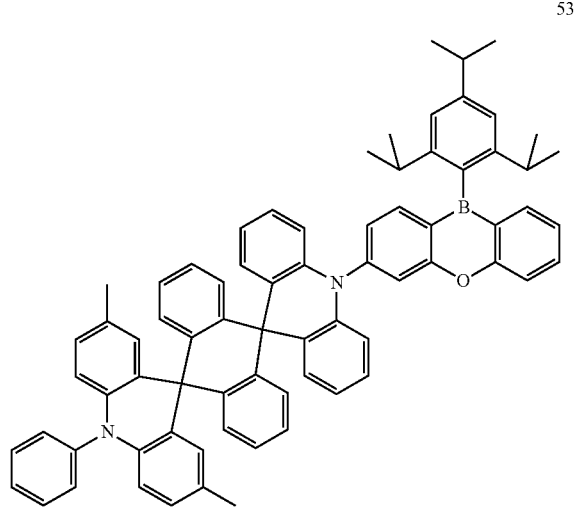
54
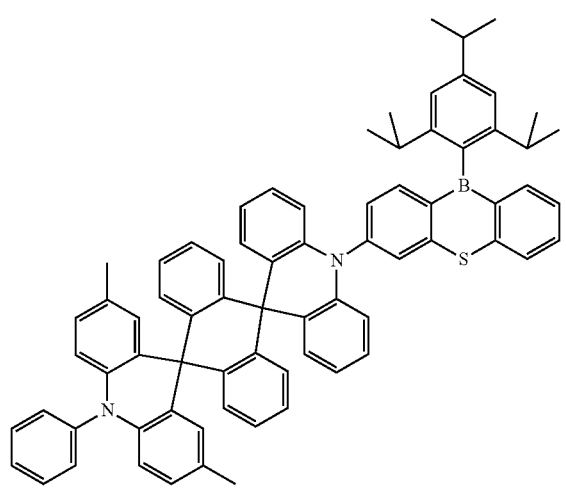
55
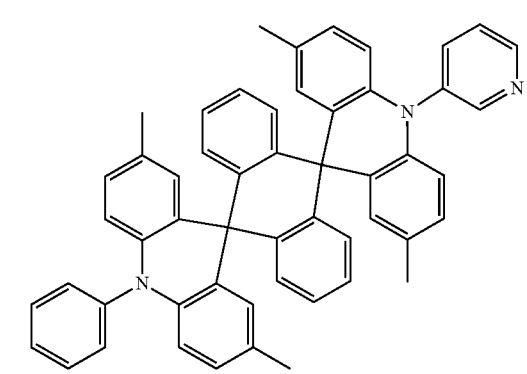
32
-continued
56
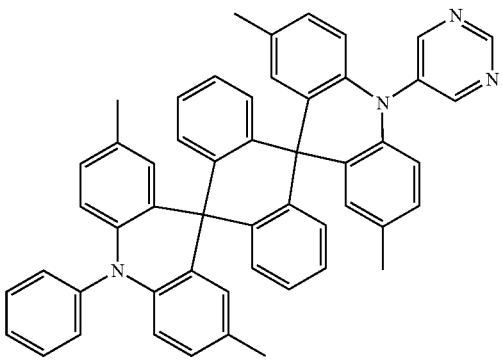
57
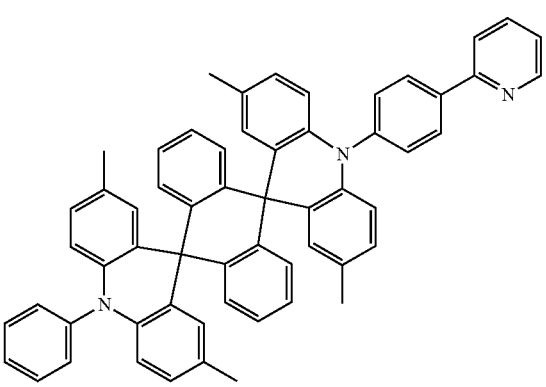
58
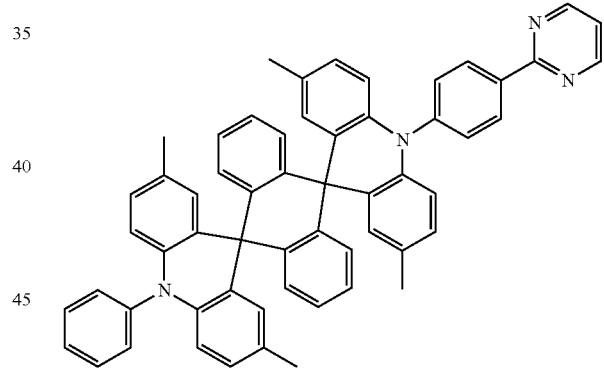
59
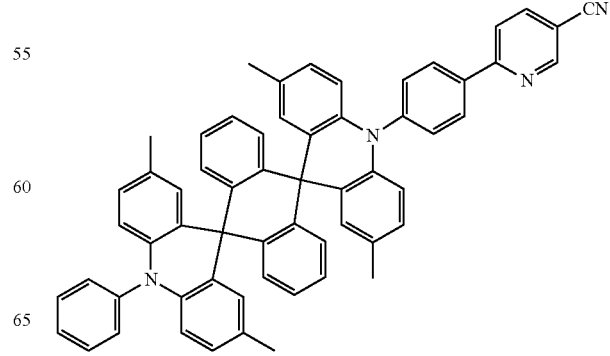

60
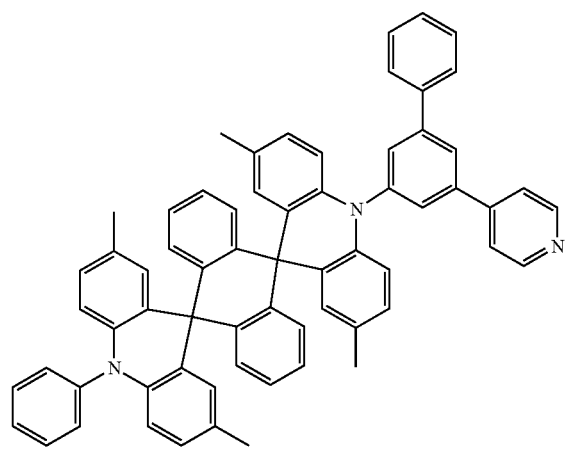
61
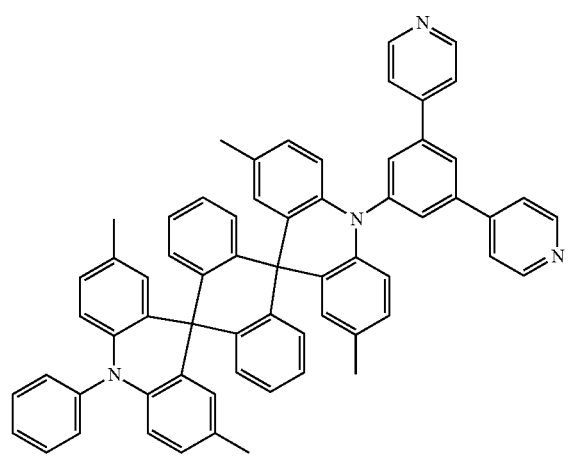
62
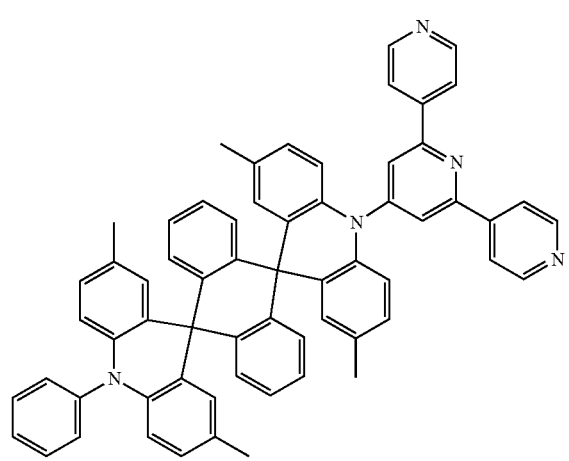
63
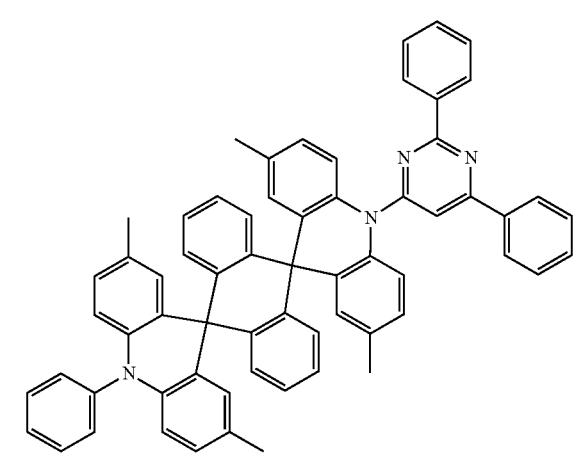
64
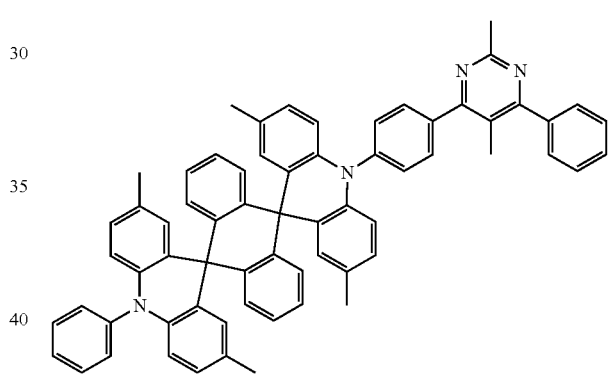
65
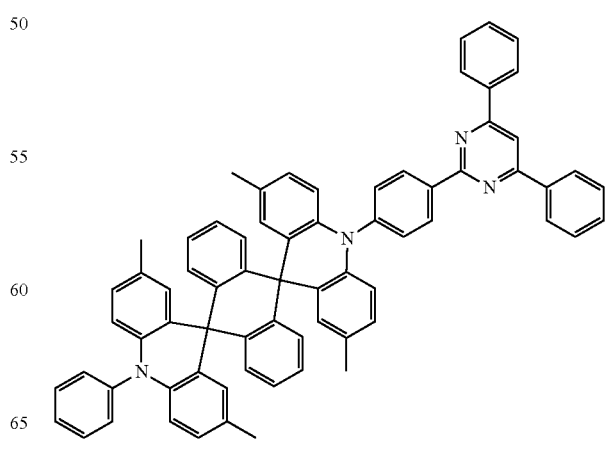

-continued
66
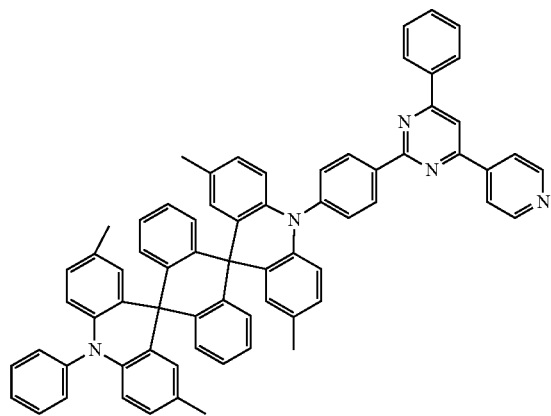
67
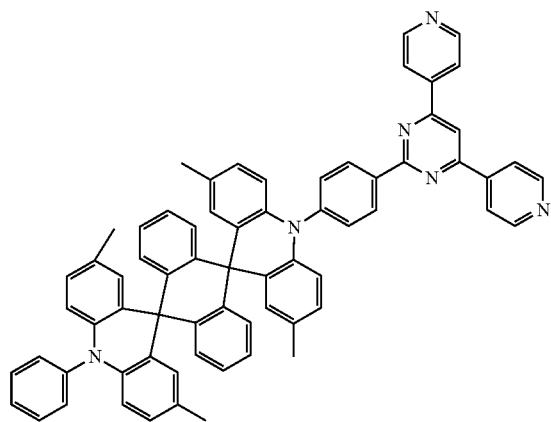
68
-continued
69
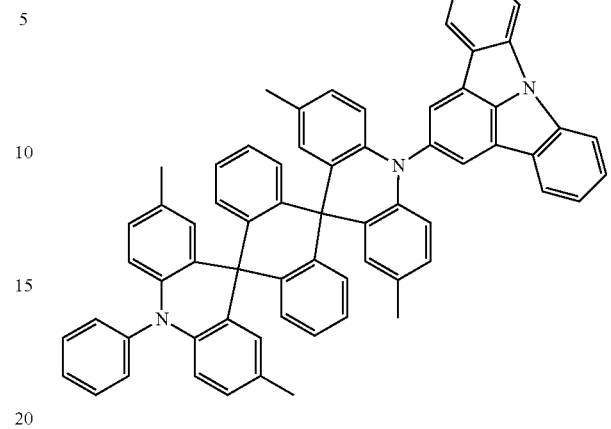
70
71
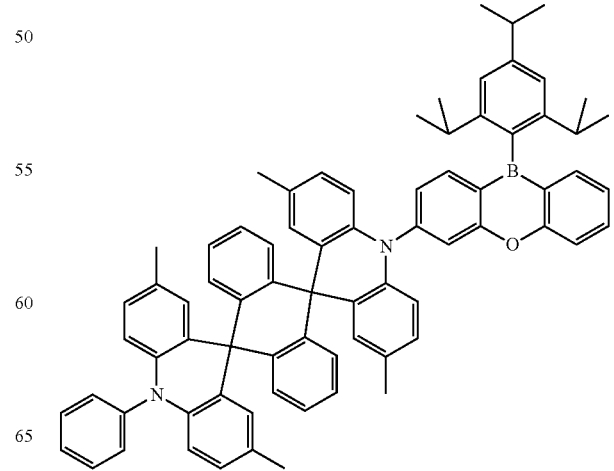

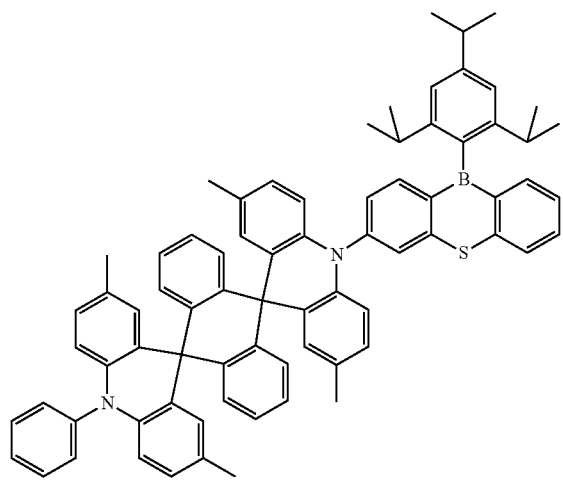
72
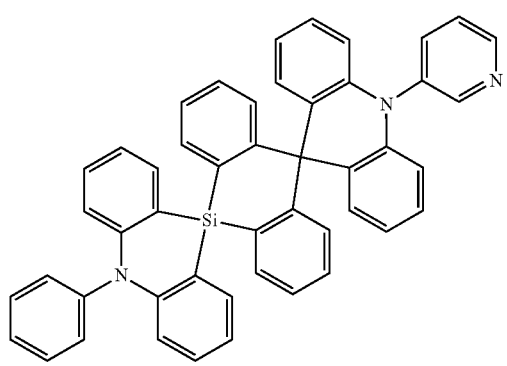
73
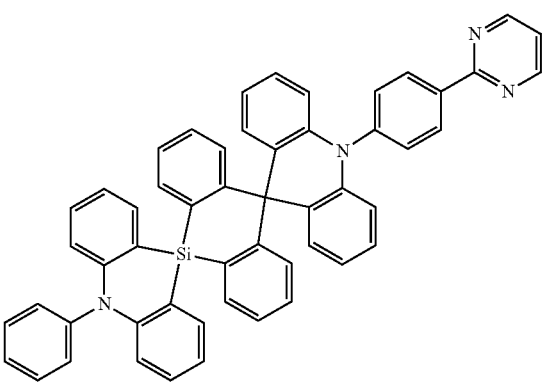
74
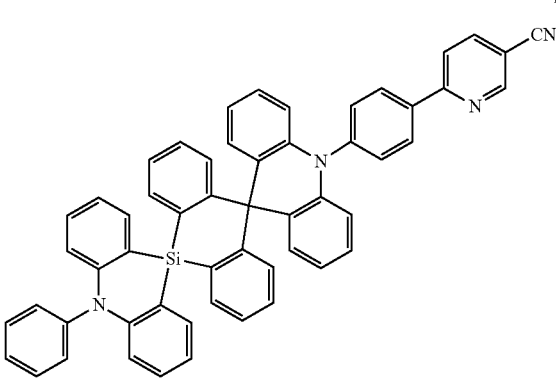
75
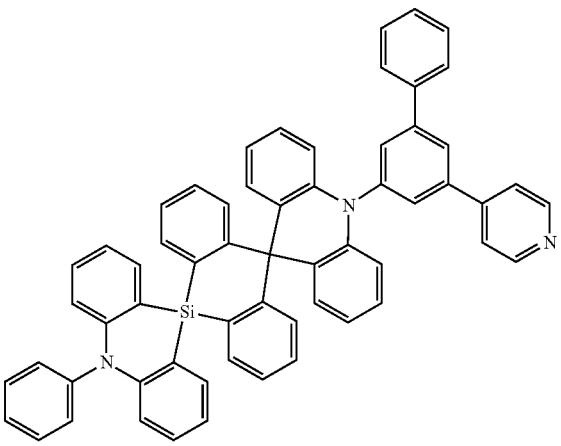
76
77
78

79
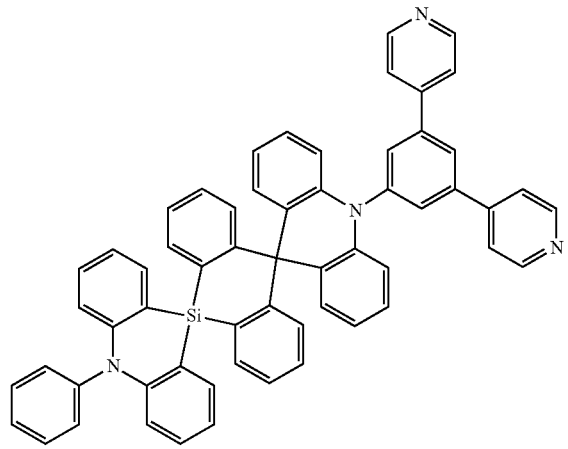
80
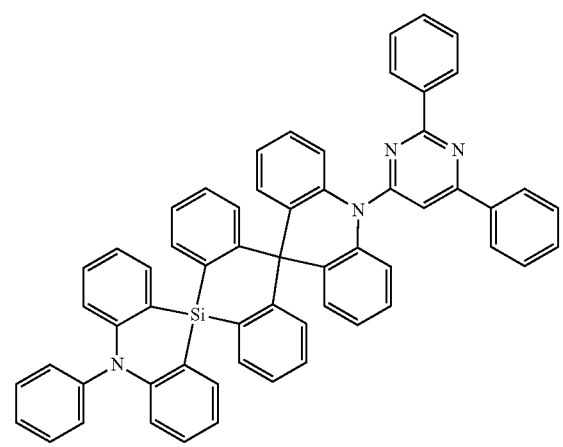
81
82
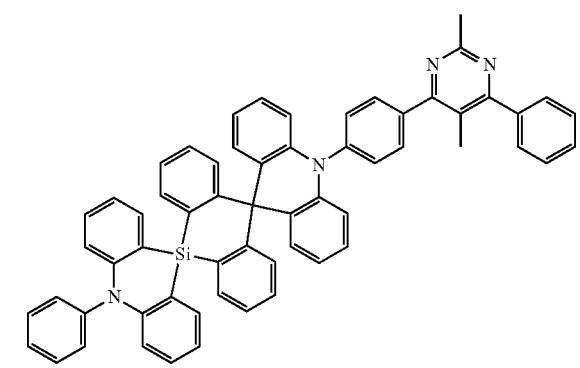
83
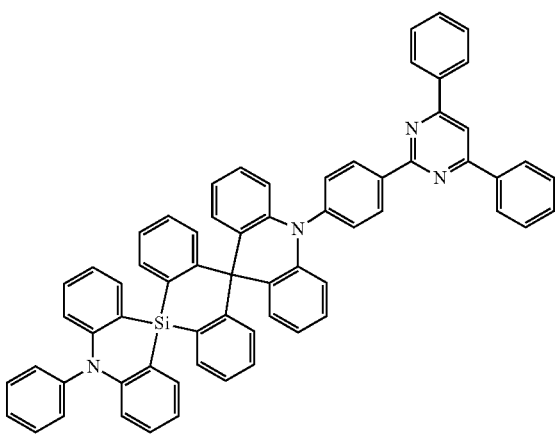
84
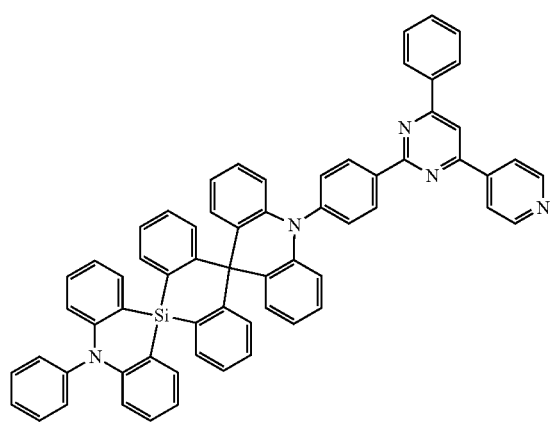

41
-continued

85

86

87

42
-continued

88

89

90

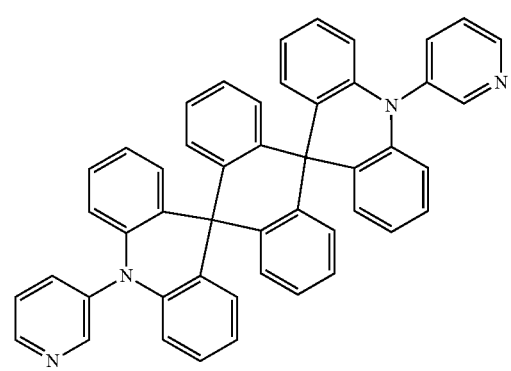
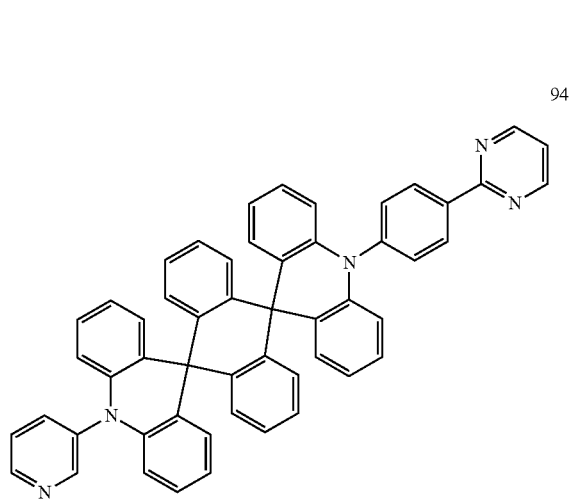
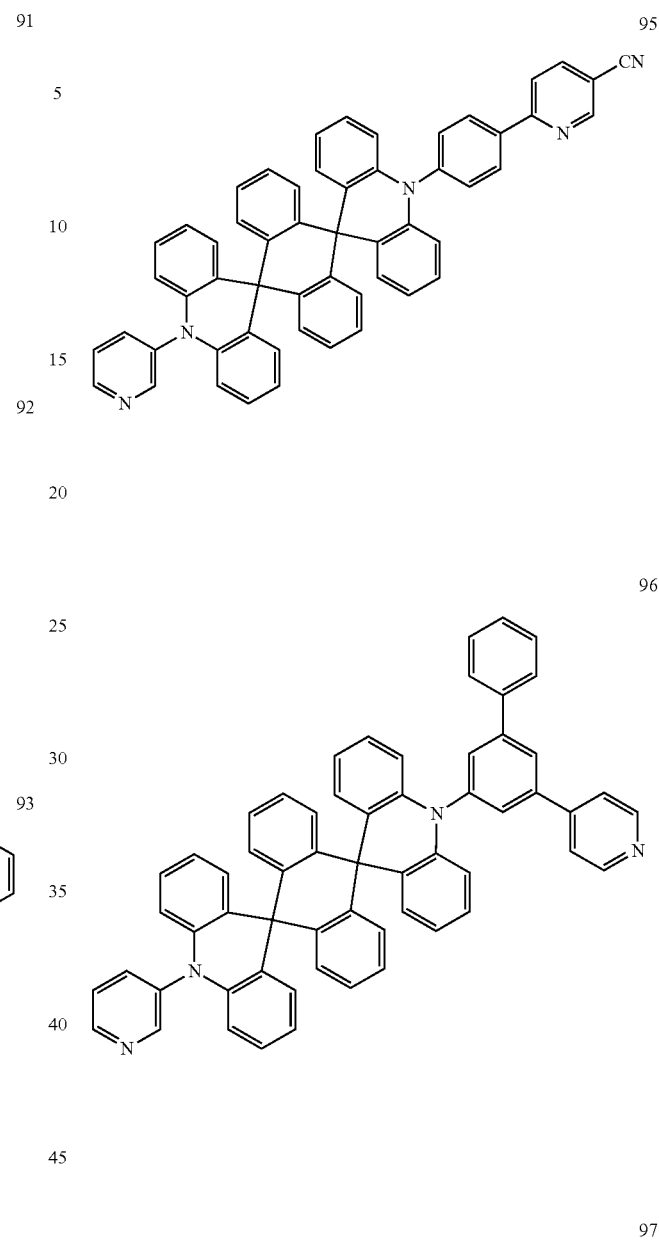

98
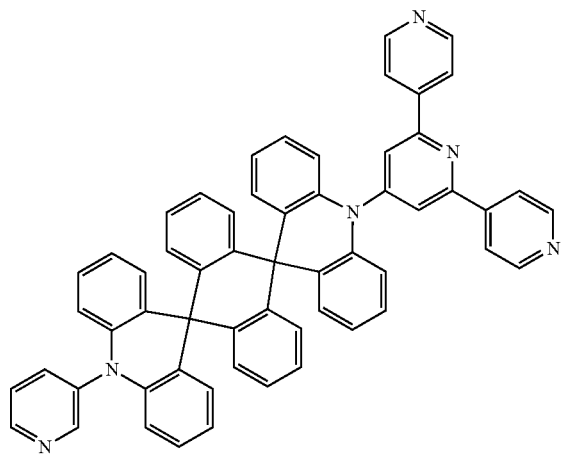
99
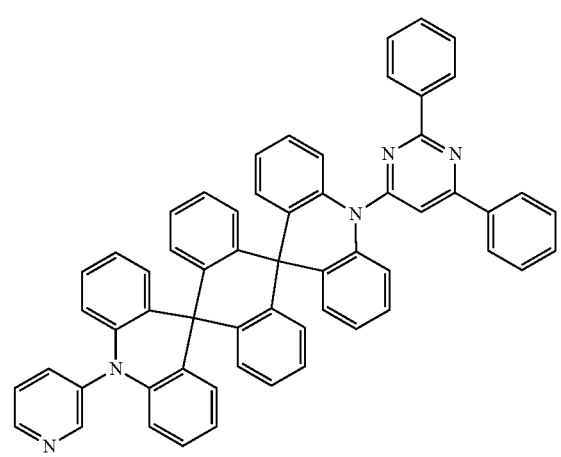
100
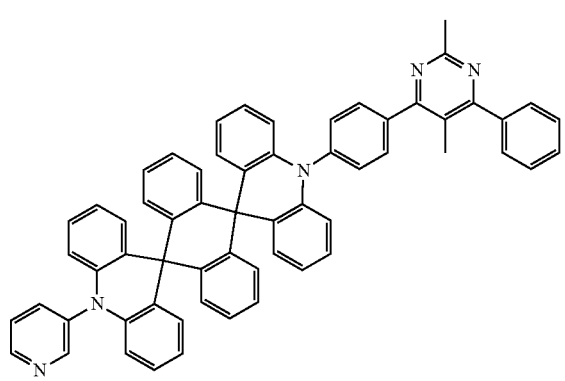
101
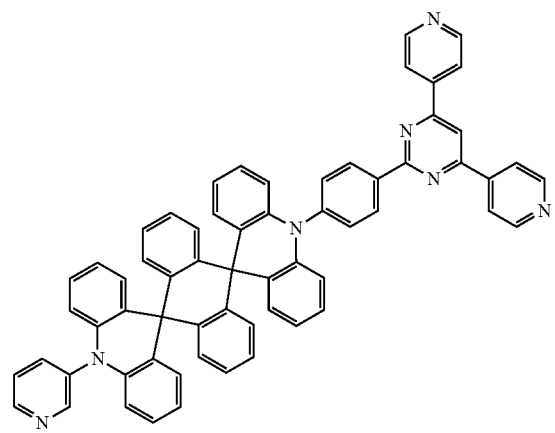
102
103

104
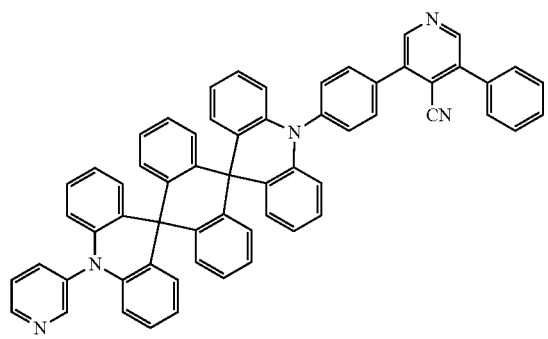
105
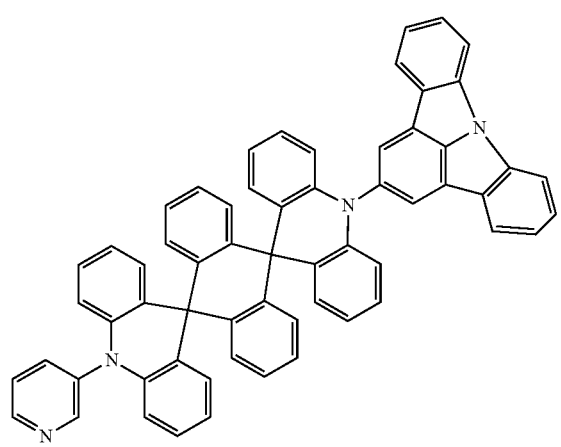
106
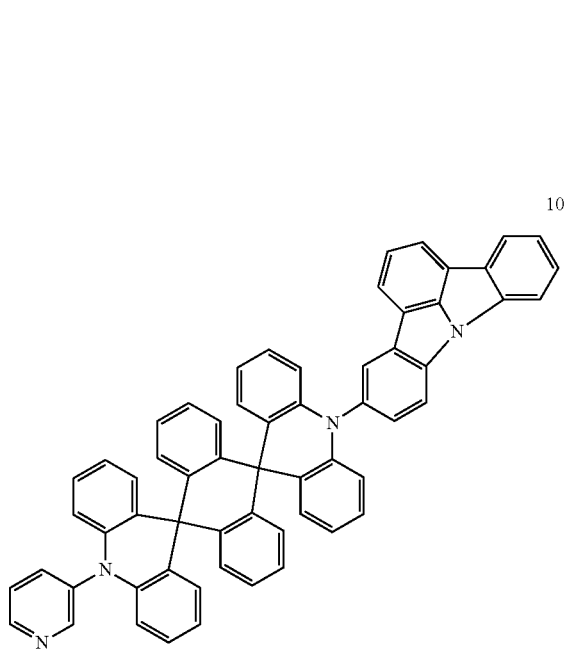
107
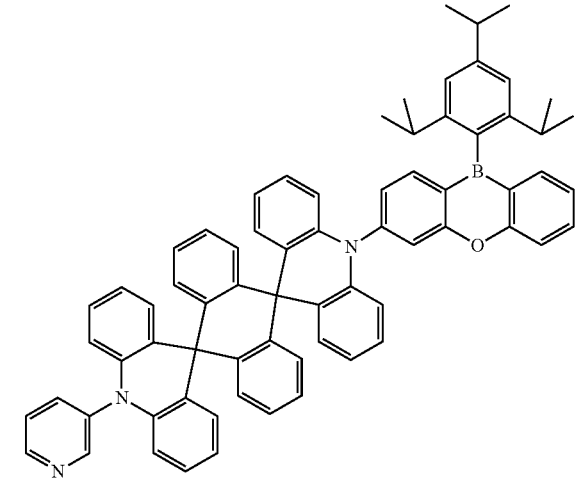
108
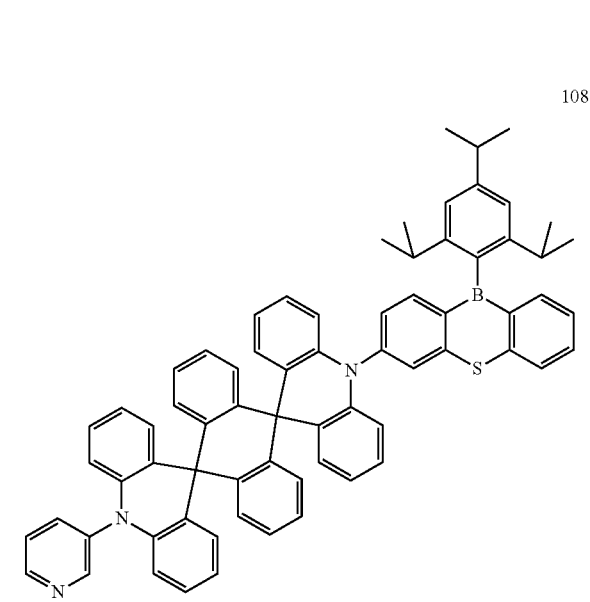
109
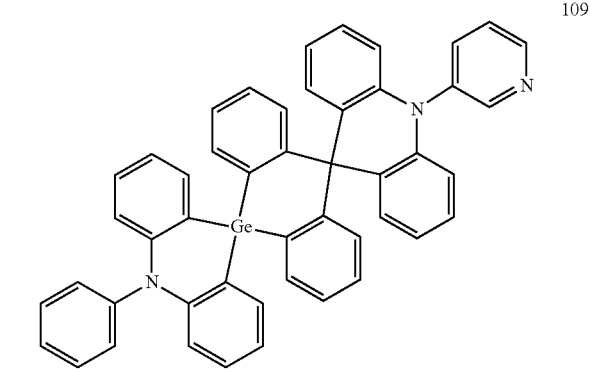

110
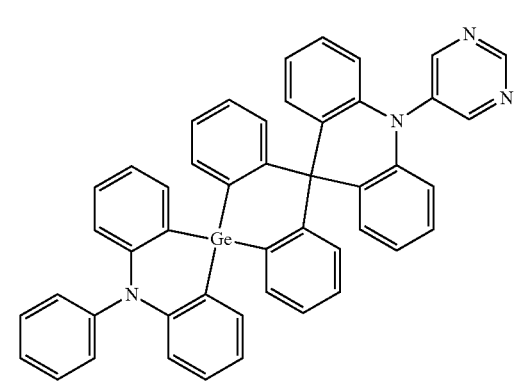
111
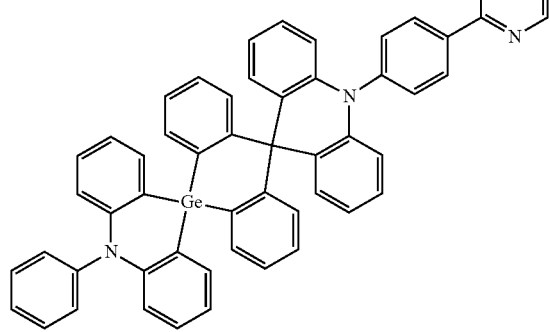
112
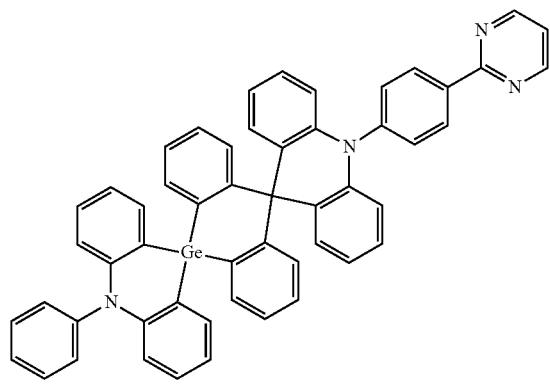
113
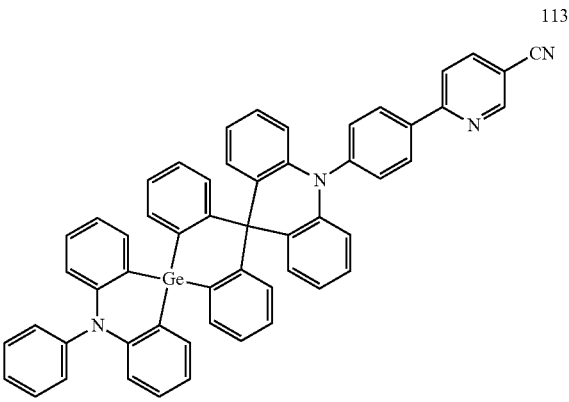
114
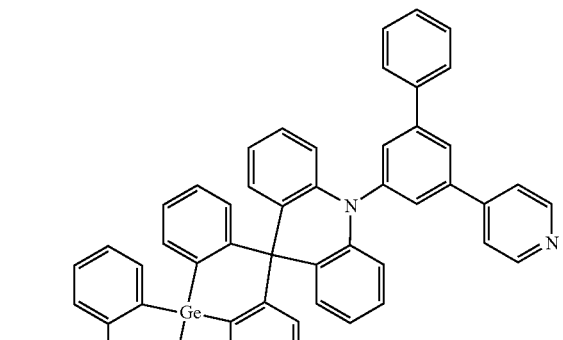
115
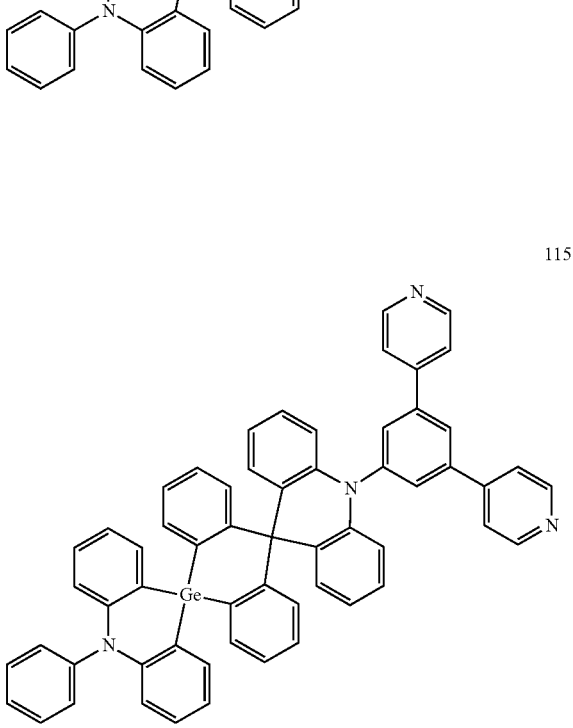
116
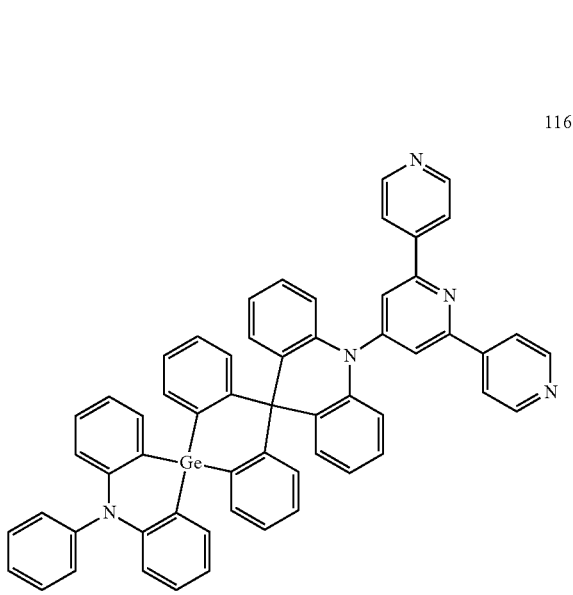

117
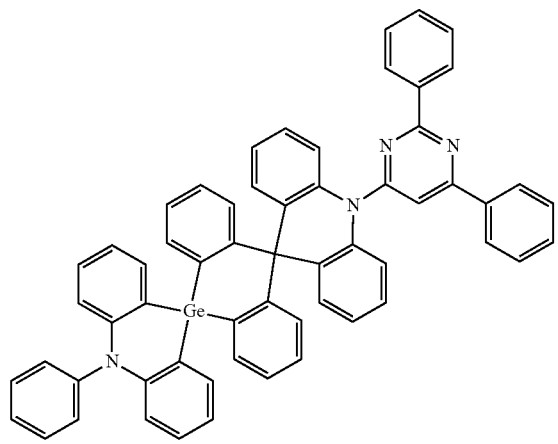
118
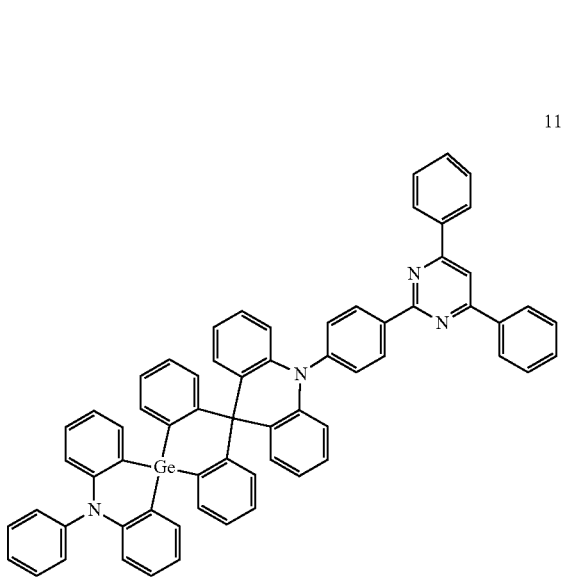
119
120
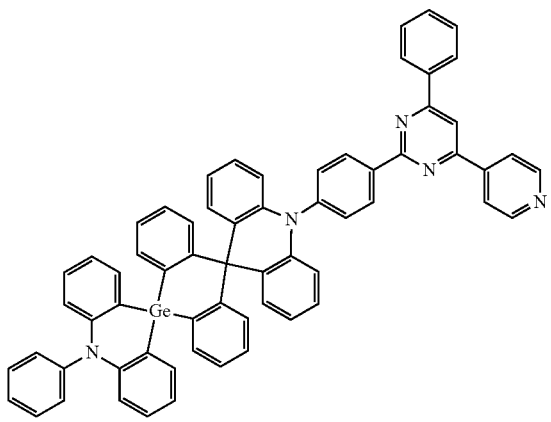
121
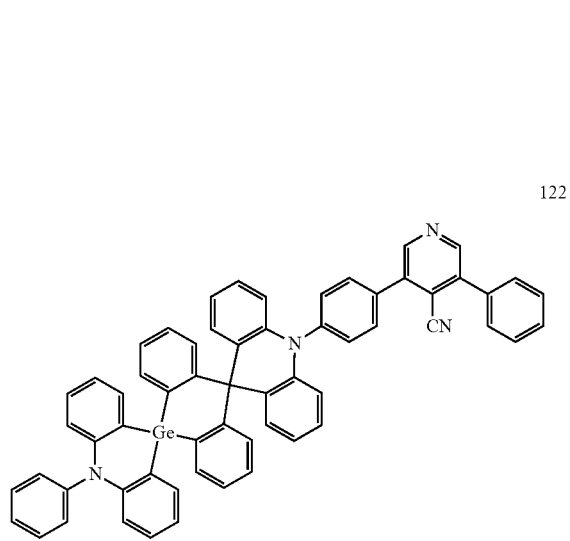
122

123

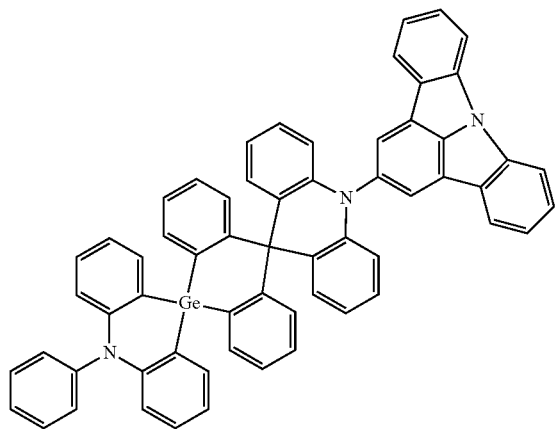

124

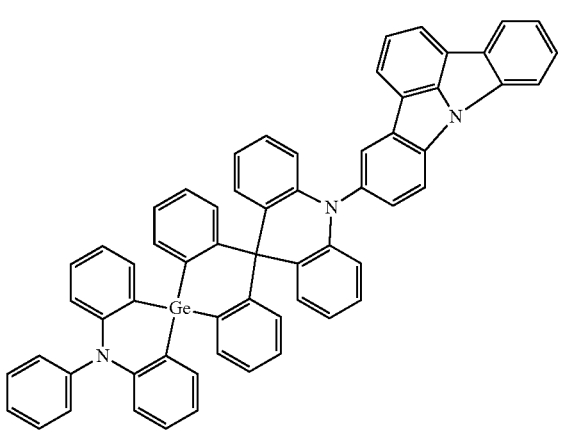

125

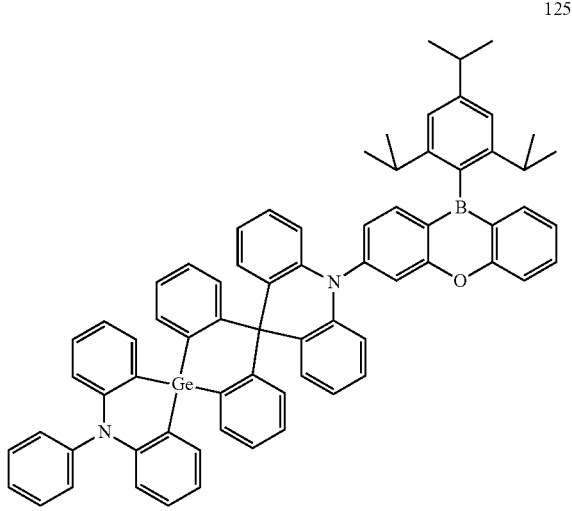

126

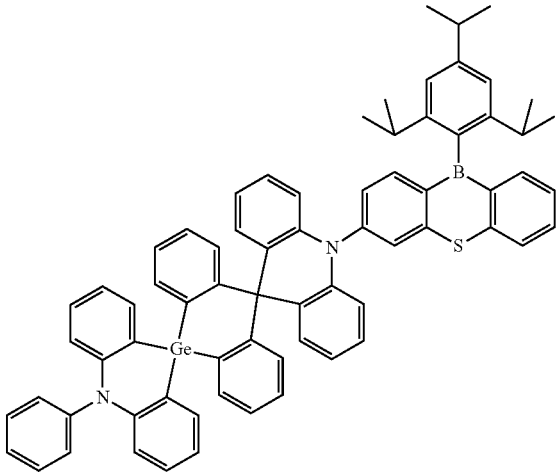

The compound for thermally activated delayed fluorescence according to an embodiment of the present disclosure has a chemical structure represented by Formula 1, and has a molecular aspect ratio of 1.5 or more. In case the compound satisfies the above requirements, it may be used as an emission material for thermally activated delayed fluorescence of an organic electroluminescence device to attain high efficiency, for example, to attain deep blue light emission of high efficiency.

Hereinafter, an organic electroluminescence device according to an embodiment of the present disclosure will be explained in further detail. The explanation will be mainly given with regard to features different from the compound for thermally activated delayed fluorescence according to an embodiment of the present disclosure, and the unexplained parts will follow the above-description on the compound for thermally activated delayed fluorescence according to an embodiment of the present disclosure.

An organic electroluminescence device according to an embodiment of the present disclosure includes the above-described compound for thermally activated delayed fluorescence according to an embodiment of the present disclosure.

Figure 2:
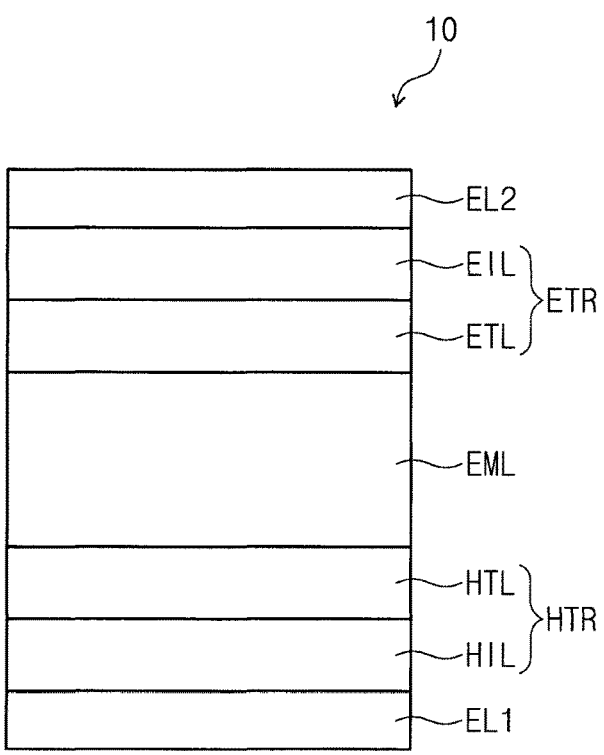
FIG. 2 is a schematic cross-sectional view of an organic electroluminescence device according to an embodiment of the present disclosure.
Figure 3:
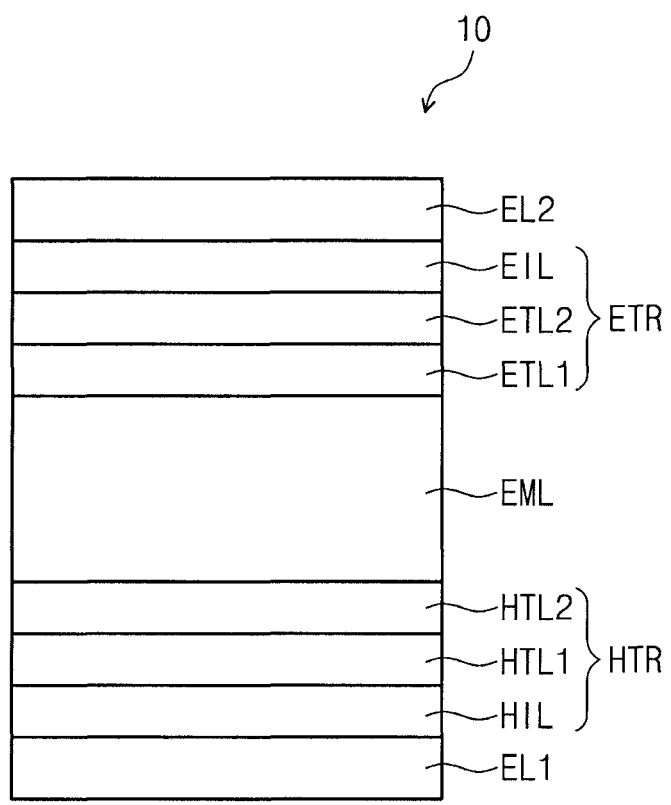
FIG. 3 is a schematic cross-sectional view of an organic electroluminescence device according to an embodiment of the present disclosure.

FIG. 1 is a schematic cross-sectional view illustrating an organic electroluminescence device according to an embodiment of the present disclosure. FIG. 2 is a schematic cross-sectional view illustrating an organic electroluminescence device according to an embodiment of the present disclosure. FIG. 3 is a schematic cross-sectional view illustrating an organic electroluminescence device according to an embodiment of the present disclosure.

Referring to FIGS. 1 to 3, an organic electroluminescence device 10 according to an embodiment of the present disclosure includes a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. In case the first electrode EL1 is the transmissive electrode, the first electrode EL1 may include a transparent metal oxide such as indium tin oxide (ITO), indium zinc oxide (IZO), zinc oxide (ZnO), or indium tin zinc oxide (ITZO). In case the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, or ITZO. For example, the first electrode EL1 may have a trilayer structure of ITO/Ag/ITO. However, an embodiment of the present disclosure is not limited thereto.

The thickness of the first electrode EL1 may be from about 1,000 Å to about 10,000 Å, for example, from about 1,000 Å to about 3,000 Å.

The hole transport region HTR is disposed on the first electrode EL1. The hole transport region HTR may include at least one of a hole injection layer HIL, a hole transport layer HTL, a hole buffer layer, or an electron blocking layer. The thickness of the hole transport region HTR may be from about 1,000 Å to about 1,500 Å, for example.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In addition, the hole transport region HTR may have a single layer structure formed using a plurality of different materials, or a laminated structure of hole injection layer HIL/hole transport layer HTL, hole injection layer HIL/first hole transport layer HTL1/second hole transport layer HTL2, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, laminated in order from the first electrode EL1, without limitation.

The hole transport region HTR may be formed using various suitable methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylam triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB, α-NPD), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, 1,3-bis(N-carbazolyl)benzene (mCP), carbazole derivatives such as N-phenyl carbazole and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4"-tris(N-carbazolyl) triphenylamine (TCTA), N,N'-di(1-naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, for example, from about 100 Å to about 1,000 Å. In case the hole transport region HTR includes both of the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. The hole transport layer HTL may have a single layer structure, or a multilayer structure including the first hole transport layer HTL1 and the second hole transport layer HTL2. In case the thicknesses of the hole transport region HTR, the hole injection layer HIL and the hole transport layer HTL satisfy the above-described ranges, suitable or satisfactory hole transport properties may be obtained without substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. The p-dopant may be one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide and molybdenum oxide, without limitation.

As described above, the hole transport region HTR may further include at least one of a hole buffer layer or an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing or reducing electron injection from the electron transport region ETR into the hole transport region HTR.

The emission layer EML is disposed on the hole transport region HTR. The thickness of the emission layer EML may be, for example, from about 100 Å to about 1,000 Å, or from about 100 Å to about 300 Å. The emission layer EML may have a single layer formed using a single material, a single layer formed using a plurality of different materials, or a multilayer structure having a plurality of layers formed using a plurality of different materials.

Hereinafter, a case where the above-described compound for thermally activated delayed fluorescence according to an embodiment of the present disclosure is included in an emission layer EML, will be explained in more detail. However, an embodiment of the present disclosure is not limited thereto. The compound according to an embodiment of the present disclosure may be included in at least one organic layer provided between the first electrode EL1 and the second electrode EL2. For example, the compound according to an embodiment of the present disclosure may be included in the hole transport region HTR. For example, the compound according to an embodiment of the present disclosure may be included in the hole transport layer HTL. For example, the compound according to an embodiment of the present disclosure may be included in the hole transport layer HTL contacting with the emission layer EML.

The emission layer EML may include the above-described compound for thermally activated delayed fluorescence according to an embodiment of the present disclosure. For example, the emission layer EML may include the compound for thermally activated delayed fluorescence having a molecular aspect ratio of 1.5 or more, represented by the following Formula 1:

Formula 1

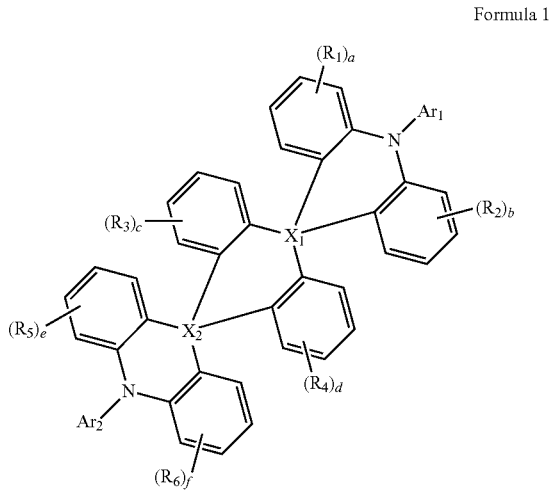

In Formula 1, the definitions of $X_1$, $X_2$, $R_1$ to $R_6$, "a" to "f", $Ar_1$ and $Ar_2$ are the same as described above, and will not be repeated here.

The emission layer EML may include one or more of the compound for thermally activated delayed fluorescence represented by Formula 1. The emission layer EML may further include any suitable material available in the art in addition to the compound for thermally activated delayed fluorescence represented by Formula 1. For example, the emission layer EML may include a fluorescent material including any one selected from the group consisting of spiro-DPVBi, 2,2',7,7'-tetrakis(biphenyl-4-yl)-9,9'-spirobifluorene(spirosexiphenyl) (spiro-6P), distyryl-benzene (DSB), distyrylarylene (DSA), polyfluorene (PFO)-based polymer and poly (p-phenylene vinylene) (PPV)-based polymer. However, an embodiment of the present disclosure is not limited thereto.

The emission layer EML may emit thermally activated delayed fluorescence by including the compound for thermally activated delayed fluorescence represented by Formula 1 as an emission material. The emission layer EML may include a host and a dopant, and the dopant may include the compound for thermally activated delayed fluorescence represented by Formula 1. However, an embodiment of the present disclosure is not limited thereto.

The compound for thermally activated delayed fluorescence represented by Formula 1 may be a thermally activated delayed fluorescence material emitting blue light. For example, the compound may emit blue light having a wavelength range of about 470 nm or shorter. For example, the compound may emit deep blue light having a wavelength range of about 440 nm to about 470 nm, or about 450 nm to about 465 nm.

As described above, the compound for thermally activated delayed fluorescence according to an embodiment of the present disclosure may have an absolute value of the difference between the singlet energy level and the triplet energy level of about 0.2 eV or less.

The emission layer may further include a host, as described above. The host may be any suitable material available in the art without specific limitation and may include, for example, tris(8-hydroxyquinolino)aluminum (Alq3), 4,4'-bis(N-carbazolyl)-1,1'-biphenyl (CBP), poly(N-vinylcarbazole) (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetrasiloxane ($DPSiO_4$), 2,8-bis(diphenylphosphoryl)dibenzofuran (PPF), etc.

The electron transport region ETR is provided on the emission layer EML. The electron transport region ETR may include at least one of a hole blocking layer, an electron transport layer ETL or an electron injection layer EIL, without limitation.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure having a plurality of different materials, or a laminated structure of electron transport layer ETL/electron injection layer EIL, first electron transport layer ETL1/second electron transport layer ETL2/electron injection layer EIL, or hole blocking layer/ electron transport layer ETL/electron injection layer EIL, laminated in order from the emission layer EML, without limitation. The thickness of the electron transport region ETR may be, for example, from about 1,000 Å to about 1,500 Å.

The electron transport region ETR may be formed using various suitable methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include bis[2-(diphenylphosphino)phenyl]ether oxide (DPEPO), tris(8-hydroxyquinolinato)aluminum (Alq3), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl) anthracene (ADN), or a mixture thereof, without limitation.

The thickness of the electron transport layer ETL may be from about 100 Å to about 1,000 Å, for example, from about 150 Å to about 500 Å. The electron transport layer ETL may have a single layer structure, or a multilayer structure including the first electron transport layer ETL1 and the second electron transport layer ETL2. If the thickness of the electron transport layer ETL satisfies the above-described range, suitable or satisfactory electron transport properties may be obtained without substantial increase of a driving voltage.

When the electron transport region ETR includes the electron injection layer EIL, the electron transport region ETR may use LiF, lithium quinolate (LiQ), $Li_2O$, BaO, NaCl, CsF, a metal in lanthanides such as Yb, or metal halides such as RbCl and RbI, without limitation. The electron injection layer EIL also may be formed using a mixture material of an electron transport material and an insulating organo metal salt. The organo metal salt may be a material having an energy band gap of about 4 eV or more. For example, the organo metal salt may include, for example, a metal acetate, a metal benzoate, a metal acetoacetate, a metal acetylacetonate, or a metal stearate. The thickness of the electron injection layer EIL may be from about 1 A to about 100 Å, for example, from about 3 Å to about 90 Å. In case the thickness of the electron injection layer EIL satisfies the above described range, suitable or satisfactory electron injection properties may be obtained without substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen), without limitation.

The second electrode EL2 is disposed on the electron transport region ETR. The second electrode EL2 may be a common electrode or a cathode. The second electrode EL2 may be a transmissive electrode, a transflective electrode or a reflective electrode. In case the second electrode EL2 is the transmissive electrode, the second electrode EL2 may be formed using transparent metal oxides, for example, ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayer structure including a reflective layer or a transflective layer formed using the above-described materials and a transparent conductive layer formed using ITO, IZO, ZnO, ITZO, etc.

The second electrode EL2 may be coupled or connected with an auxiliary electrode. In case the second electrode EL2 is coupled or connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type (or kind), the first electrode EL1 may be a reflective electrode, and the second electrode EL2 may be a transmissive electrode or a transflective electrode. In case the organic electroluminescence device 10 is a bottom emission type (or kind), the first electrode EL1 may be a transmissive electrode or a transflective electrode, and the second electrode EL2 may be a reflective electrode.

The organic electroluminescence device according to an embodiment of the present disclosure includes the compound for thermally activated delayed fluorescence having a molecular aspect ratio of 1.5 or more, represented by Formula 1, thereby securing high efficiency.

Hereinafter, embodiments of the subject matter of the present disclosure will be explained in more detail with reference to embodiments and comparative embodiments. The following embodiments are illustrated only for assisting the understanding of the subject matter of the present disclosure, and the scope of the present disclosure is not limited thereto.

SYNTHESIS EXAMPLES

The compounds for thermally activated delayed fluorescence according to an embodiment of the present disclosure may be synthesized, for example, as follows. However, the synthetic method of the compounds for thermally activated delayed fluorescence according to an embodiment of the present disclosure is not limited thereto.

1. Synthesis of Compound 20

Compound 20, the compound for thermally activated delayed fluorescence according to an embodiment of the present disclosure, may be synthesized, for example, by the following reaction.

(Synthesis of Compound C)

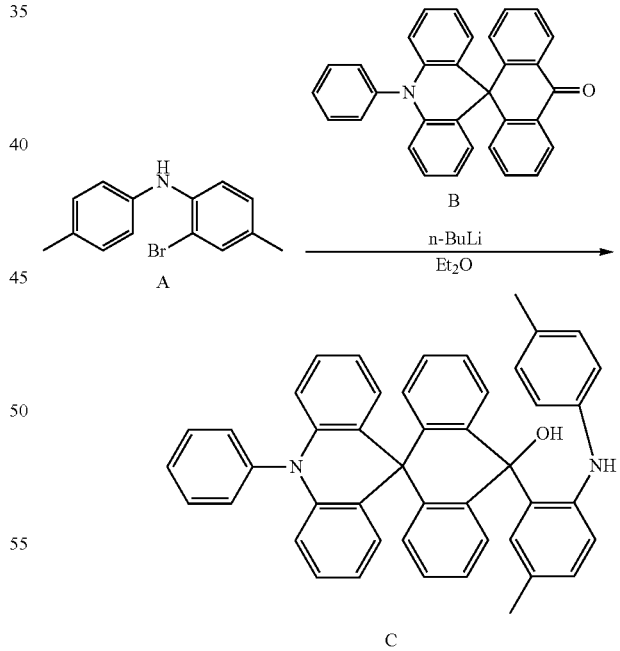

Under an argon (Ar) atmosphere, 2.0 g of Compound A and 30 mL of dehydrated diethyl ether were injected to a 200 mL three neck flask, and 11 mL of 1.6 M n-BuLi was added thereto dropwise at room temperature. After stirring at room temperature for about 2 hours, Compound B dissolved in 20 mL of dehydrated diethyl ether was added thereto dropwise, and the mixture was further stirred. After the completion of reaction, water was added to the reactant, and an organic layer was separated and solvents were evaporated. The crude product thus obtained was purified by silica gel column chromatography (toluene) to obtain 4.35 g (yield 95%) of a white solid compound.

The molecular weight of the white solid compound measured by fast atom bombardment-mass spectrometry (FAB-MS) was 632. From the results, the white solid compound was identified as Compound C.

(Synthesis of Intermediate compound D)

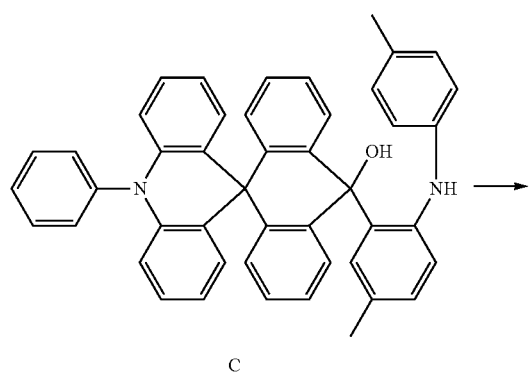

C

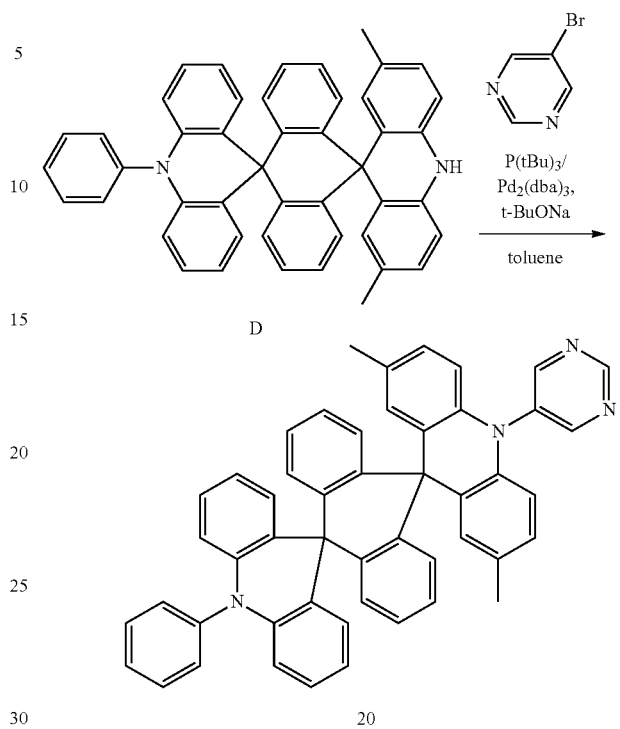

D

Under an argon (Ar) atmosphere, 4.0 g of Compound C and 20 mL of toluene were injected to a 100 mL three neck flask, and 0.73 g of methylsulfonic acid and 1.0 g of polyphosphoric acid were added thereto. The mixture was stirred and heated to reflux for about 4 hours. After the completion of reaction, water was added to the reactant, and an organic layer was separated and solvents were evaporated. The crude product thus obtained was purified by silica gel column chromatography (toluene) to obtain 3.9 g (yield 90%) of a white solid compound.

The molecular weight of the white solid compound measured by FAB-MS was 614. From the results, the white solid compound was identified as Compound D.

(Synthesis of Compound 20)

D

20

Under an argon (Ar) atmosphere, 2.0 g of Compound D, 0.52 g of 5-bromopyrimidine, 0.63 g of sodium tert-butoxide, 0.21 g of tris(dibenzylideneacetone)dipalladium(0), 0.09 g of tri-tert-butylphosphine, and 40 mL of xylene were injected to a 100 mL three neck flask, and the mixture was stirred and heated to reflux for about 8 hours. After the completion of reaction, water was added to the reactant, and an organic layer was separated and solvents were evaporated. The crude product thus obtained was purified by silica gel column chromatography (mixture of toluene and hexane) to obtain 1.4 g (yield 61° A) of a white solid compound.

The molecular weight of the white solid compound measured by FAB-MS was 692. From the results, the white solid compound was identified as Compound 20.

2. Synthesis of Compound 22

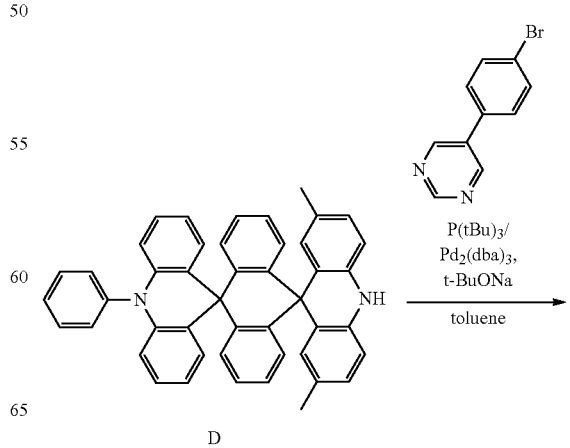

D

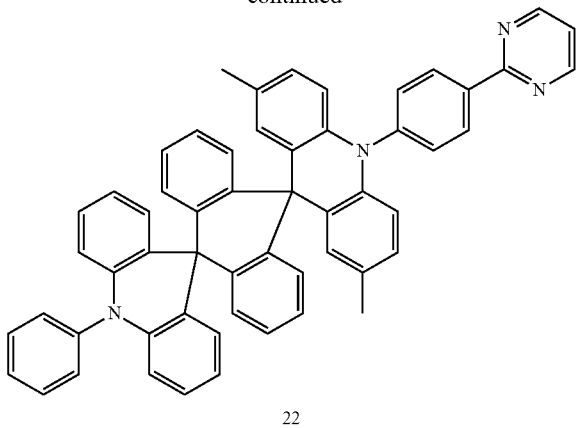

22

Compound 22 was synthesized by conducting substantially the same synthetic method of Compound 20 except for using 2-(4-bromophenyl)pyrimidine instead of 5-bromopyrimidine in the synthetic method of Compound 20 (yield 65%).

The molecular weight of Compound 22 measured by FAB-MS was 768.

3. Synthesis of Compound 33 using 2-bromoindolo[3,2,1-jk]carbazole instead of 5-bromopyrimidine in the synthetic method of Compound 20 (yield 58%).

The molecular weight of Compound 33 measured by FAB-MS was 854.

4. Synthesis of Compound 17

(Synthesis of Compound F)

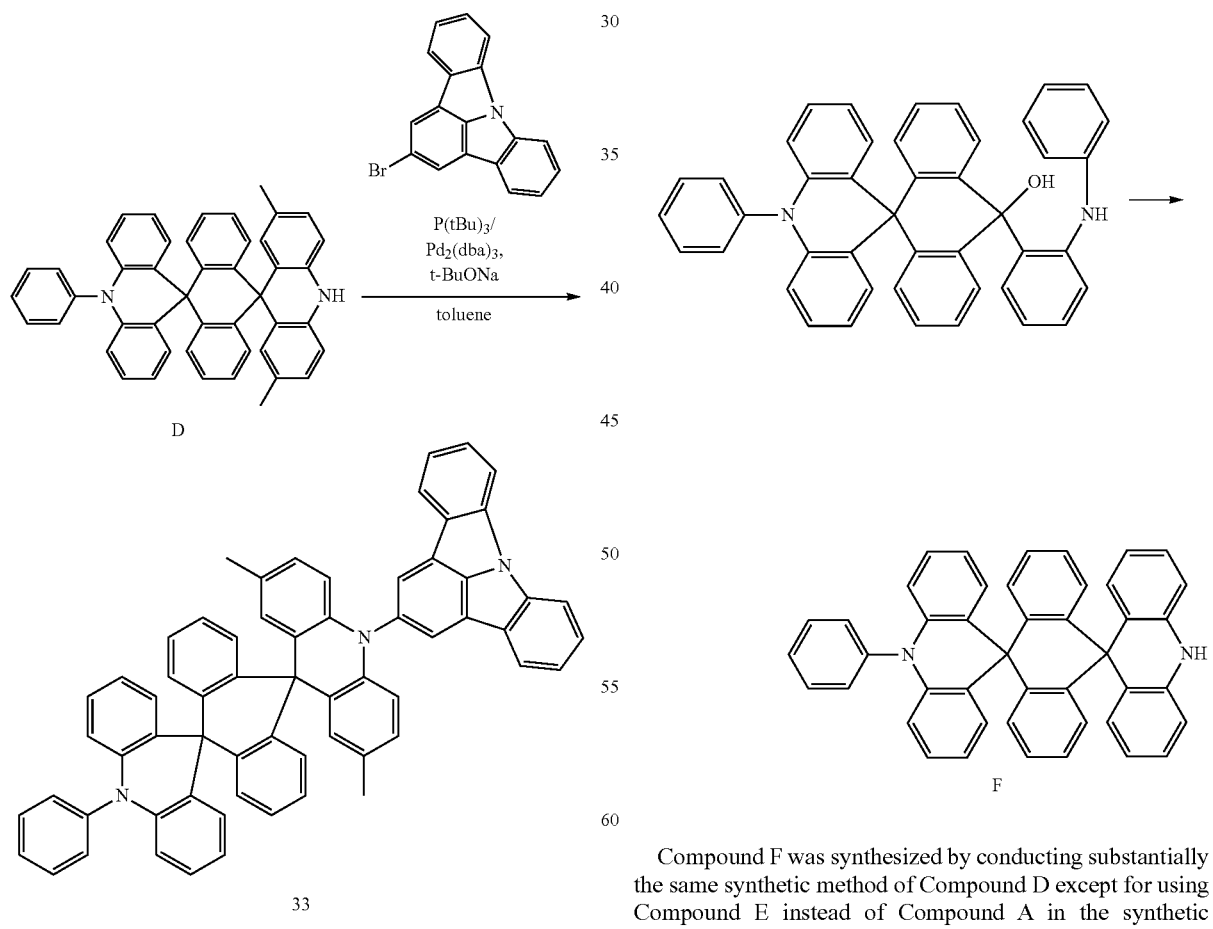

Compound F was synthesized by conducting substantially the same synthetic method of Compound D except for using Compound E instead of Compound A in the synthetic method of Compound D (yield 92%).

The molecular weight of Compound F measured by FAB-MS was 586.

Compound 33 was synthesized by conducting substantially the same synthetic method of Compound 20 except for (Synthesis of Compound 17)

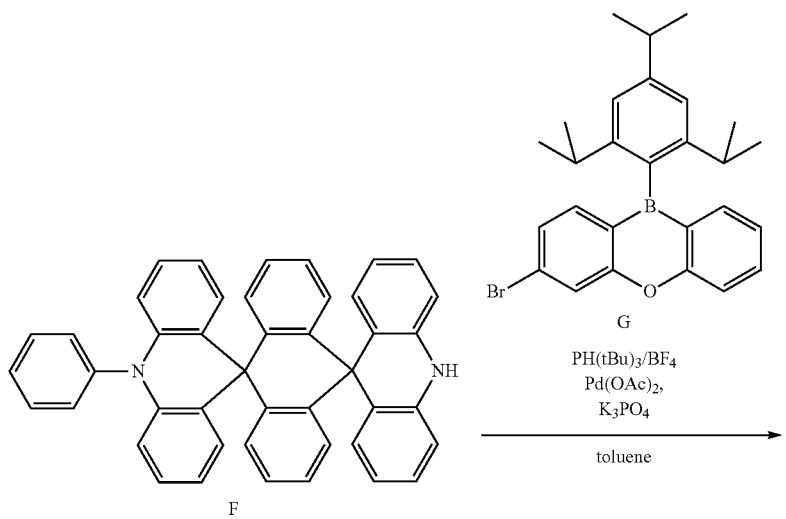

Under an argon (Ar) atmosphere, 2.0 g of Compound F, 1.57 g of Compound G, 1.45 g of tripotassium phosphate, 0.02 g of palladium(II) acetate, 0.08 g of tri-tert-butylphosphonium tetrafluoroborate, and 30 mL of xylene were injected to a 100 mL three neck flask, and the mixture was stirred and heated to reflux for about 6 hours. After the completion of reaction, water was added to the reactant, and an organic layer was separated and solvents were evaporated. The crude product thus obtained was purified by silica gel column chromatography (mixture of toluene/hexane) to obtain 1.65 g (yield 50%) of Compound 17 as a white solid.

The molecular weight of Compound 17 measured by FAB-MS was 967.

5. Synthesis of Compound 74
(Synthesis of Compound I)

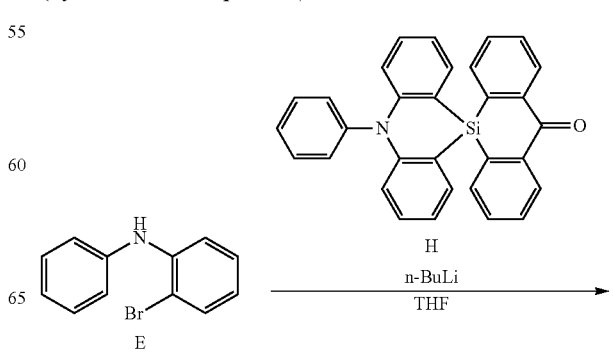

6. Synthesis of Compound 110

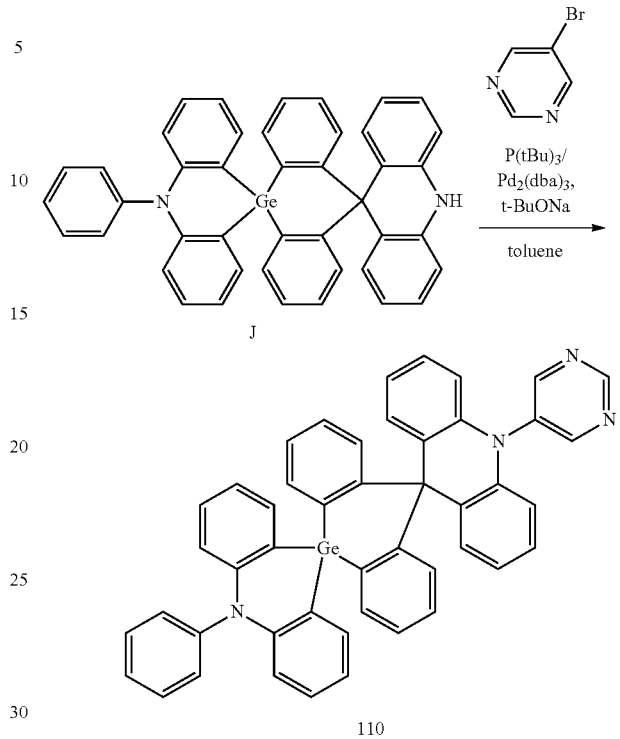

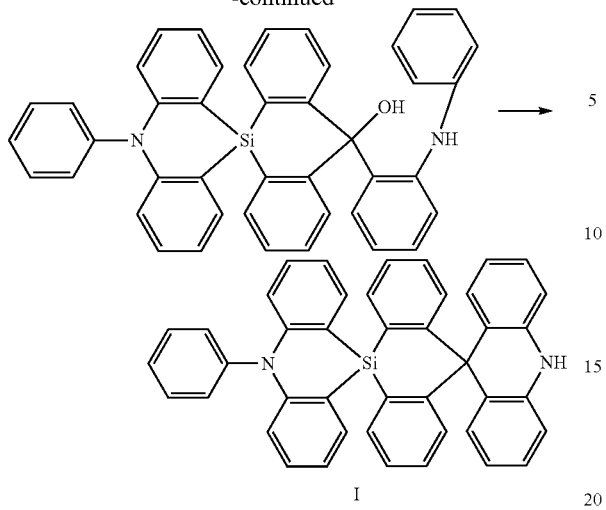

Compound I was synthesized by conducting substantially the same synthetic method of Compound F except for using Compound H instead of Compound B in the synthetic method of Compound F (yield 92%).

The molecular weight of Compound I measured by FAB-MS was 602.

(Synthesis of Compound 74)

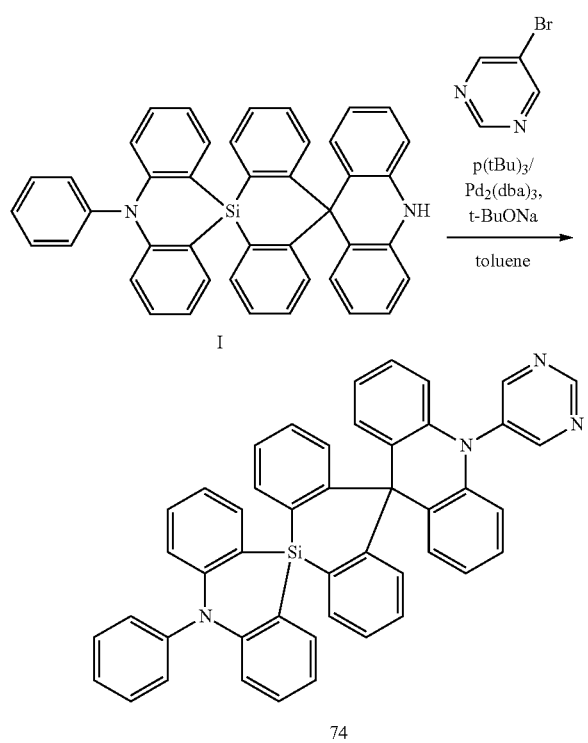

Compound 74 was synthesized by conducting substantially the same synthetic method of Compound 20 except for using Compound I instead of Compound D in the synthetic method of Compound 20 (yield 65%).

The molecular weight of Compound 74 measured by FAB-MS was 680.

Compound 110 was synthesized by conducting substantially the same synthetic method of Compound 74 except for using Compound J instead of Compound I in the synthetic method of Compound 74 (yield 60%).

The molecular weight of Compound 110 measured by FAB-MS was 726.

EXPERIMENTAL EXAMPLE

S1 energy level and T1 energy level of Example Compounds 20, 22, 33 and 17 and Comparative Compounds X1 to X5 were calculated by a nonempirical molecular orbital method. Specifically, the calculation was made using the Gaussian 09 (Gaussian, Inc.) program using B3LYP as the functional, and 6-31G(d) as the basis function. For the optimized structure by the calculation, an aspect ratio (ratio (L/D) of length (L) and diameter (D) of a cylinder having a lower or minimum diameter with a molecule inscribed) was also obtained.

[Example Compounds]

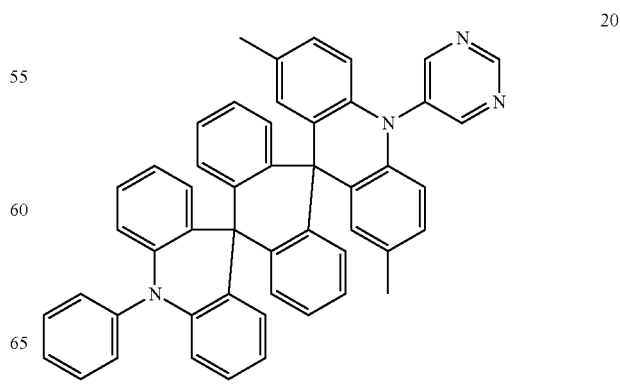

22
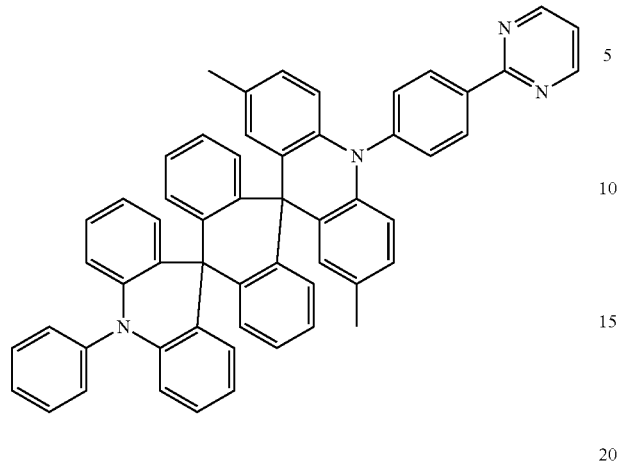
[Comparative Compounds]
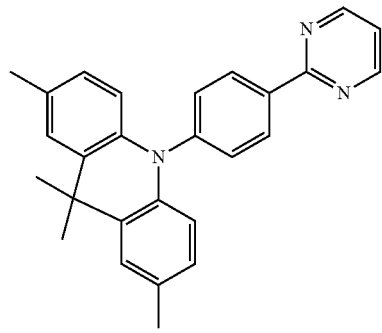
X-1
33
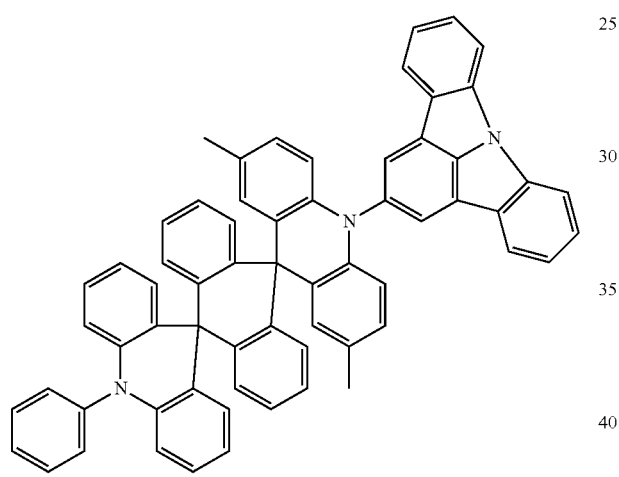
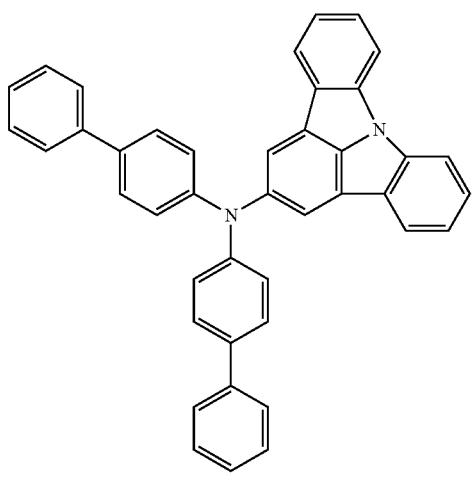
X-2
17
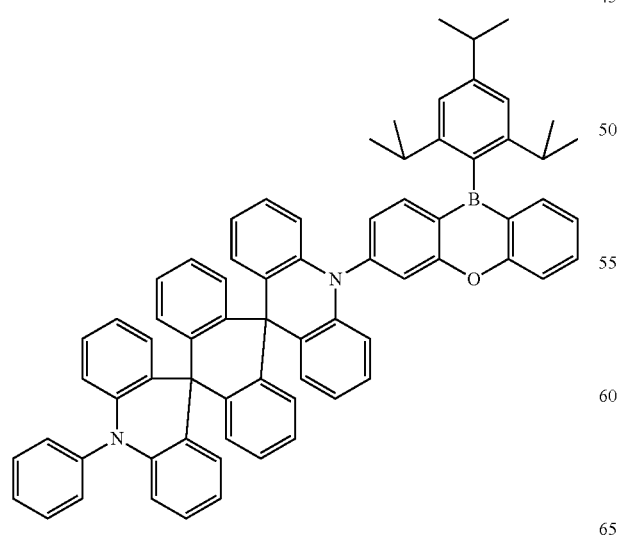
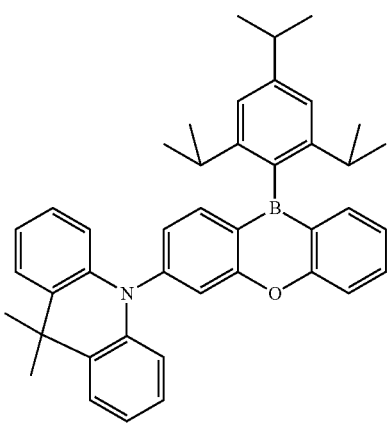
X-3

-continued

X-4

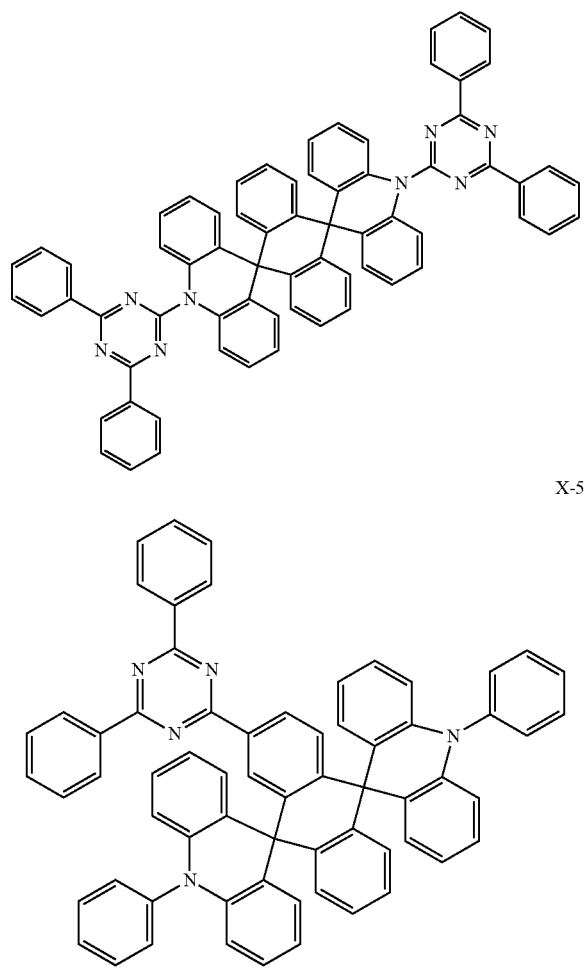

X-5

TABLE 1

| | S1 energy level | T1 energy level | $E_{ST}$ | Aspect ratio |
|---|---|---|---|---|
| Example Compound 20 | 2.91 | 2.82 | 0.09 | 1.6 |
| Example Compound 22 | 2.58 | 2.57 | 0.01 | 2.1 |
| Example Compound 33 | 2.68 | 2.65 | 0.03 | 2.0 |
| Example Compound 17 | 2.61 | 2.60 | 0.01 | 2.1 |
| Comparative Compound X-1 | 2.49 | 2.48 | 0.01 | 1.2 |
| Comparative Compound X-2 | 2.84 | 2.54 | 0.30 | 1.1 |
| Comparative Compound X-3 | 2.53 | 2.52 | 0.01 | 1.4 |
| Comparative Compound X-4 | 3.42 | 3.14 | 0.28 | 1.9 |
| Comparative Compound X-5 | 2.84 | 2.80 | 0.04 | 1.2 |

In Table 1, $E_{ST}$ is a value of the difference between the singlet energy level and the triplet energy level. The unit of S1 and T1 energy level is eV.

All the example compounds have an $E_{ST}$ value of 0.2 or less, which shows that they may be used as materials for thermally activated delayed fluorescence. Comparative Compounds X-1, X-3 and X-5 are also considered to be available as materials for thermally activated delayed fluorescence since they have an $E_{ST}$ value of 0.2 or less. Meanwhile, the $E_{ST}$ value of Comparative Compounds X-2 and X-4 exceeds the generally accepted upper limit of 0.2 for emitting thermally activated delayed fluorescence, and they are not suitable to be used as materials for thermally activated delayed fluorescence. While all the Example Compounds have an aspect ratio of 1.5 or more, Comparative Compounds X-1 to X-3 and X-5 have an aspect ratio of less than 1.5. Meanwhile, Comparative Compound X-4 has an aspect ratio of 1.5 or more.

DEVICE MANUFACTURING EXAMPLE

Organic electroluminescence devices of Examples 1 to 4 and Comparative Examples 1 to 5 were manufactured by using Example Compounds 20, 22, 33 and 17 and Comparative Compounds X-1 to X5 as emission layer materials.

The organic electroluminescence devices according to Examples 1 to 4 and Comparative Examples 1 to 5 were manufactured by forming a first electrode using ITO to a thickness of about 150 nm, a hole injection layer using HAT-CN to a thickness of about 10 nm, a first hole transport layer using α-NPD to a thickness of about 80 nm, a second hole transport layer using mCP to a thickness of about 5 nm, an emission layer using (bis{2-[di(phenyl)phosphino]phenyl}ether oxide (DPEPO) doped with the example compounds or the comparative compounds in an amount of 18% to a thickness of about 20 nm, a first electron transport layer using DPEPO to a thickness of about 10 nm, a second electron transport layer using TPBi to a thickness of about 30 nm, an electron injection layer using LiF to a thickness of about 0.5 nm, and a second electrode using Al to a thickness of about 100 nm. Each layer was formed by a vacuum deposition method.

TABLE 2

| | Emission layer | λmax (nm) | ηext (%) |
|---|---|---|---|
| Example 1 | Example Compound 20 | 448 | 21 |
| Example 2 | Example Compound 22 | 452 | 23 |
| Example 3 | Example Compound 33 | 450 | 22 |
| Example 4 | Example Compound 17 | 459 | 24 |
| Comparative Example 1 | Comparative Compound X-1 | 462 | 15 |
| Comparative Example 2 | Comparative Compound X-2 | 460 | 1 |
| Comparative Example 3 | Comparative Compound X-3 | 455 | 18 |
| Comparative Example 4 | Comparative Compound X-4 | 401 | 2 |
| Comparative Example 5 | Comparative Compound X-5 | 459 | 14 |

Referring to the results in Table 2, it may be found that the compound according to an embodiment of the present disclosure may attain high efficiency and emit deep blue light, when used as a material for thermally activated delayed fluorescence of organic electroluminescence devices.

For example, it may be found that the organic electroluminescence devices of Examples 1 to 4 achieve high efficiency compared with those of Comparative Examples 1 to 5. In Comparative Example 2, Comparative Compound X-2 has a relatively high $E_{ST}$ value of 0.3, and is not considered to function as a material for thermally activated delayed fluorescence. Furthermore, the organic electroluminescence device of Comparative Example 2 has low efficiency since Comparative Compound X-2 has a low aspect ratio of 1.1. In Comparative Example 4, Comparative Compound X-4 has a high $E_{ST}$ value of 0.28 despite a high aspect ratio of 1.9, and may not function as a material for thermally activated delayed fluorescence, thereby resulting in low efficiency of the organic electroluminescence devices of Comparative Example 4.

The organic electroluminescence devices of Comparative Examples 1, 3 and 5 achieve relatively high efficiency, and Comparative Compounds X-1, X-3 and X-5 have a low $E_{ST}$ value, which shows that they function as materials for thermally activated delayed fluorescence. Nonetheless, the organic electroluminescence devices of Comparative Examples 1, 3 and 5 have lower efficiency compared with those of Examples 1 to 4, which is considered resulting from the fact that the example compounds are likely to have a molecular orientation in the emission layer due to the higher aspect ratios thereof compared with those of Comparative Compounds X-1, X3 and X-5.

The compound for thermally activated delayed fluorescence according to an embodiment of the present disclosure attains high efficiency of an organic electroluminescence device including the compound due to the molecular structure and molecular aspect ratio thereof.

The terminology used herein is for the purpose of describing particular embodiments only and is not intended to be limiting of the present disclosure. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the exemplary embodiments of the present disclosure have been described, it is understood that the present disclosure should not be limited to these exemplary embodiments but various changes and modifications can be made by one ordinary skilled in the art within the spirit and scope of the present disclosure as hereinafter claimed.

What is claimed is:

1. A compound for thermally activated delayed fluorescence having a molecular aspect ratio of 1.5 or more, represented by the following Formula 1:

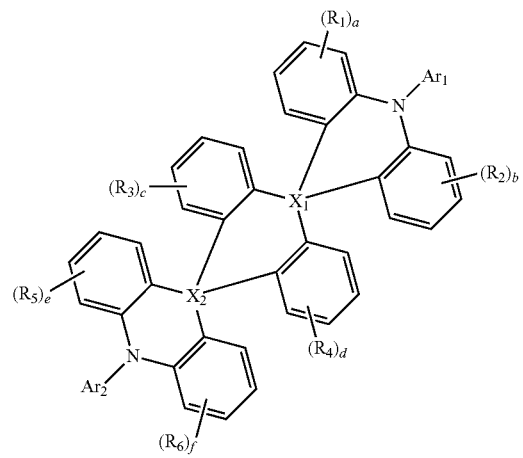

Formula 1 wherein in Formula 1, $X_1$ and $X_2$ are each independently C, Si or Ge, $R_1$ to $R_6$ are each independently a hydrogen atom, a deuterium atom, a halogen atom, or a substituted or unsubstituted alkyl group having 1 to 3 carbon atoms, a to f are each independently an integer of 0 to 4, $Ar_1$ and $Ar_2$ are each independently a substituted or unsubstituted aryl group having 6 to 60 carbon atoms for forming a ring, or a substituted or unsubstituted heteroaryl group having 2 to 60 carbon atoms for forming a ring, at least one of $Ar_1$ or $Ar_2$ is an electron accepting group, and $Ar_1$ and $Ar_2$ are different from each other; and wherein when $X_1$ and $X_2$ are C, Formula 1 is represented by any one of the following compounds 17, 20, 22, or 33:

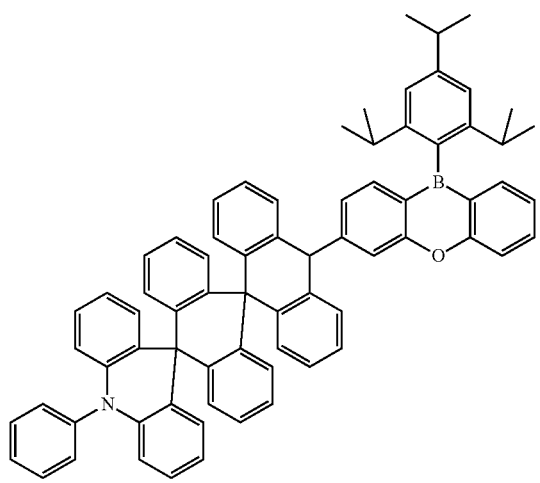

17

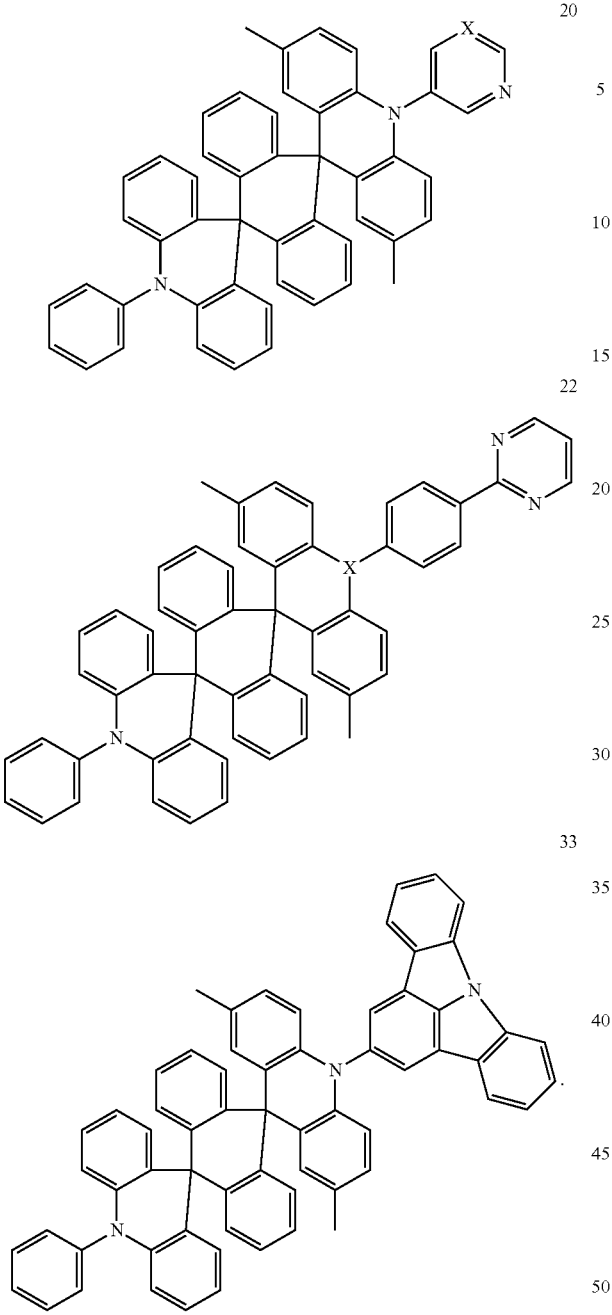

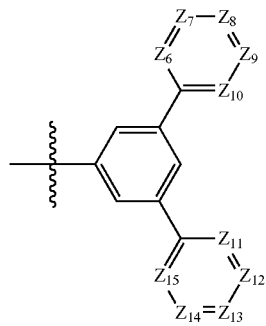

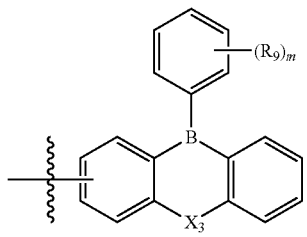

2. The compound of claim 1, wherein at least one of $Ar_1$ or $Ar_2$ is a substituted or unsubstituted heteroaryl group, or an aryl group substituted with a substituted or unsubstituted heteroaryl group.

3. The compound of claim 1, wherein at least one of $Ar_1$ or $Ar_2$ is represented by any one of the following Formula 2 or 3:

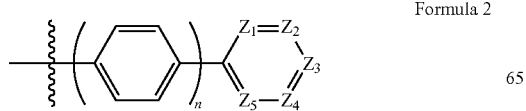

Formula 2

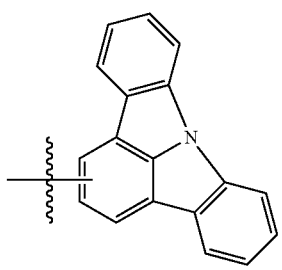

Formula 3 wherein in Formula 2, n is 0 or 1, $Z_1$ to $Z_5$ are each independently N or $CR_7$, when n is 0, $Z_1$ and $Z_5$ are each independently N or CH, one or two of $Z_1$ to $Z_5$ are N, $R_7$ is a hydrogen atom, a deuterium atom, a cyano group, a methyl group, a substituted or unsubstituted phenyl group, a substituted or unsubstituted pyridine group, or a substituted or unsubstituted pyrimidine group, wherein in Formula 3, $Z_6$ to $Z_{15}$ are each independently N or $CR_8$, at least one chosen from $Z_6$ to $Z_{15}$ is N, and $R_8$ is a hydrogen atom, a deuterium atom, a cyano group, or a methyl group.

4. The compound of claim 1, wherein at least one of $Ar_1$ or $Ar_2$ is represented by any one of the following Formulae 4 to 6:

Formula 4

Formula 5

-continued

Formula 6

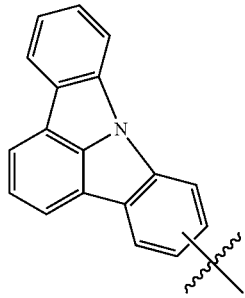

wherein in Formula 4,

X$_3$ is O or S,

R$_9$ is a hydrogen atom, a deuterium atom, or a substituted or unsubstituted alkyl group having 1 to 5 carbon atoms, and m is an integer of 0 to 5.

5. The compound of claim 1, wherein at least one of X$_1$ or X$_2$ is C.

6. The compound of claim 1, wherein Formula 1 is represented by the following Formula 1-1

Formula 1-1

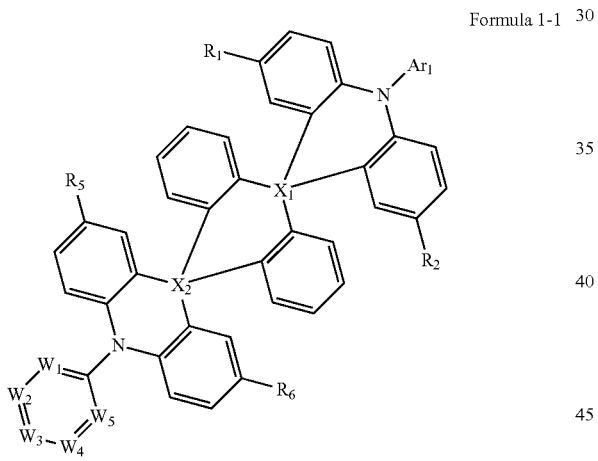

wherein in Formula 1-1,

Ar$_1$ is a substituted or unsubstituted heteroaryl group, or an aryl group substituted with a substituted or unsubstituted heteroaryl group, R$_1$, R$_2$, R$_5$ and R$_6$ are each independently a hydrogen atom, a deuterium atom, or a methyl group, W$_1$ to W$_5$ are each independently CH or N, the number of N in W$_1$ to W$_5$ is 0, 1, or 2, and X$_1$ and X$_2$ are the same as defined in claim 1.

7. The compound of claim 1, wherein the compound has an absolute value of the difference between a singlet energy level of the compound and a triplet energy level of the compound of about 0.2 eV or less.

8. The compound of claim 1, wherein the compound is any one selected from the group consisting of compounds represented in the following Compound Group 1:

Compound Group 1

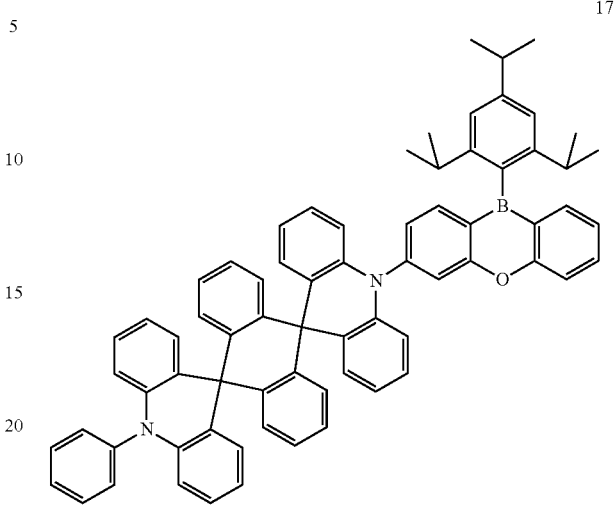

17

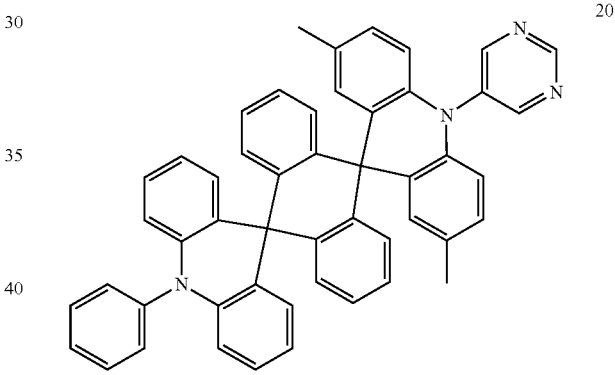

20

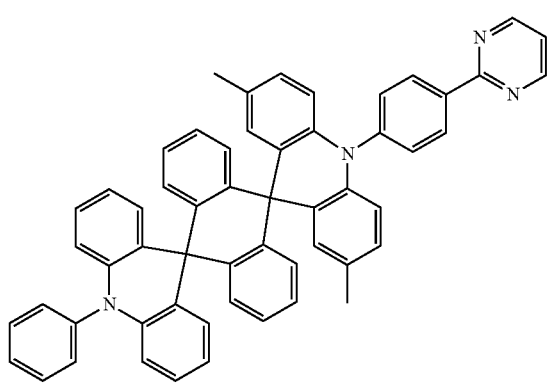

22

33
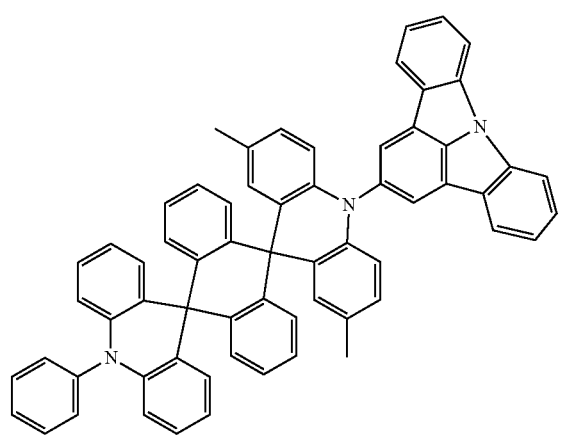
73
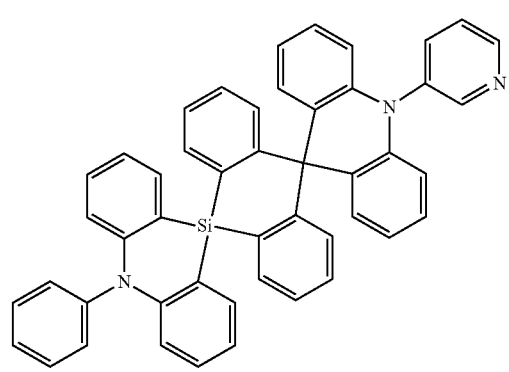
74
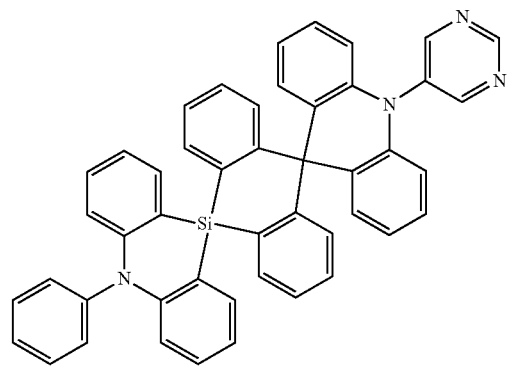
75
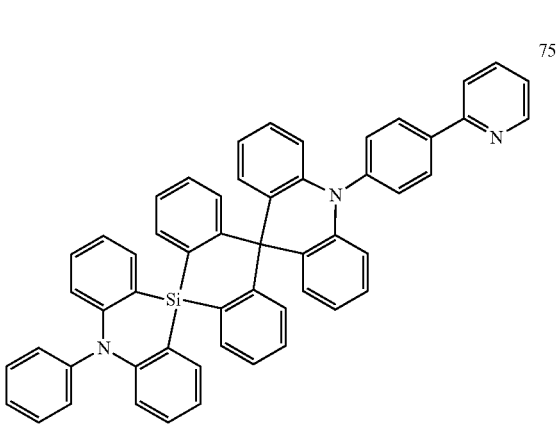
76
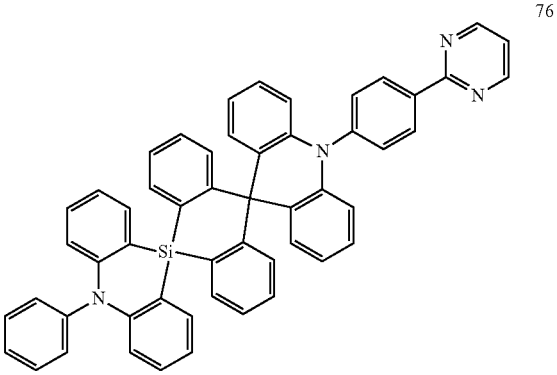
77
78
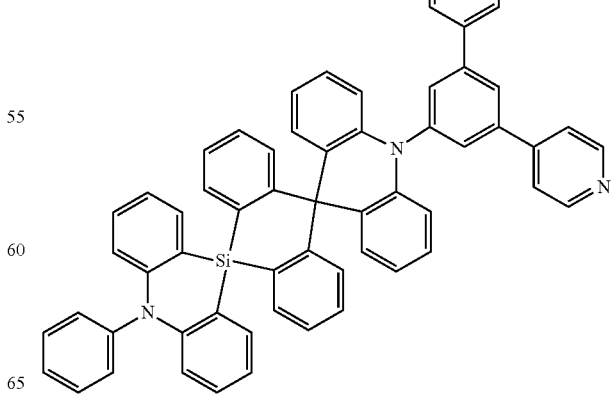

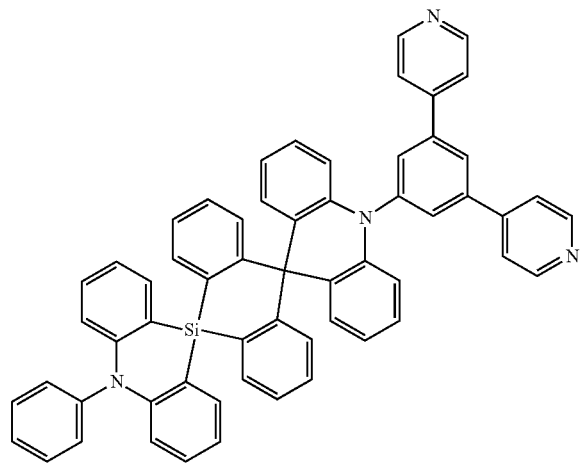
79
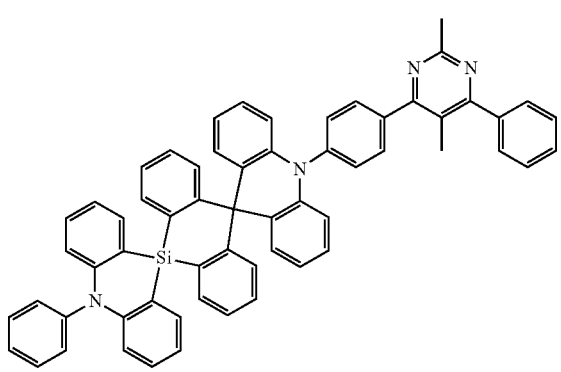
82
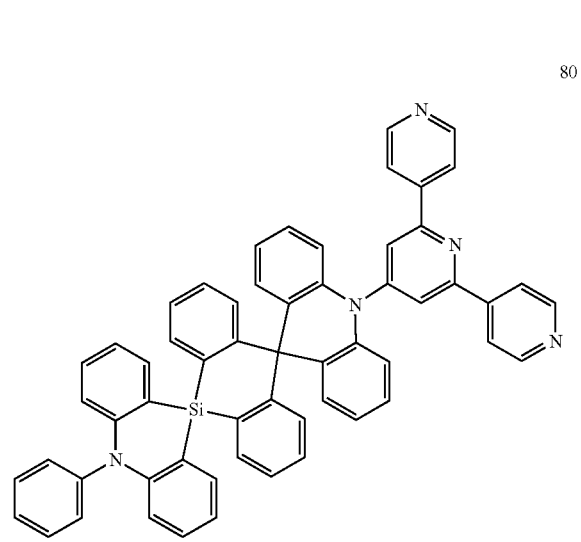
80
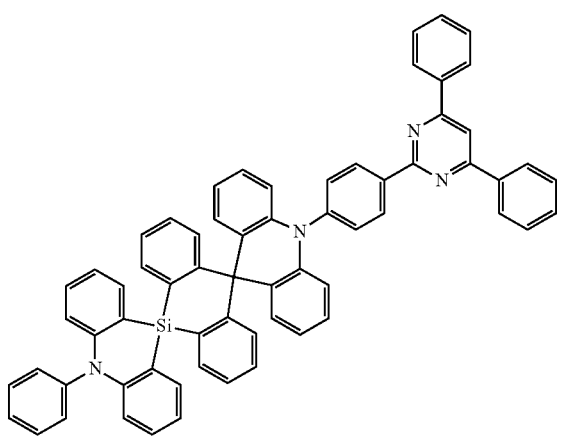
83
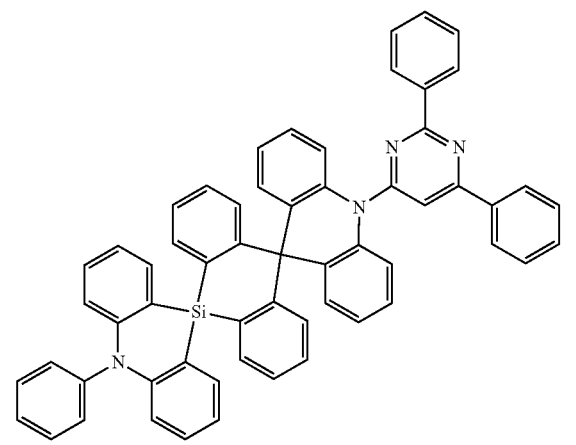
81
84

85
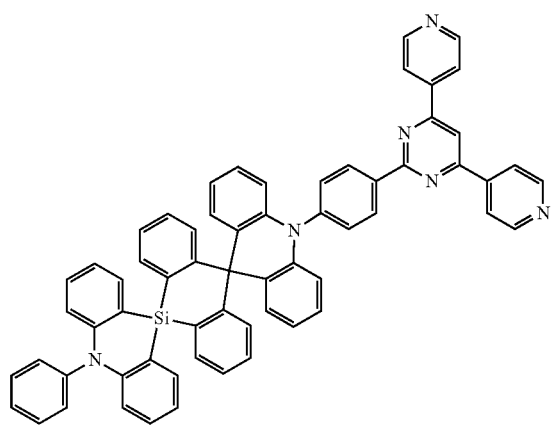
88
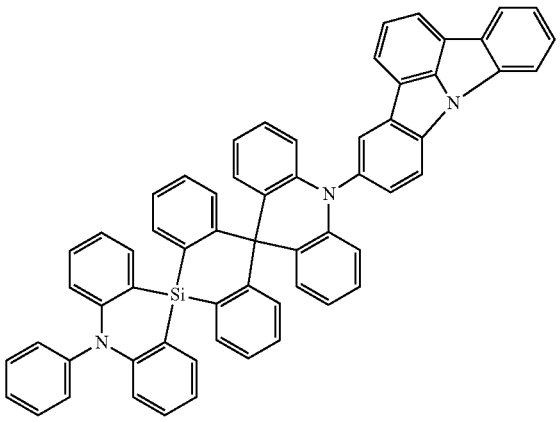
86
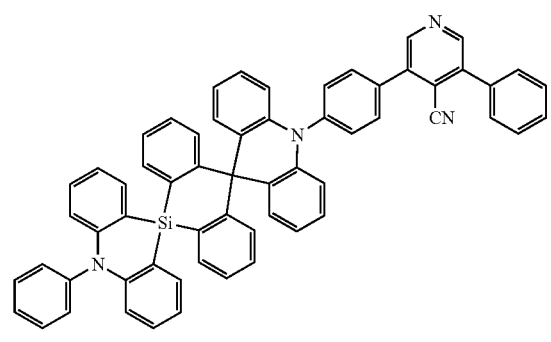
89
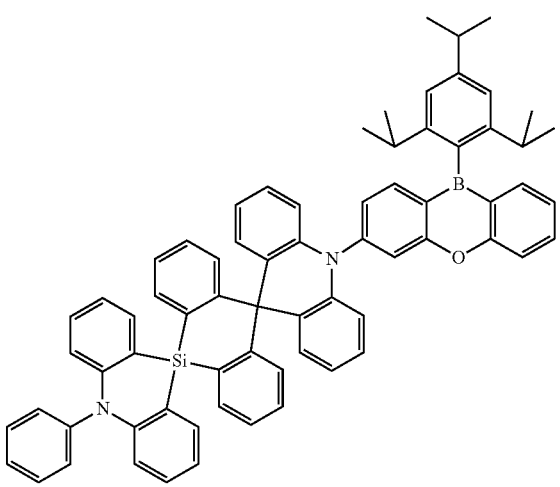
87
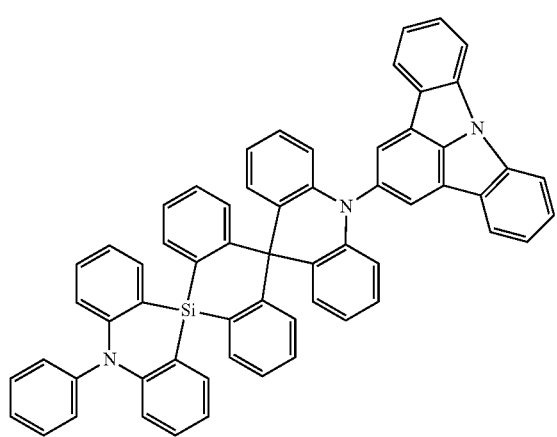
90
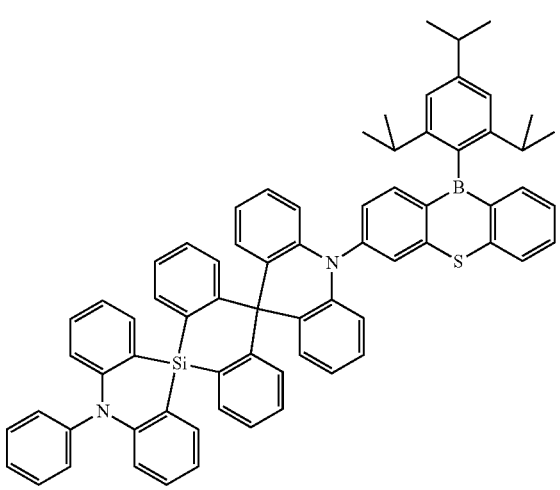

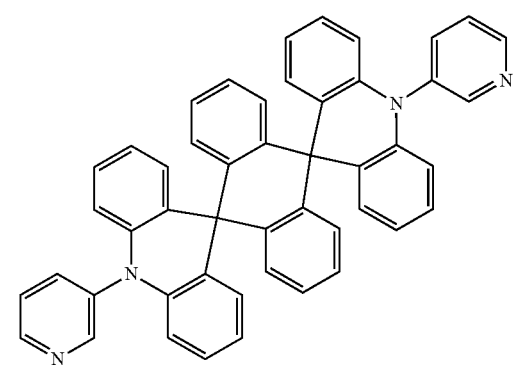
91
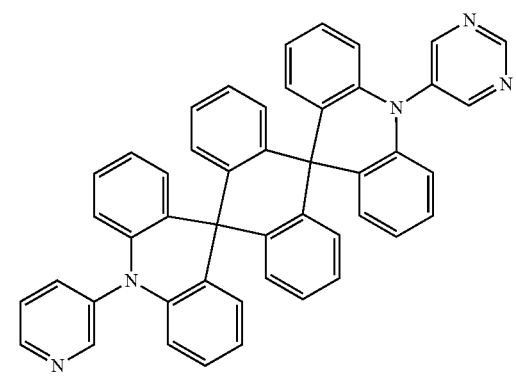
92
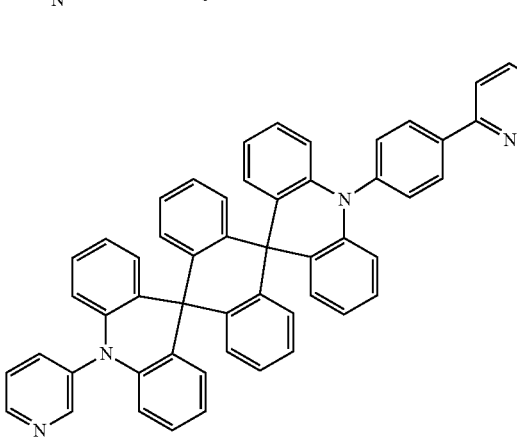
93
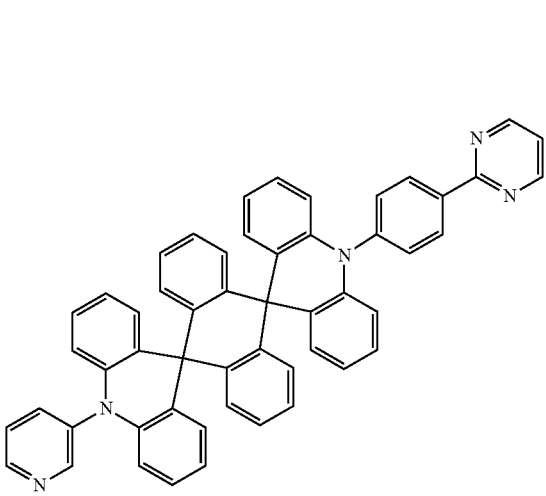
94
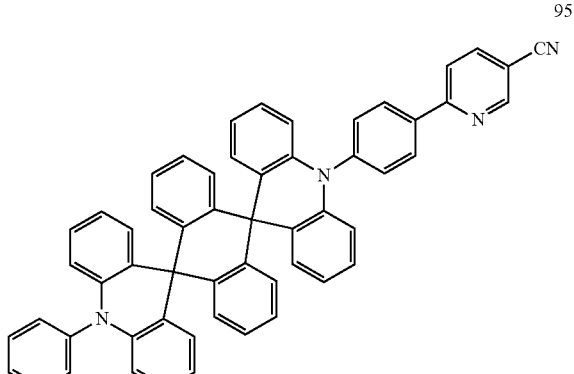
95
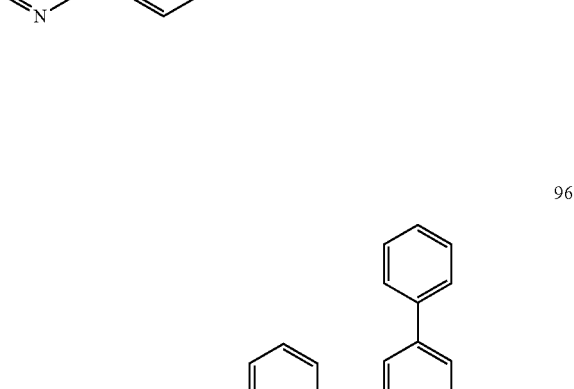
96
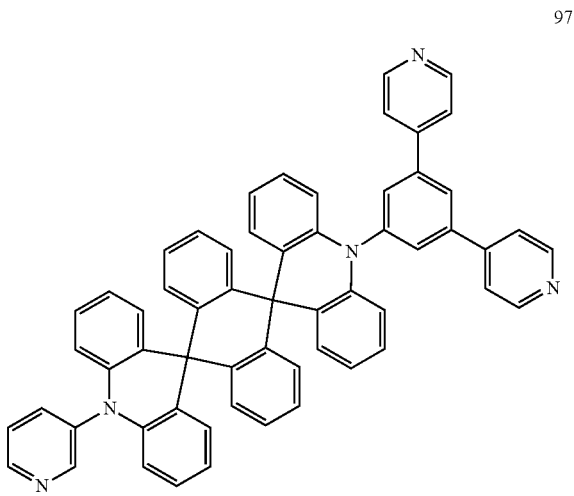
97

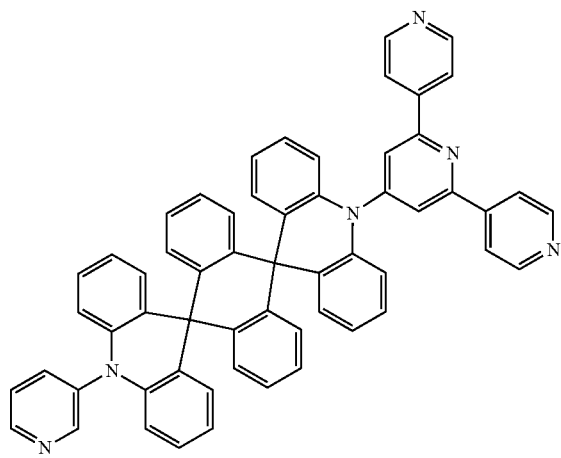
98
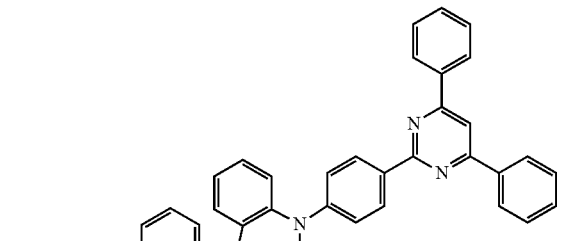
101
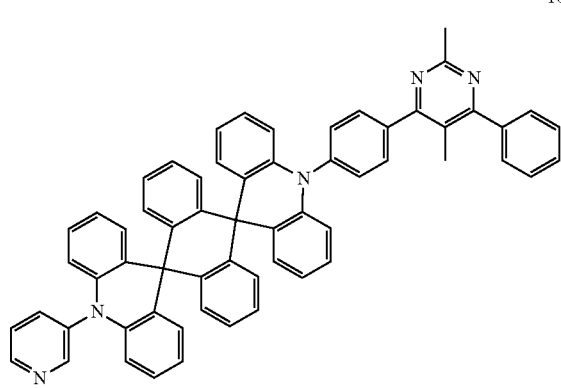
99
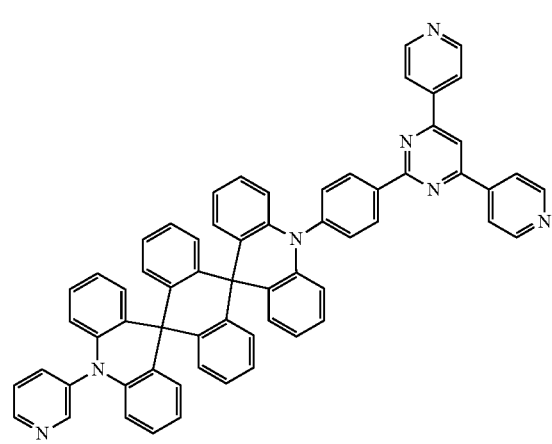
102
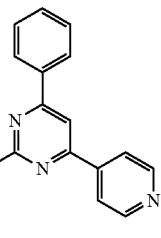
100
103

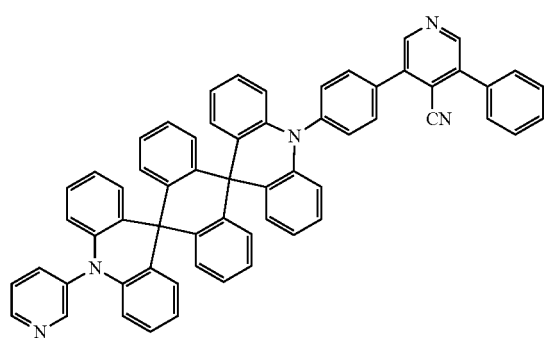
104
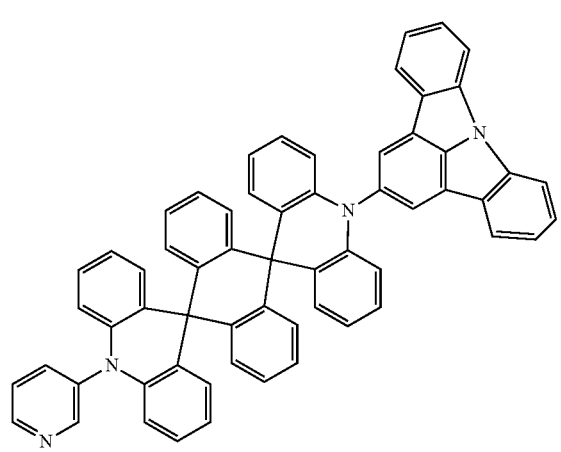
105
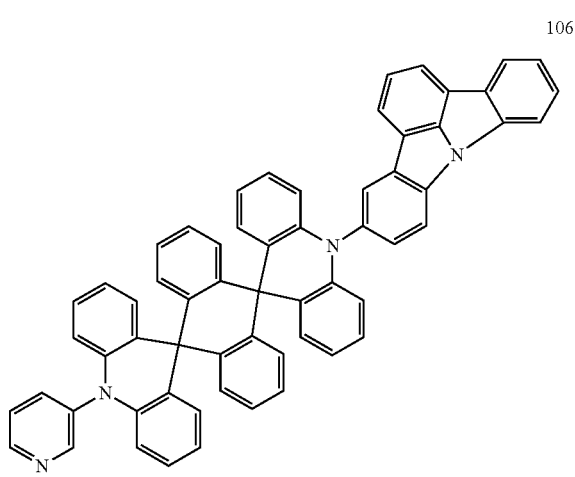
106
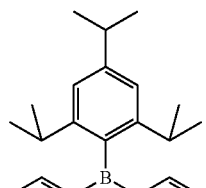
107
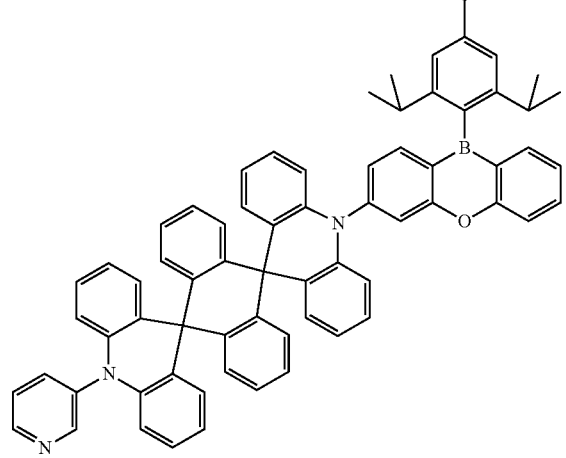
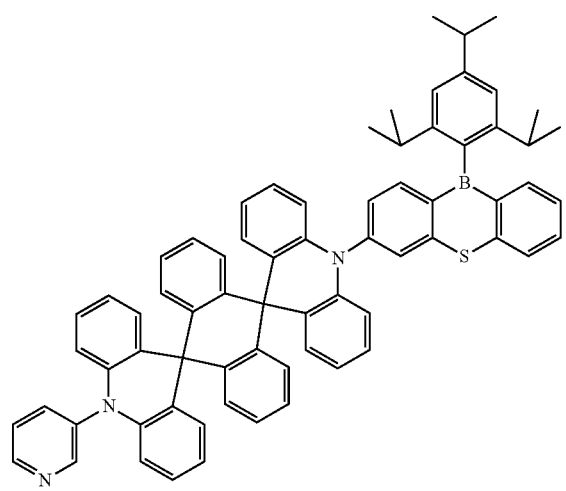
108
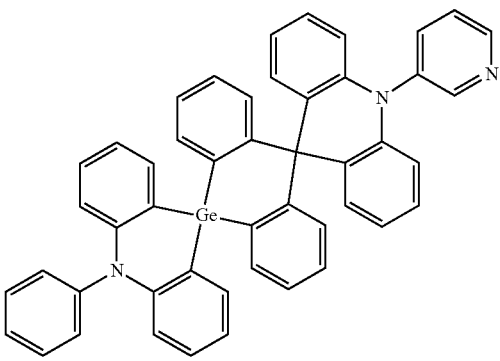
109

110
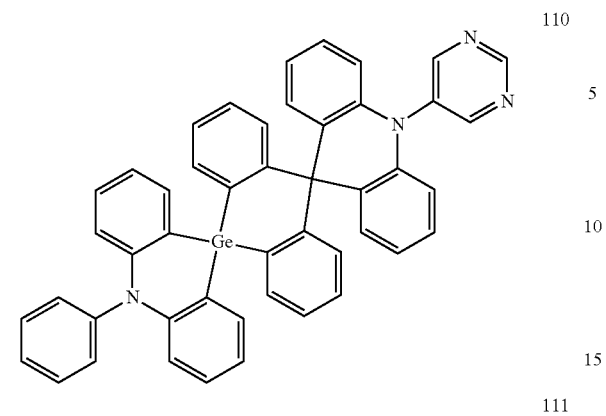
111
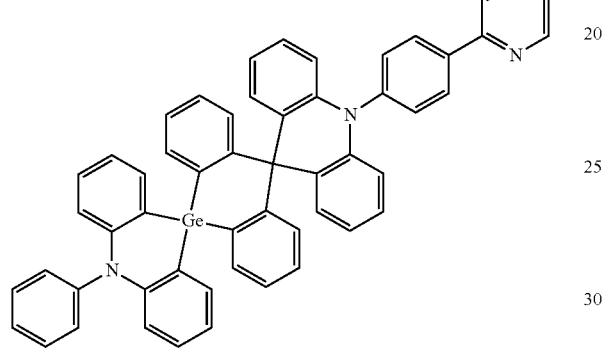
112
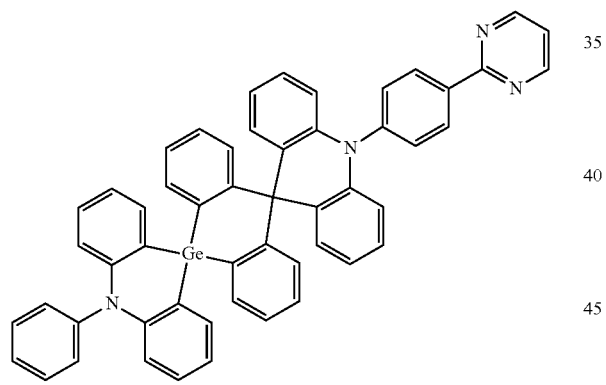
113
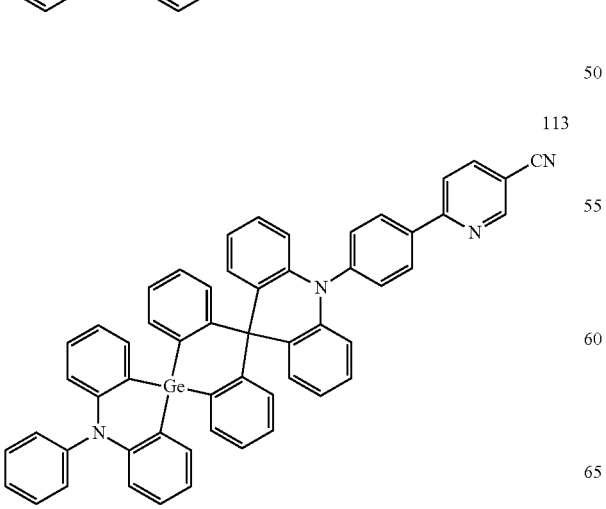
114
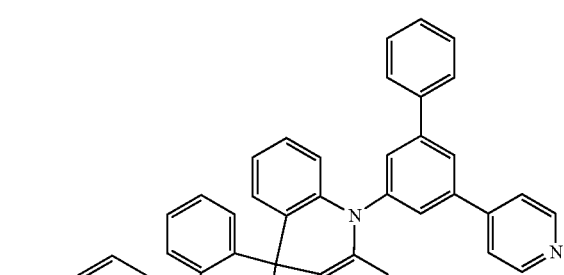
115
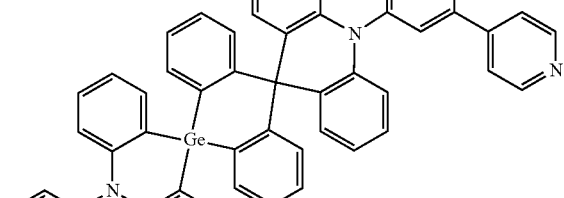
116
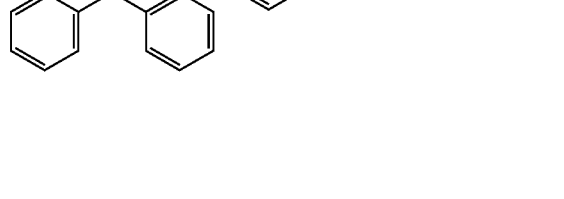

117
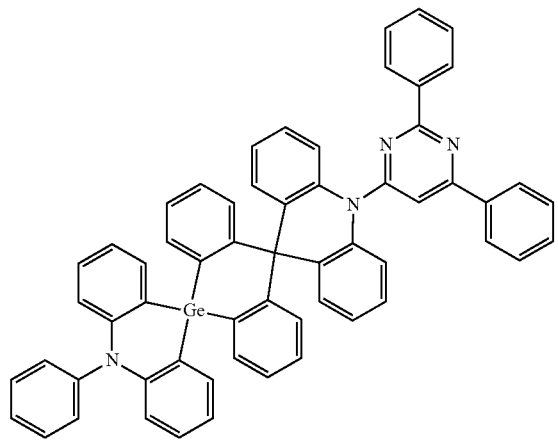
118
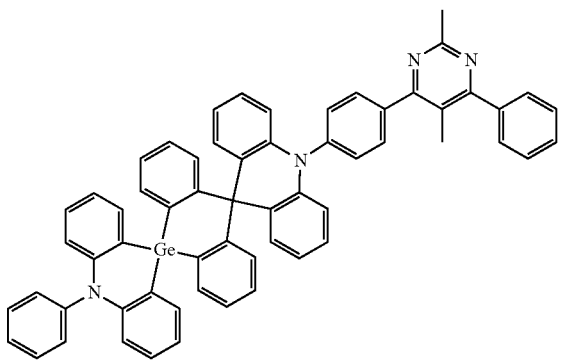
119
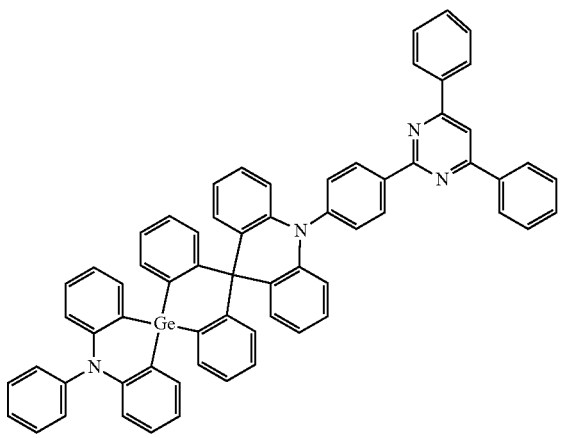
120
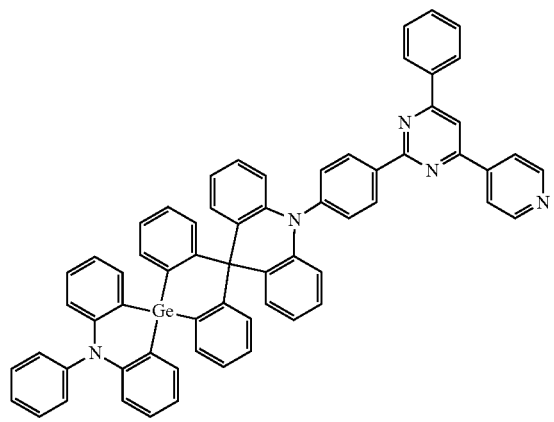
121
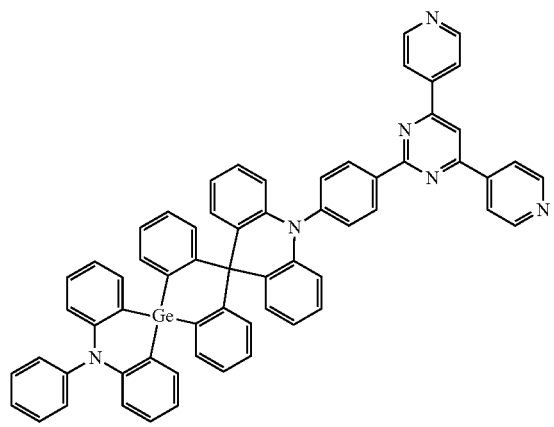
122
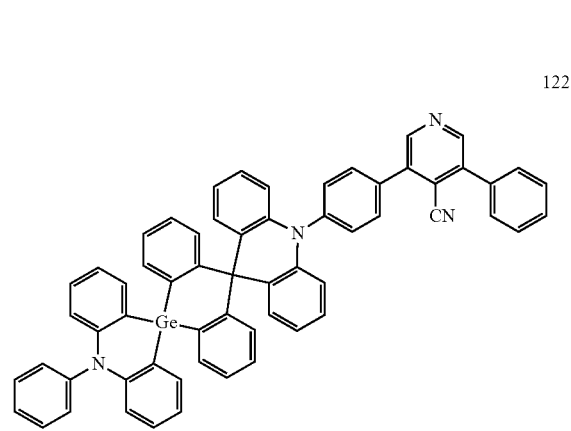

-continued

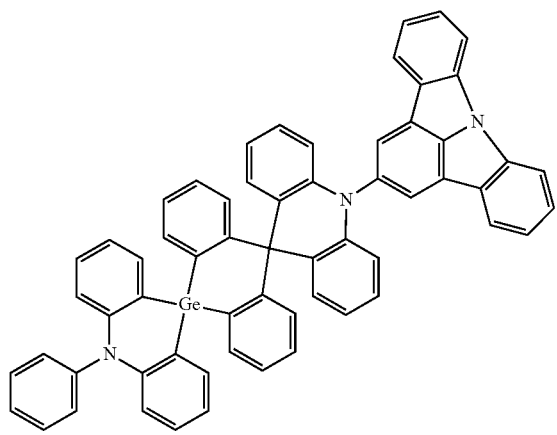

123

124

125

-continued

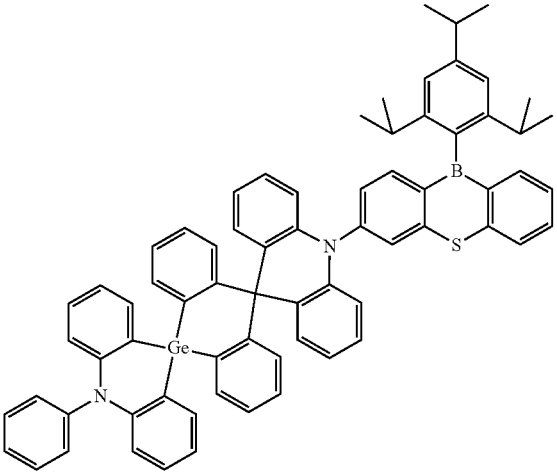

126

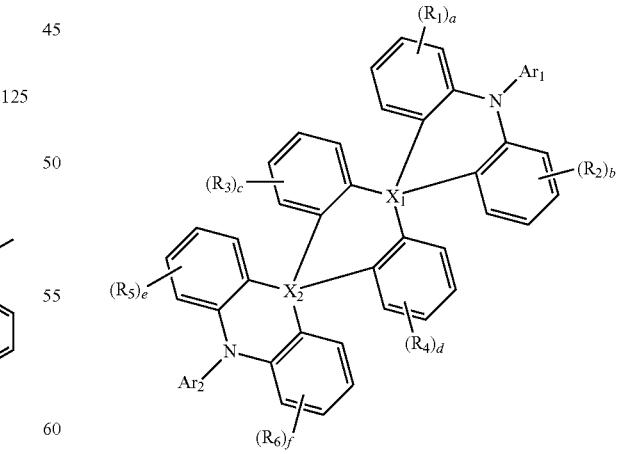

9. An organic electroluminescence device, comprising:
a first electrode;
a hole transport region disposed on the first electrode;
an emission layer disposed on the hole transport region;
an electron transport region disposed on the emission layer; and
a second electrode disposed on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof, and
wherein the emission layer comprises a compound for thermally activated delayed fluorescence having a molecular aspect ratio of 1.5 or more, represented by the following Formula 1:

Formula 1 wherein in Formula 1,
$X_1$ and $X_2$ are each independently C, Si or Ge,
$R_1$ to $R_6$ are each independently a hydrogen atom, a deuterium atom, a halogen atom, or a substituted or unsubstituted alkyl group having 1 to 3 carbon atoms, a to f are each independently an integer of 0 to 4, Ar$_1$ and Ar$_2$ are each independently a substituted or unsubstituted aryl group having 6 to 60 carbon atoms for forming a ring, or a substituted or unsubstituted heteroaryl group having 2 to 60 carbon atoms for forming a ring, at least one of Ar$_1$ or Ar$_2$ is an electron accepting group, Ar$_1$ and Ar$_2$ are different from each other; and wherein when X$_1$ and X$_2$ are C, Formula 1 is represented by any one of the following compounds 17, 20, 22, or 33:

17

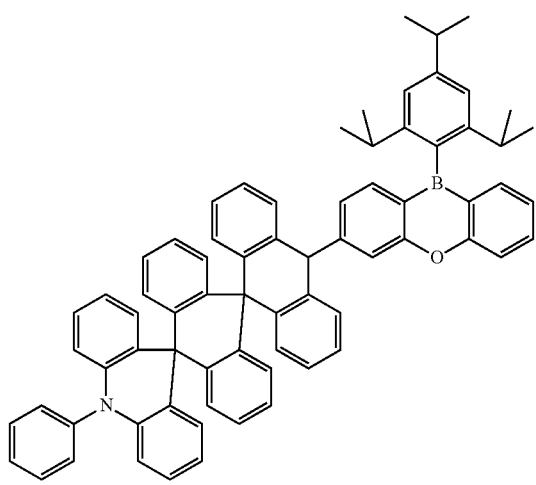

20

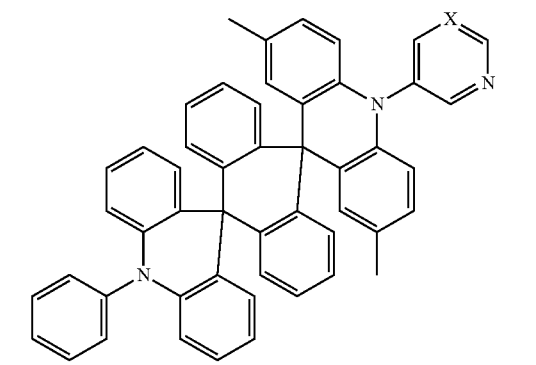

22

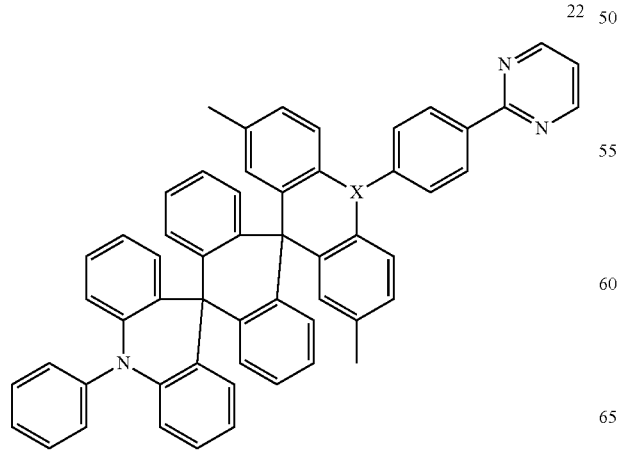

33

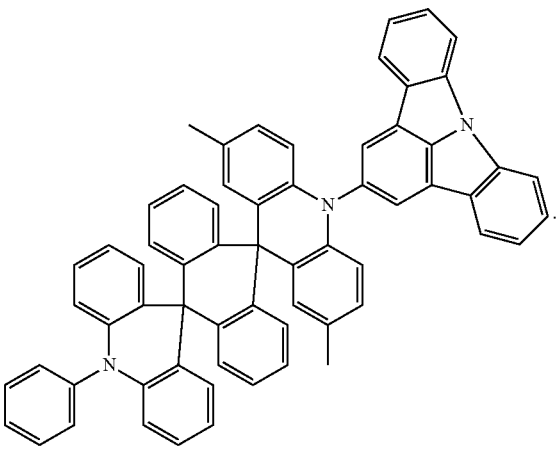

10. The organic electroluminescence device of claim 9, wherein:
the emission layer comprises a host and a dopant, and
the dopant comprises the compound for thermally activated delayed fluorescence.

11. The organic electroluminescence device of claim 9, wherein at least one of Ar$_1$ or Ar$_2$ is a substituted or unsubstituted heteroaryl group, or an aryl group substituted with a substituted or unsubstituted heteroaryl group.

12. The organic electroluminescence device of claim 9, wherein at least one of Ar$_1$ or Ar$_2$ is represented by any one of the following Formula 2 or 3:

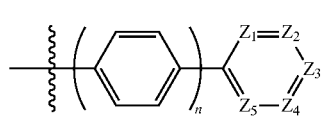

Formula 2

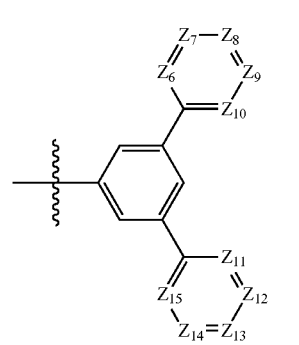

Formula 3 wherein in Formula 2,
n is 0 or 1,
Z$_1$ to Z$_5$ are each independently N or CR$_7$,
when n is 0, Z$_1$ and Z$_5$ are each independently N or CH,
one or two of Z$_1$ to Z$_5$ are N,
R$_7$ is a hydrogen atom, a deuterium atom, a cyano group, a methyl group, a substituted or unsubstituted phenyl group, a substituted or unsubstituted pyridine group, or a substituted or unsubstituted pyrimidine group,
wherein in Formula 3,
Z$_6$ to Z$_{15}$ are each independently N or CR$_8$,
at least one chosen from Z$_6$ to Z$_{15}$ is N, and
R$_8$ is a hydrogen atom, a deuterium atom, a cyano group, or a methyl group.

13. The organic electroluminescence device of claim 9, wherein at least one of $Ar_1$ or $Ar_2$ is represented by any one of the following Formulae 4 to 6:

Formula 4

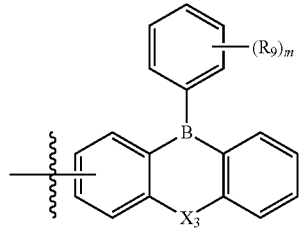

Formula 5

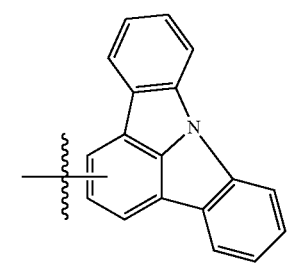

Formula 6

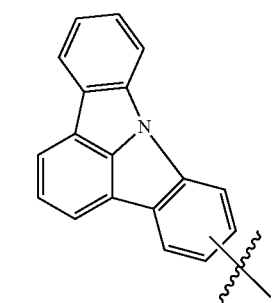

wherein in Formula 4, $X_3$ is O or S, $R_9$ is a hydrogen atom, a deuterium atom, or a substituted or unsubstituted alkyl group having 1 to 5 carbon atoms, and m is an integer of 0 to 5.

14. The organic electroluminescence device of claim 9, wherein at least one of $X_1$ or $X_2$ is C.

15. The organic electroluminescence device of claim 9, wherein Formula 1 is represented by the following Formula 1-1:

Formula 1-1

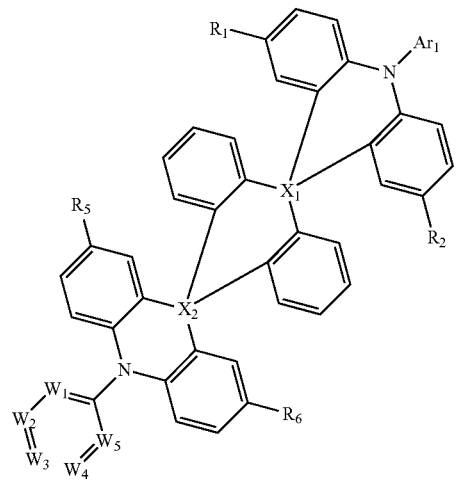

wherein in Formula 1-1, $Ar_1$ is a substituted or unsubstituted heteroaryl group, or an aryl group substituted with a substituted or unsubstituted heteroaryl group, $R_1$, $R_2$, $R_5$ and $R_6$ are each independently a hydrogen atom, a deuterium atom, or a methyl group, $W_1$ to $W_5$ are each independently CH or N, the number of N in $W_1$ to $W_5$ is 0, 1, or 2, and $X_1$ and $X_2$ are the same as defined in claim 9.

16. The organic electroluminescence device of claim 9, wherein the compound has an absolute value of the difference between a singlet energy level of the compound and a triplet energy level of the compound of about 0.2 eV or less.

17. The organic electroluminescence device of claim 9, wherein the compound emits blue light with a wavelength range of about 470 nm or shorter.

18. The organic electroluminescence device of claim 9, wherein the compound is at least one selected from the group consisting of compounds represented in the following Compound Group 1:

Compound Group 1

17

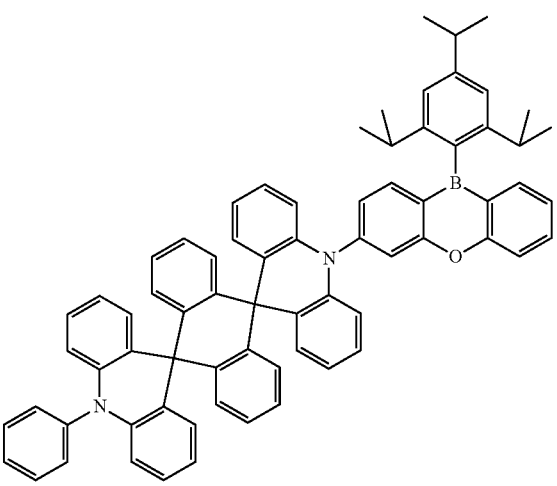

101
-continued
20
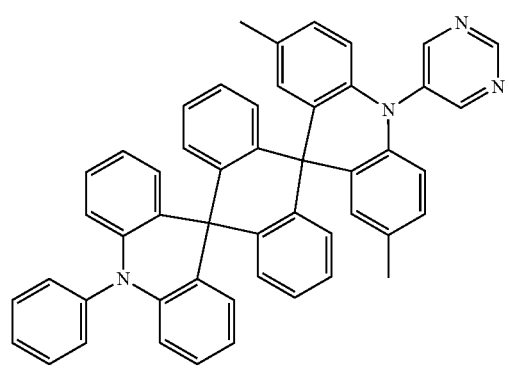
22
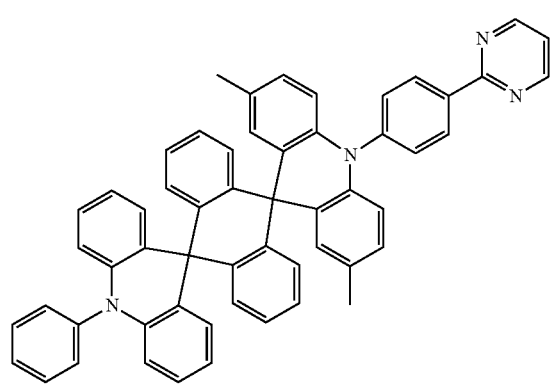
33
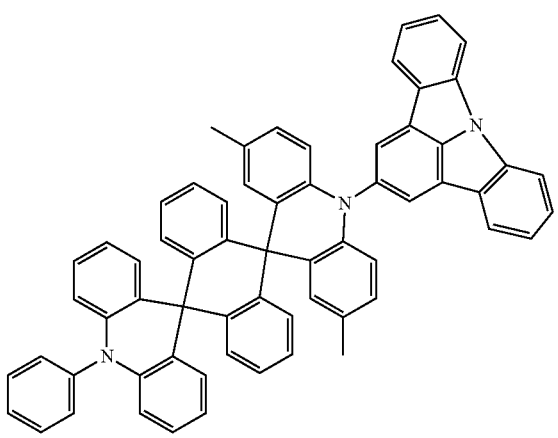
73
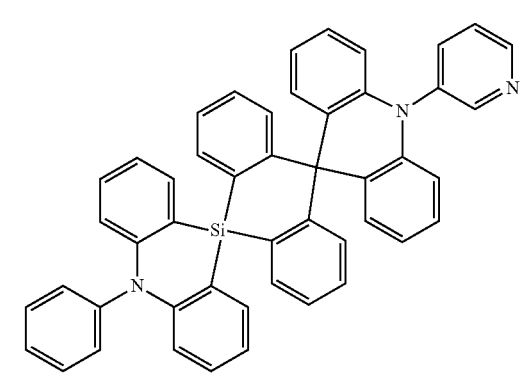
102
-continued
74
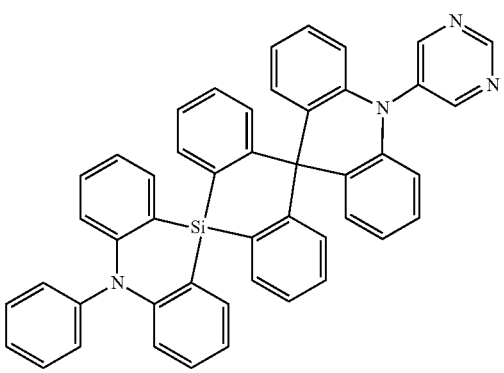
75
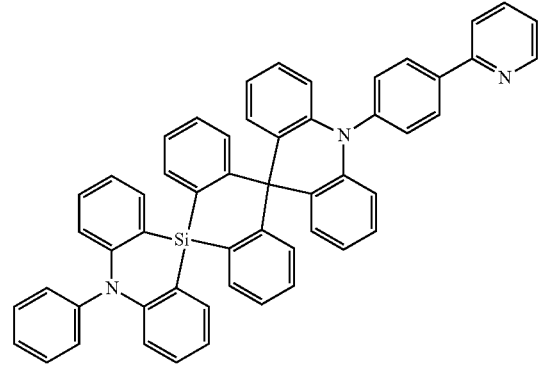
76
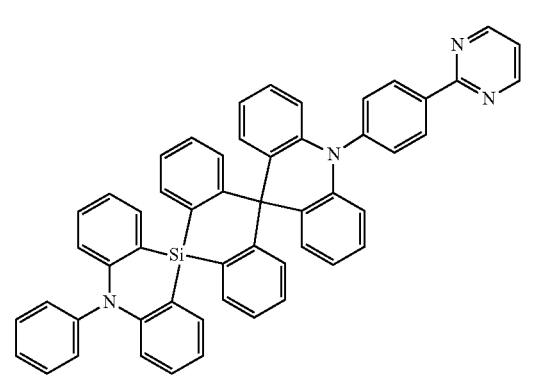
77
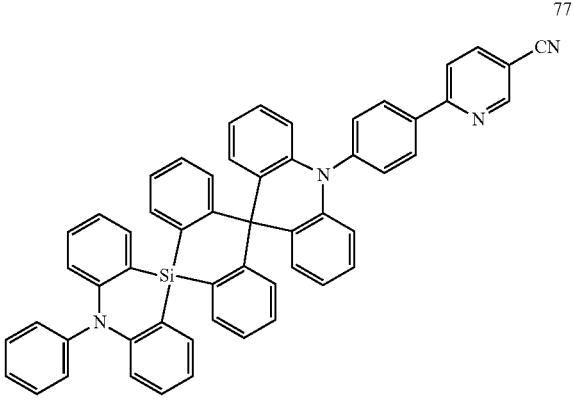

103
-continued
78
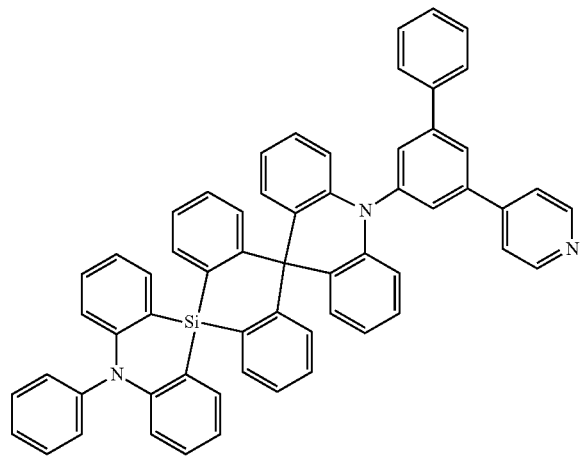
79
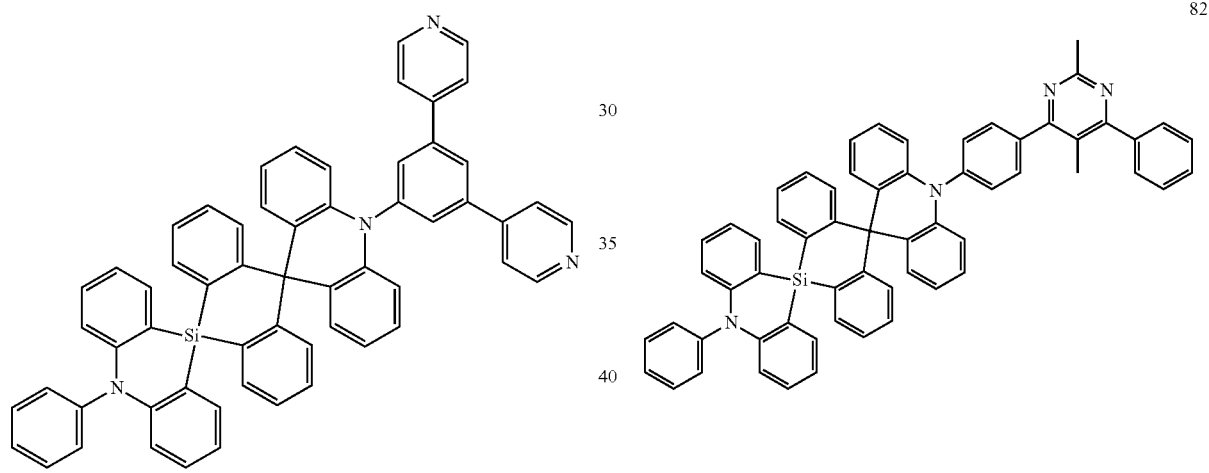
80
104
-continued
81
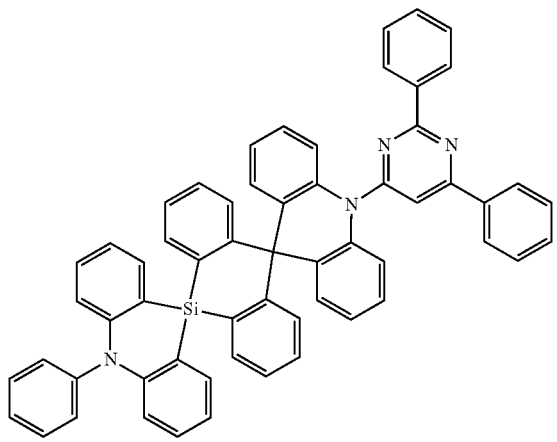
82
83
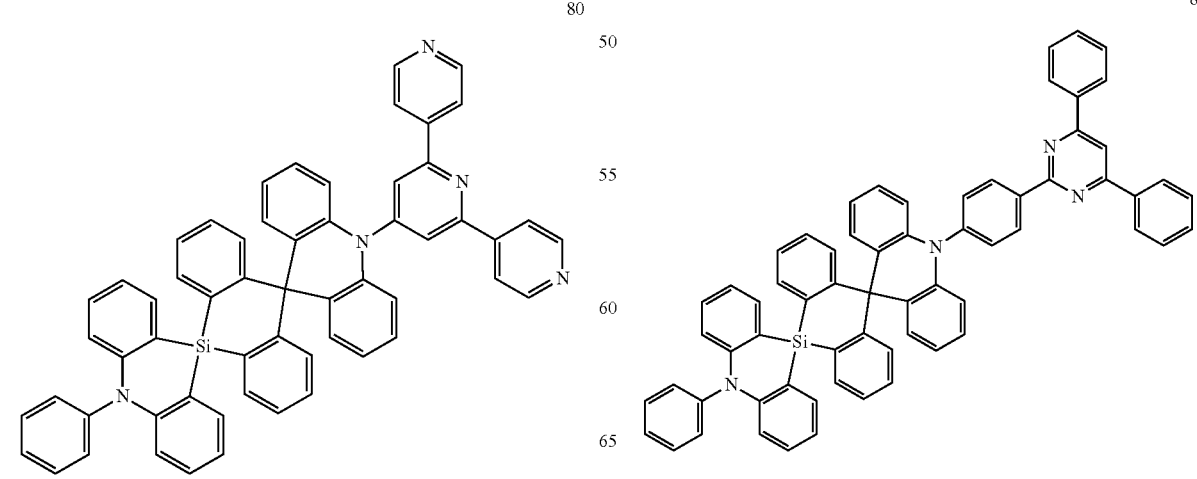

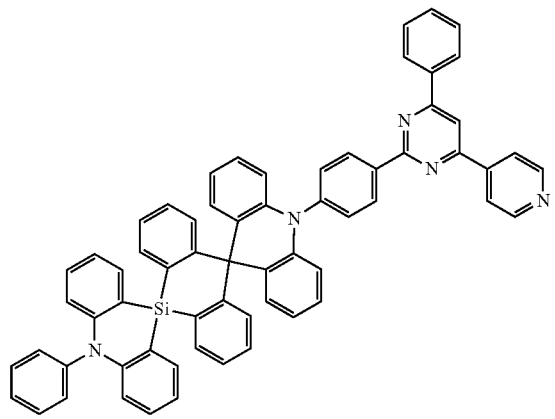
84
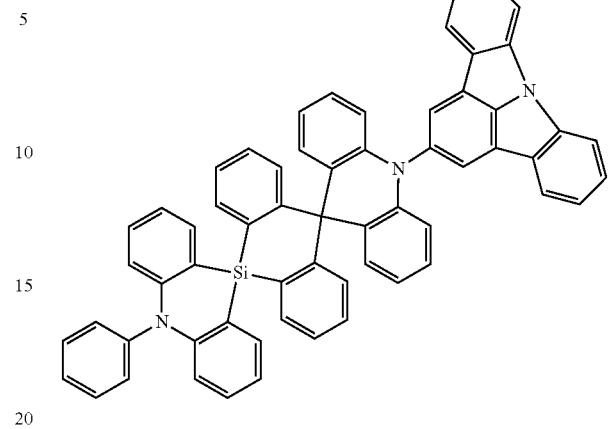
87
85
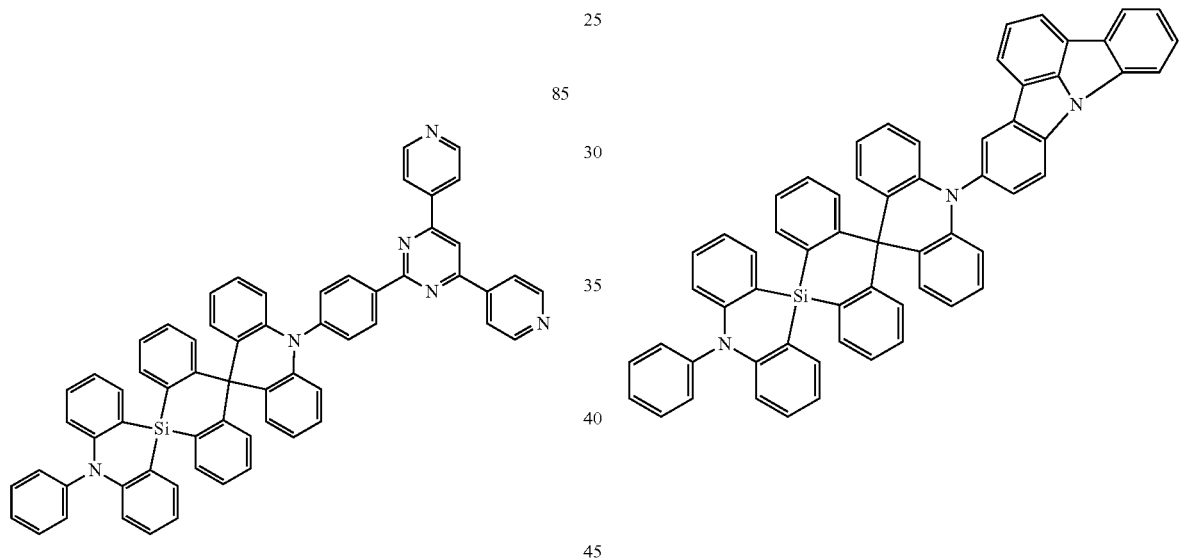
88
86
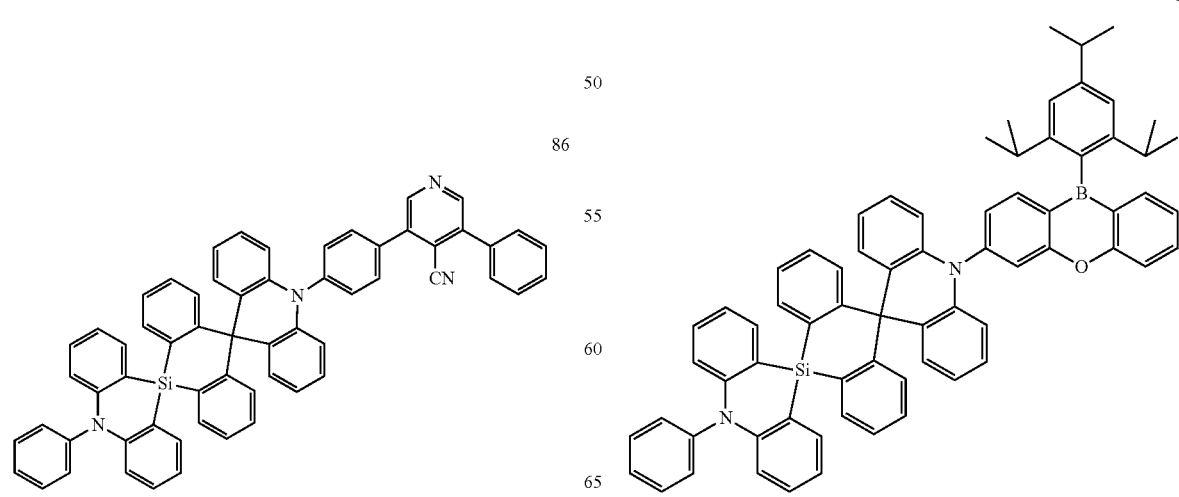
89

90
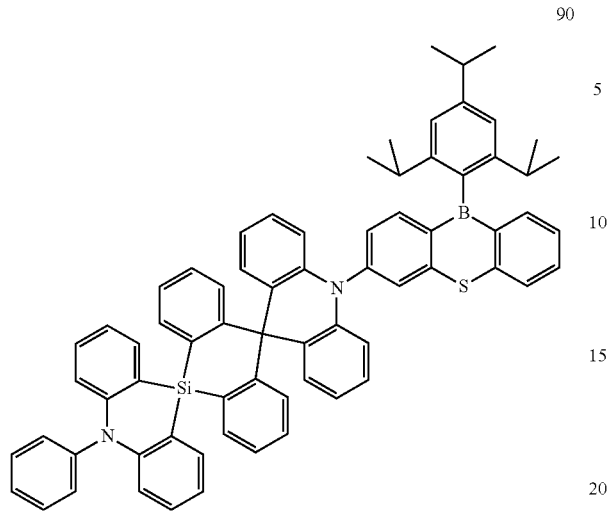
91
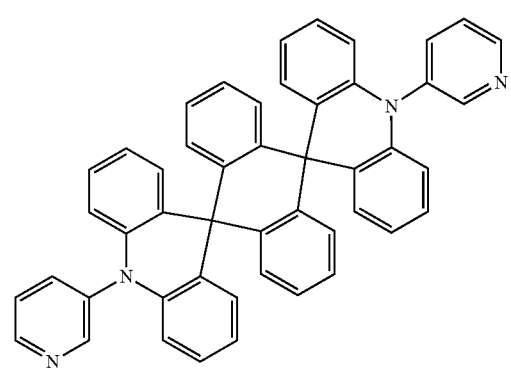
92
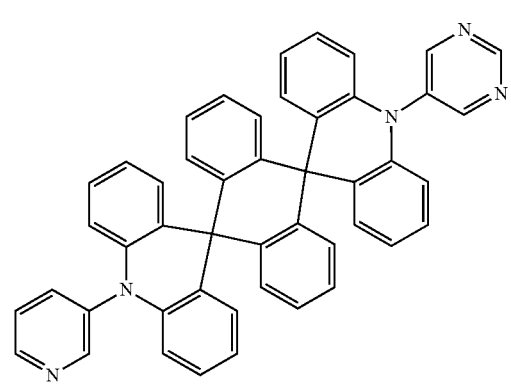
93
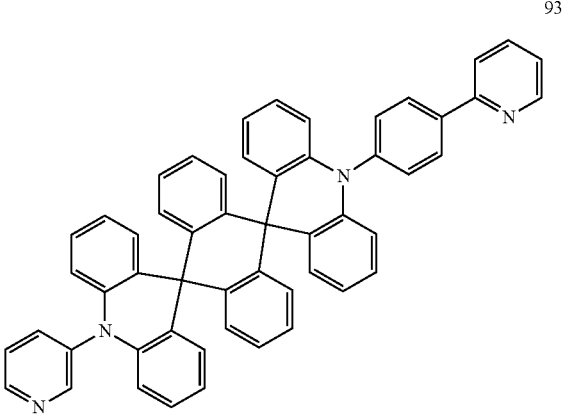
94
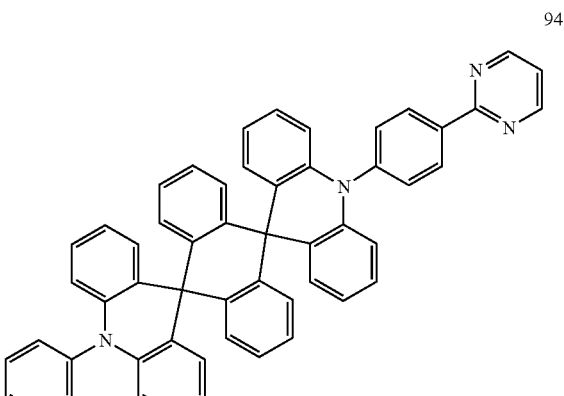
95
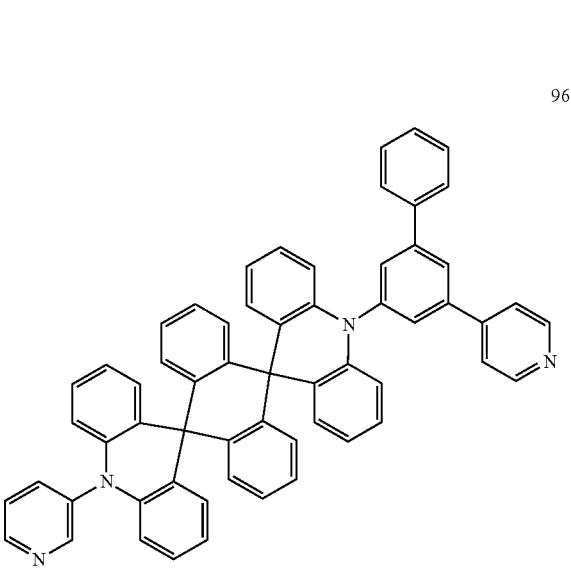
96

97
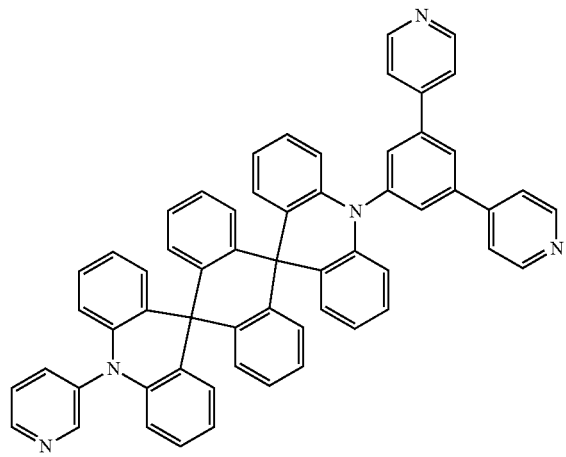
98
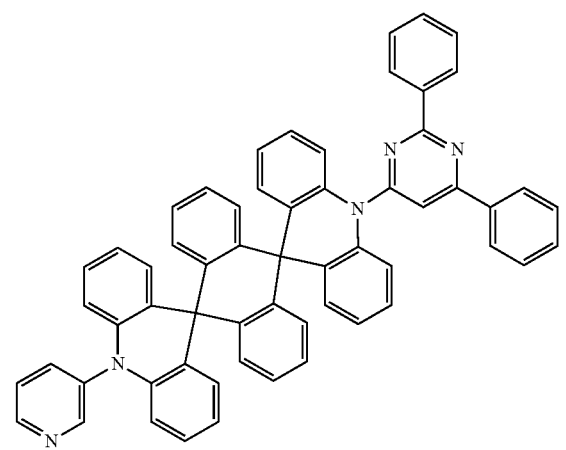
99
100
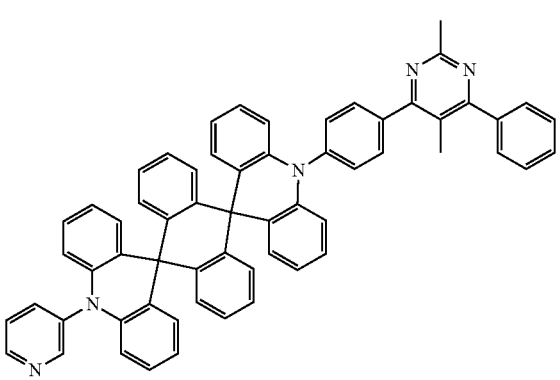
101
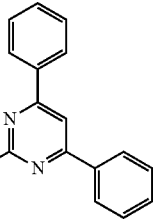
102
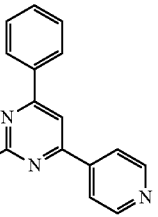

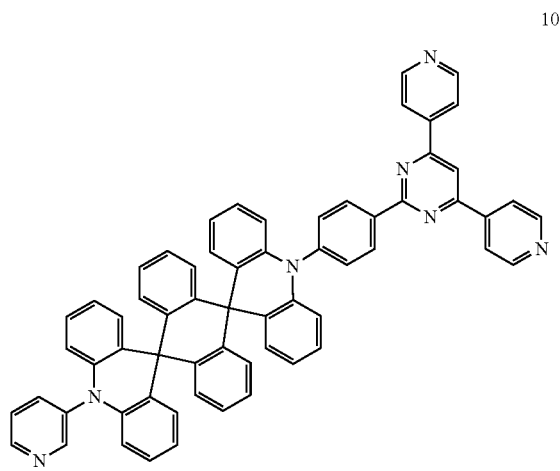
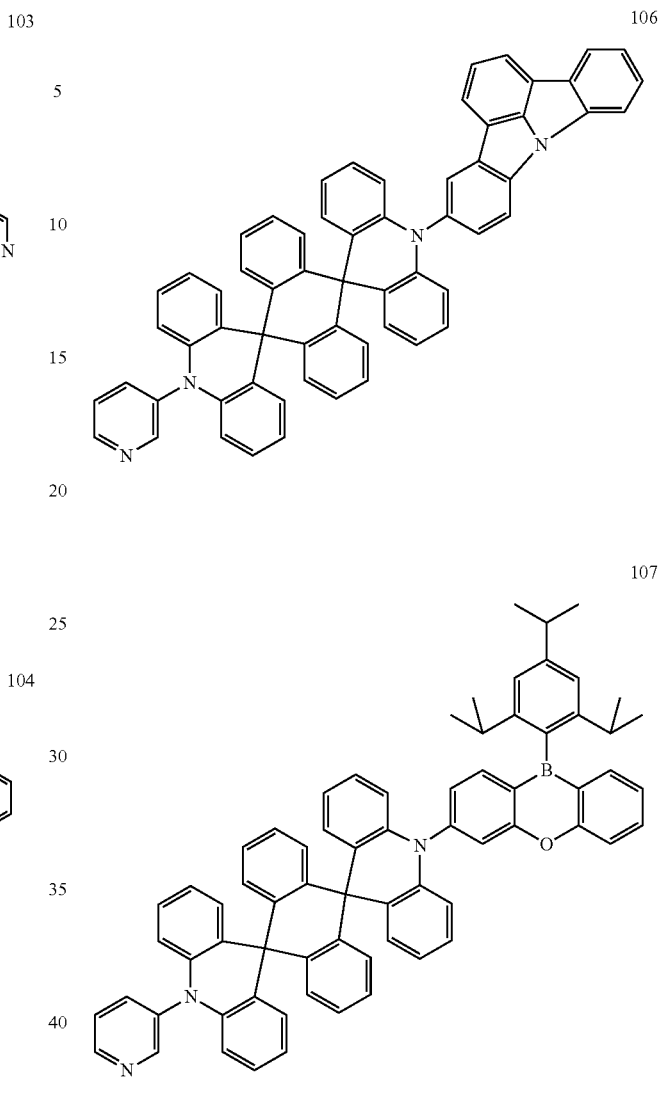
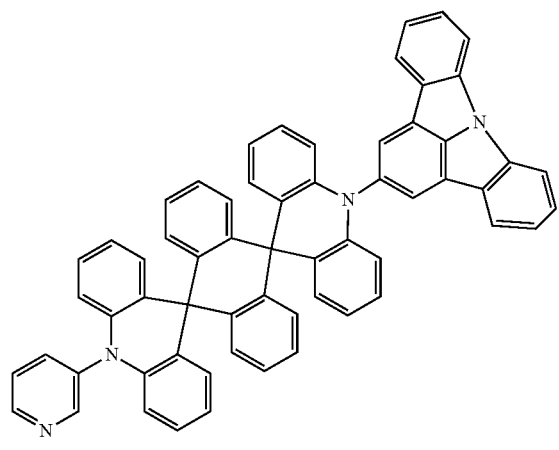

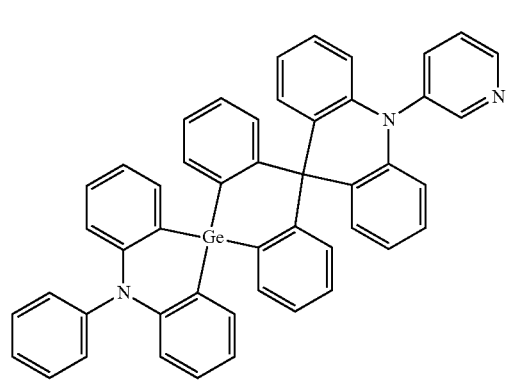
109
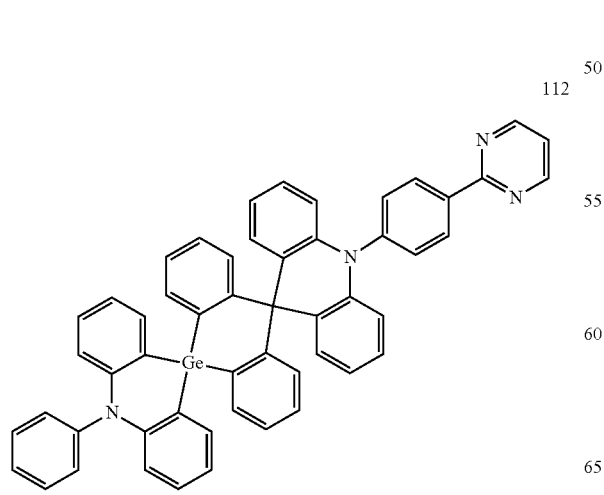
110
111
112
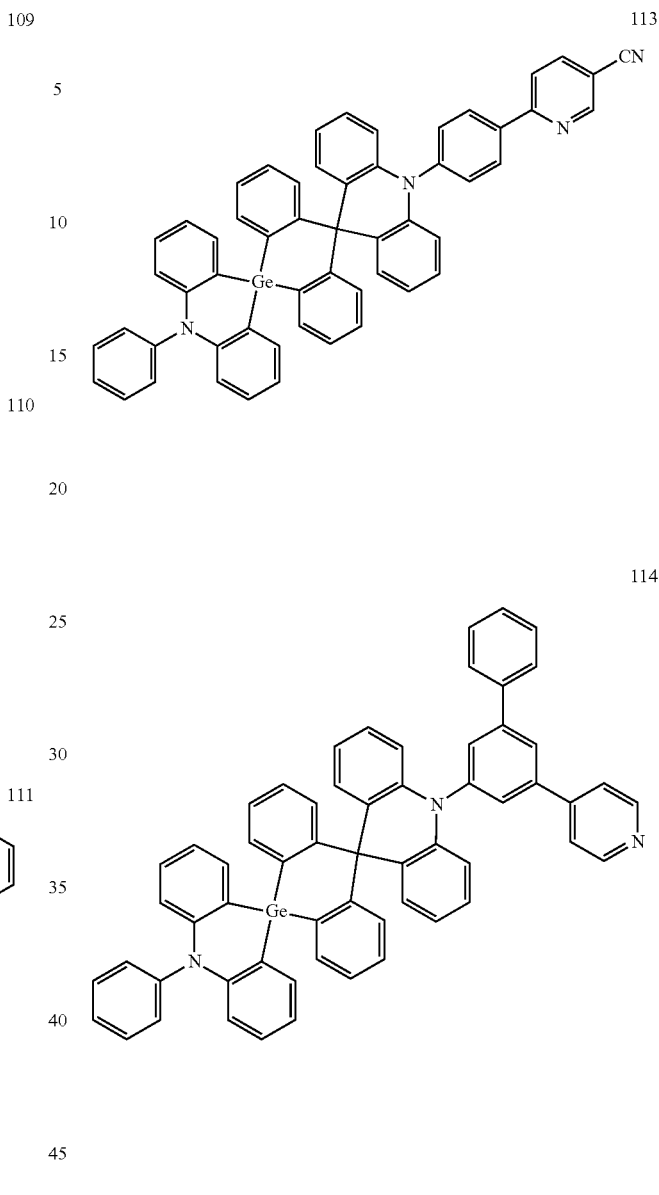
113
114
115

115
-continued
116
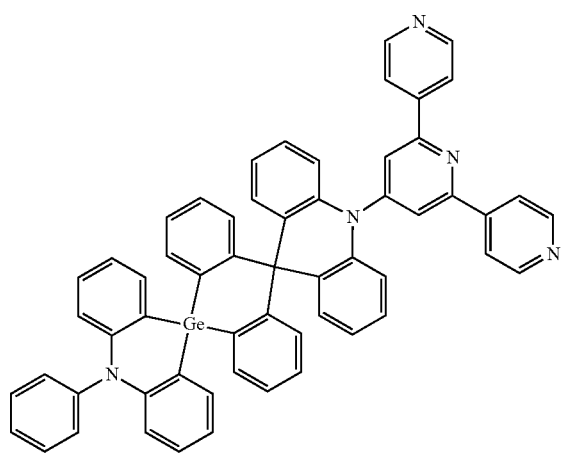
117
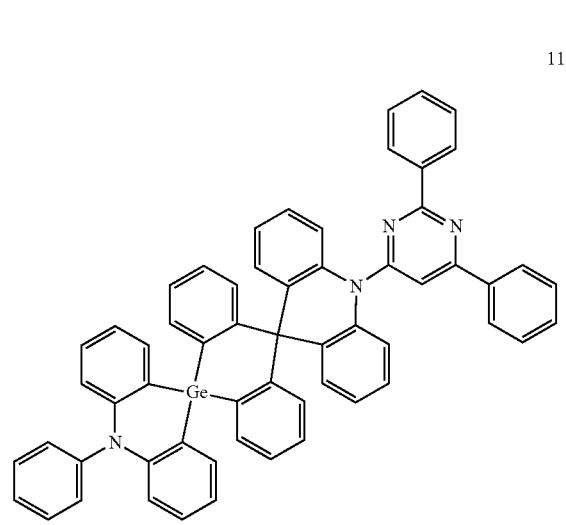
118
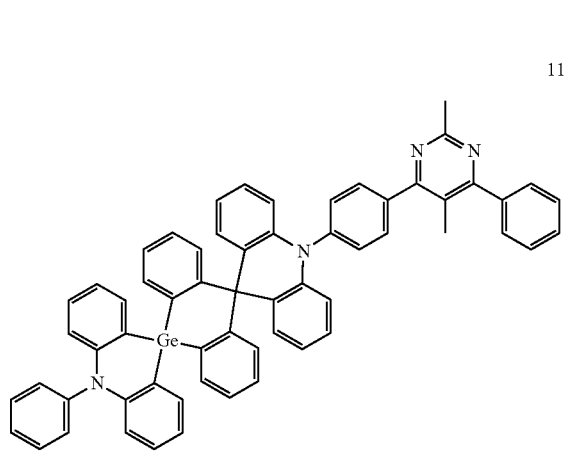
116
-continued
119
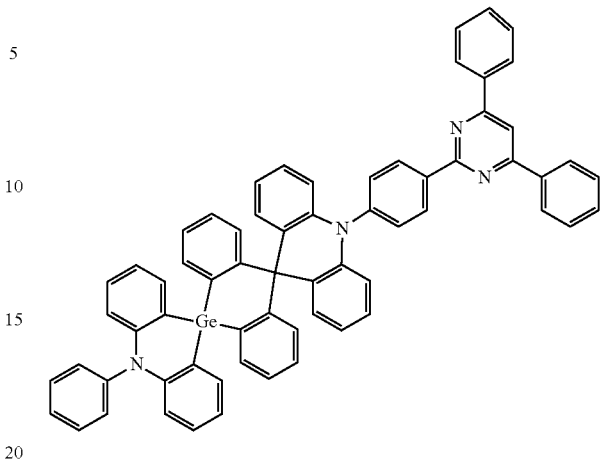
120
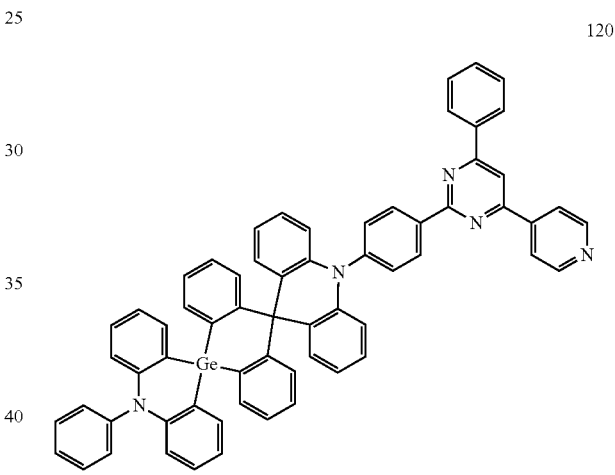
121
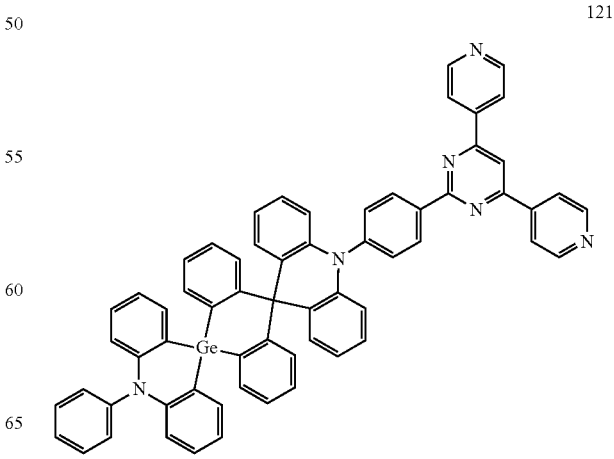

117
-continued
122
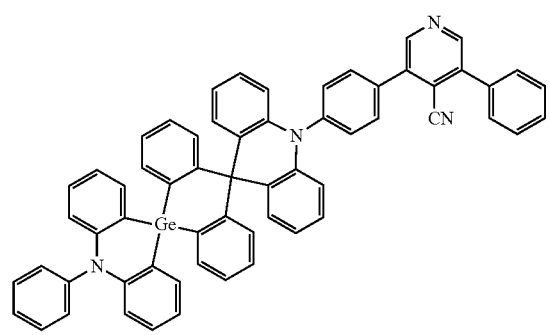
123
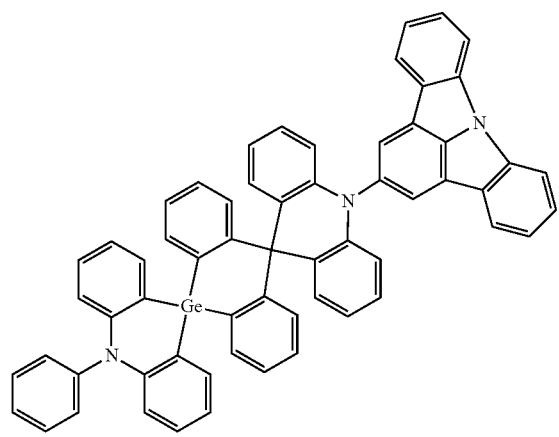
124
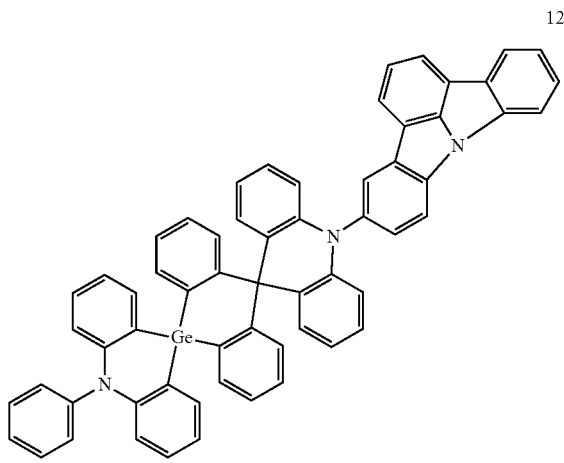
118
-continued
125
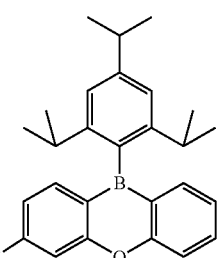
126
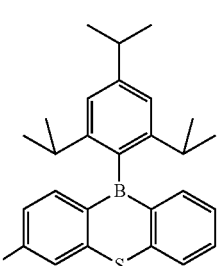
* * * * *

UNITED STATES PATENT AND TRADEMARK OFFICE
CERTIFICATE OF CORRECTION

PATENT NO. : 11,018,306 B2
APPLICATION NO. : 15/952630
DATED : May 25, 2021
INVENTOR(S) : Nobutaka Akashi Page 1 of 4

It is certified that error appears in the above-identified patent and that said Letters Patent is hereby corrected as shown below:

In the Claims

In Column 74, Lines 48-66, in Claim 1, delete

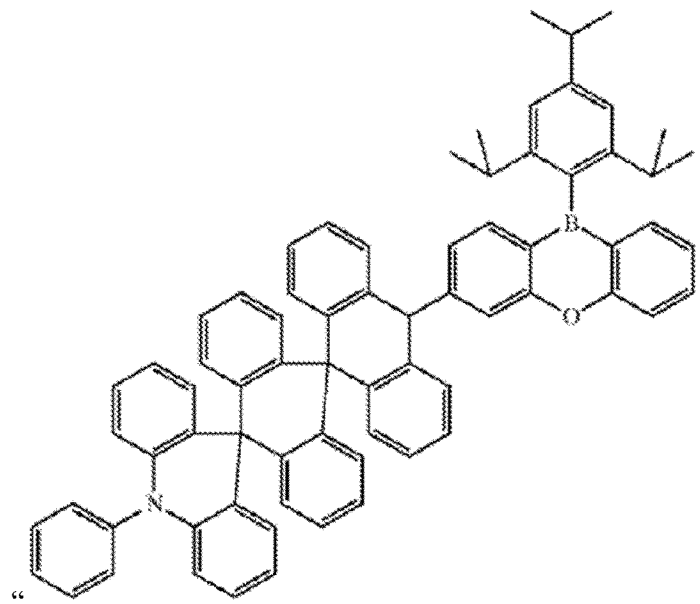

" and insert

Signed and Sealed this
Twenty-fourth Day of September, 2024

Katherine Kelly Vidal
*Director of the United States Patent and Trademark Office*

17
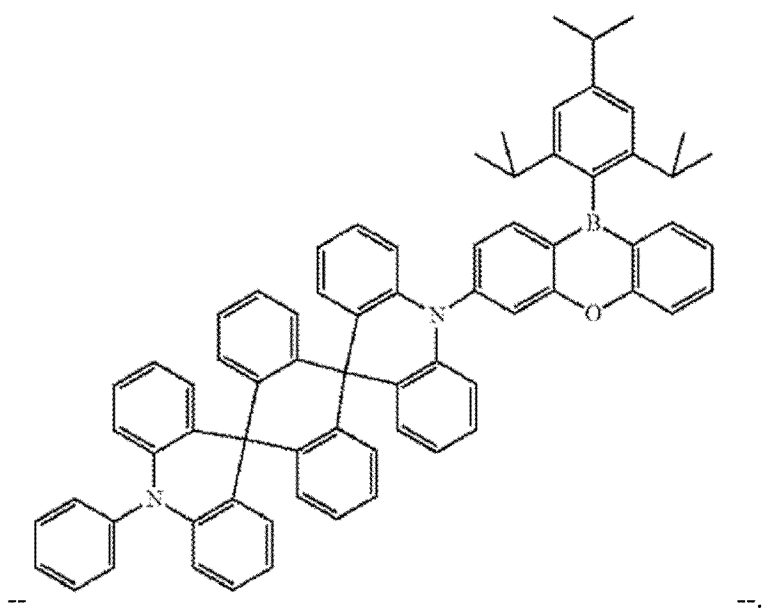
-- --.
In Column 77, Line 18, in Claim 4, delete "0" and insert -- O --.
In Column 77, Lines 30-46, in Claim 6, delete
Formula 1-1
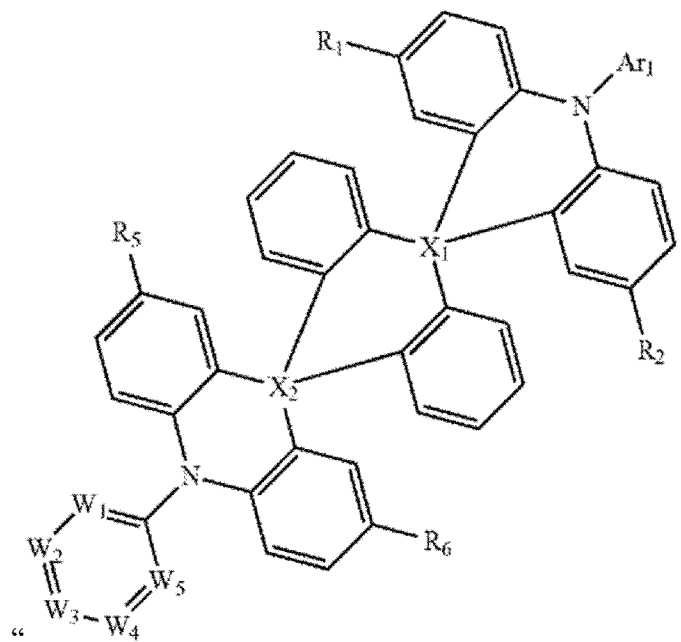
" " and insert

CERTIFICATE OF CORRECTION (continued)
U.S. Pat. No. 11,018,306 B2

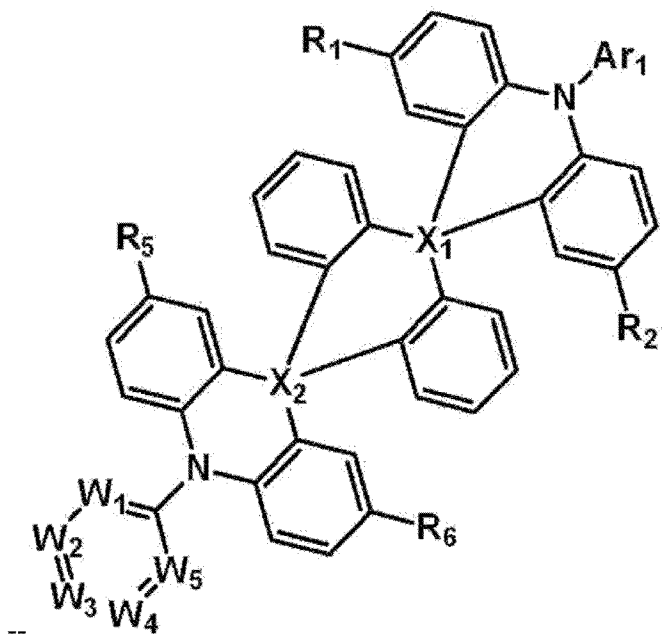

-- --.

In Column 96, Line 34, in Claim 9, delete "LiF/AI," and insert -- LiF/Al, --.

In Column 97, Lines 15-34, in Claim 9, delete

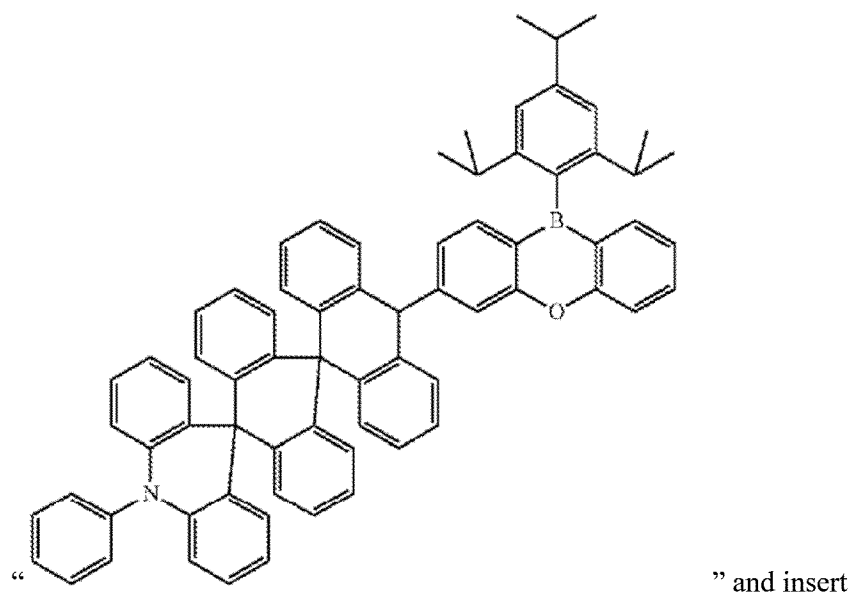

" and insert

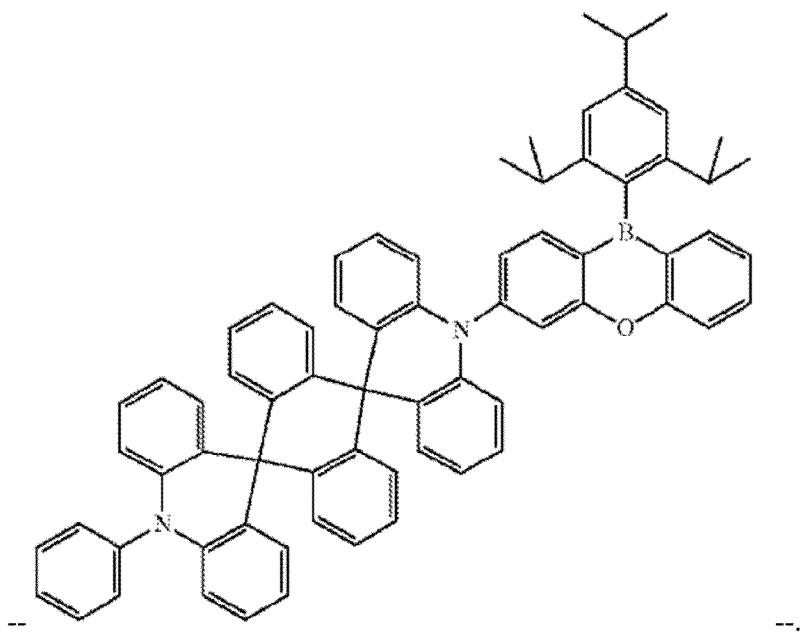
In Column 99, Line 56, in Claim 13, delete "0" and insert -- O --.